(12) United States Patent
Chappellet et al.

(10) Patent No.: US 9,493,394 B2
(45) Date of Patent: *Nov. 15, 2016

(54) PHOTOALIGNING MATERIALS

(71) Applicant: ROLIC AG, Zug (CH)

(72) Inventors: Sabrina Chappellet, Village-Neuf (FR); Jean-Francois Eckert, Kientzville (FR); Mohammed Ibn-Elhaj, Allschwil (CH); Frederic Lincker, Schiltigheim (FR); Satish Palika, Zofingen (CH); Hubert Seiberle, Weil am Rhein (DE); Qian Tang, Oberwil (CH); Eva Veenstra, Lorrach (DE)

(73) Assignee: ROLIC AG, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/349,265

(22) PCT Filed: Sep. 28, 2012

(86) PCT No.: PCT/EP2012/004068
§ 371 (c)(1),
(2) Date: Apr. 2, 2014

(87) PCT Pub. No.: WO2013/050121
PCT Pub. Date: Apr. 11, 2013

(65) Prior Publication Data
US 2014/0249244 A1    Sep. 4, 2014

(30) Foreign Application Priority Data

Oct. 3, 2011 (EP) .................................... 11183661
Jul. 18, 2012 (EP) .................................... 12176811

(51) Int. Cl.
| | | |
|---|---|---|
| C09K 19/00 | (2006.01) |
| C07C 65/28 | (2006.01) |
| C07C 229/60 | (2006.01) |
| C08G 73/10 | (2006.01) |
| G02F 1/1337 | (2006.01) |
| C07C 255/13 | (2006.01) |
| C07C 255/57 | (2006.01) |
| C07D 207/24 | (2006.01) |
| C07F 7/18 | (2006.01) |
| C08G 69/26 | (2006.01) |
| C09K 19/04 | (2006.01) |

(52) U.S. Cl.
CPC ............. *C07C 65/28* (2013.01); *C07C 229/60* (2013.01); *C07C 255/13* (2013.01); *C07C 255/57* (2013.01); *C07D 207/24* (2013.01); *C07F 7/1836* (2013.01); *C08G 69/26* (2013.01); *C08G 73/1025* (2013.01); *G02F 1/133711* (2013.01); *G02F 1/133719* (2013.01); *G02F 1/133723* (2013.01); *G02F 1/133788* (2013.01); *C09K 2019/0448* (2013.01); *Y10T 428/1005* (2015.01); *Y10T 428/1014* (2015.01)

(58) Field of Classification Search
CPC .......... Y10T 428/10; Y10T 428/1005; Y10T 428/1014; Y10T 428/1023; C08G 69/26; C08G 69/40; C08G 73/10; C08G 73/1025; G02F 1/133365; G02F 1/13378; G02F 1/133788; G02F 1/133711; G02F 1/133715; G02F 1/133723; C07C 229/60; C09K 2019/0448; C08L 79/08; C08L 79/085
USPC ............. 428/1.1, 1.2, 1.23, 1.25; 250/492.1; 528/184, 330, 353; 524/555, 558; 526/312, 321; 522/176

See application file for complete search history.

(56) References Cited

U.S. PATENT DOCUMENTS

| | | |
|---|---|---|
| 3,080,418 A | 3/1963 | Sullivan et al. |
| 6,340,506 B1 | 1/2002 | Buchecker et al. |
| 6,649,230 B1 | 11/2003 | Seiberle et al. |
| 6,831,148 B2 | 12/2004 | Buchecker et al. |
| 2003/0039768 A1 | 2/2003 | Buchecker et al. |
| 2011/0065859 A1 | 3/2011 | Bury et al. |
| 2012/0114907 A1 | 5/2012 | Eckert et al. |
| 2012/0316317 A1 | 12/2012 | Eckert et al. |
| 2014/0342086 A1 | 11/2014 | Ibn-Elhaj et al. |

FOREIGN PATENT DOCUMENTS

| | | |
|---|---|---|
| DE | 1 078 120 A | 3/1960 |
| EP | 1 801 097 A1 | 6/2007 |
| GB | 872355 A | 7/1961 |
| JP | 58-109479 A | 6/1983 |
| JP | 59-190945 A | 10/1984 |
| JP | 60-13740 A | 1/1985 |
| JP | 2009-58867 A | 3/2009 |
| TW | 201331264 A1 | 8/2013 |
| WO | 00/59966 A1 | 10/2000 |
| WO | 01/53384 A1 | 7/2001 |
| WO | 2008/135131 A1 | 11/2008 |
| WO | 2011/098461 A1 | 8/2011 |

OTHER PUBLICATIONS

J. March, Advanced Organic Chemistry Second Edition, pp. 363 and 365.
International Search Report for PCT/EP2012/004068 dated Nov. 19, 2012.

*Primary Examiner* — Ruiyun Zhang

(74) *Attorney, Agent, or Firm* — Sughrue Mion, PLLC

(57) ABSTRACT

The present invention relates to polymer, homo- or copolymer or oligomer for the photoalignment of liquid crystals, especially for the planar orientation of liquid crystals, comprising a main chain and a side chain, wherein the side chain and/or main chain comprises a polar group, compositions thereof, and its use for optical and electro optical devices, especially liquid crystal devices (LCDs).

26 Claims, No Drawings

PHOTOALIGNING MATERIALS

CROSS REFERENCE TO RELATED APPLICATIONS

This application is a National Stage of International Application No. PCT/EP2012/004068 filed Sep. 28, 2012 (claiming priority based on European Patent Application No. 11183661.5, filed Oct. 3, 2011, and European Patent Application No. 12176811.3, filed Jul. 18, 2012), the contents of which are incorporated herein by reference in their entirety.

The present invention relates to polymer, homo- or copolymer or oligomer for the photoalignment of liquid crystals, especially for the planar orientation of liquid crystals, comprising a main chain and a side chain, wherein the side chain and/or main chain comprises a polar group, compositions thereof, and its use for optical and electro optical devices, especially liquid crystal devices (LCDs).

There is an ever-growing demand to develop new photo-aligning materials for optical and electro-optical applications.

In the present invention new photo-aligning material was found which gives access to an economic manufacturing process and low energy consuming LCDs without decreasing the required technical properties.

Thus the present invention relates in a first aspect to a compound of formula (I), especially for the planar orientation, preferably for IPS modes of liquid crystals, especially in LCDs liquid crystal displays,

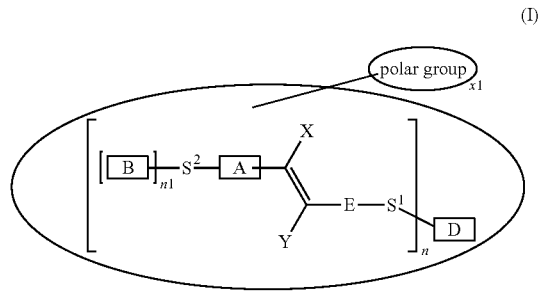

wherein,

A represents an unsubstituted or substituted carbocyclic or heterocyclic aromatic group selected from a monocyclic ring of five or six atoms, two adjacent monocyclic rings of five or six atoms, a bicyclic ring system of eight, nine or ten atoms, or a tricyclic ring system of thirteen or fourteen atoms or a group "E";

polar group represents a chemical group having a delocalisation of its electronical density or/and inducing a delocalisation of the electronical density of its neighbouring atom;

x1 is an integer from 1 to 15, preferably an integer from 1 to 10; more preferably 1, 2, or 3 and most preferred 1;

B represents a straight-chain or branched $C_1$-$C_{16}$alkyl group, wherein one or more —C—, —CH—, —CH$_2$— or —CH$_3$ group may independently from each other be unreplaced or replaced by at least one heteroatom or/and by a primary, secondary, tertiary or quaternary nitrogen, such as an ammonium cation, or/and a linking group; and wherein the $C_1$-$C_{16}$alkyl group is unsubstituted or at least ones substituted, preferably substituted in the terminal position of the $C_1$-$C_{16}$alkyl group, by a polar group, di-($C_1$-$C_{16}$alkyl)amino, $C_1$-$C_6$alkyloxy, nitro and/or halogen;

more preferred B is a straight-chain $C_1$-$C_{12}$alkyl, wherein at least one —C—, —CH—, —CH$_2$— or —CH$_3$ group is independently from each other be unreplaced or replaced by at least one heteroatom, preferably the —C—, —CH—, —CH$_2$— group is unreplaced or replaced by —O— or —S—, and further preferably the —CH$_3$ group is unreplaced or replaced by a secondary, or tertiary amine; halogen, such as fluoro, chloro, bromo, iodo, and more preferably fluoro and/or chloro, and most preferably fluoro; or/and a linking group, which is preferably an unsubstituted or substituted alicyclic or aromatic group, —CH=CH—, —C≡C—, single bond, heteroatom, —O—, —CO, —CO—O—, —O—CO—,

—CN, —NR$^1$— and wherein:

$R^1$ represents a hydrogen atom or $C_1$-$C_6$alkyl;

with the proviso that oxygen atoms of linking groups are not directly linked to each other; or/and B is a straight-chain $C_1$-$C_{12}$alkyl, wherein at least one —C—, —CH—, —CH$_2$— or —CH$_3$ group is independently from each other be unreplaced or replaced by at least one group selected from —O—(CH$_2$)$_n$—, —OCO—(CH$_2$)$_n$—, OOC—(CH$_2$)$_n$—, —NH—(CH$_2$)$_n$—, —S—(CH$_2$)$_n$—, SSC—(CH$_2$)$_n$—, —SCS—(CH$_2$)$_n$—, —O—(CH$_2$)$_n$—O—, —O—(CH$_2$)$_n$—COO—, —O—(CH$_2$)$_n$—OCO—, OOC—(CH$_2$)$_n$—O—, —OCO—(CH$_2$)$_n$—O—, —O—(CH$_2$)$_n$—NH—, —NH—(CH$_2$)$_n$—O—, OOC—(CH$_2$)$_n$—NH—, —NH—(CH$_2$)$_n$—COO—, —OCO—(CH$_2$)$_n$—NH—, —OCO—(CH$_2$)$_n$—NH—, NH—(CH$_2$)$_n$—NH—, —S—(CH$_2$)$_n$—S—, —S—(CH$_2$)$_n$—CSS—, —S—(CH$_2$)$_n$—SCS—, SSC—(CH$_2$)$_n$—S—, —SCS—(CH$_2$)$_n$—S—, —SCS—(CH$_2$)$_n$—S—, —O—(CH$_2$)$_n$—S—, —O—(CH$_2$)$_n$—CSS—, —O—(CH$_2$)$_n$—SCS—, OOC—(CH$_2$)$_n$—S—, —OCO—(CH$_2$)$_n$—S—, —OCO—(CH$_2$)$_n$—S—, —S—(CH$_2$)$_n$—O—, —S—(CH$_2$)$_n$—COO—, —S—(CH$_2$)$_n$—OCO—, —SSC—(CH$_2$)$_n$—O—, —SCS—(CH$_2$)$_n$—O—, —SCS—(CH$_2$)$_n$—O—, —S—(CH$_2$)$_n$—NH—, —NH—(CH$_2$)$_n$—S—, SSC—(CH$_2$)$_n$—NH—, —NH—(CH$_2$)$_n$—CSS—, —SCS—(CH$_2$)$_n$—NH—, and —SCS—(CH$_2$)$_n$—NH— group, and wherein the $C_1$-$C_{12}$alkyl group is unsubstituted or at least ones substituted, preferably substituted in the terminal position of the $C_1$-$C_{16}$alkyl group, by a polar group, di-($C_1$-$C_{16}$alkyl)amino, $C_1$-$C_6$alkyloxy, nitro and/or halogen;

wherein n is an integer from 1, 2, 3, 4, 5, 6, 7, 8, 9, 10, 11, 12 and preferably, 1, 2, 3, 4, 5, 6, and more preferably 2, 3, 4, 5, 6;

D represents a polymerizable group;

E represents an aromatic group, a single bond, an oxygen atom, a sulphur atom, —NH—, —N($C_1$-$C_6$alkyl)-, —CR$^2$R$^3$, —OCO—, —COO—, —OOC—, —NHCO—, —CONH—, —CONR$^2$—, —NR$^2$CO, —SCS, —CO—, wherein R$^2$ and R$^3$ are independently from each other hydrogen or a cyclic, straight-chain or branched, substituted or unsubstituted $C_1$-$C_{24}$alkyl, wherein one or more —C—, —CH—, —CH$_2$— group(s) may be independently from each other unreplaced or replaced by a linking group, and with the proviso that at least one of R$^2$ and R$^3$ is not hydrogen;

$S^1$, $S^2$ each independently from each other represents a spacer unit;

X, Y each independently from each other represents hydrogen, fluorine, chlorine, nitrile, unsubstituted or with fluorine substituted $C_1$-$C_{12}$alkyl, in which one or more —$CH_2$— groups may be unreplaced or replaced by a linking group, preferably X and Y are independently from each other hydrogen or nitrile and more preferably X and Y are hydrogen or X is hydrogen and Y is nitrile or X is nitrile and Y is hydrogen;

n, n1 each independently from each other represents 1, 2, 3 or 4, preferably n1 is 1 and n is 1 or 2;

with the proviso that if n is 2, 3, or 4, each A, B, $x_1$, E, $S^1$, $S^2$, X, Y are identical or different; and if n1 is 2, 3 or 4 each B, $x_1$ is identical or different; and with the proviso that if B is substituted with at least one fluor then there is at least one additional polar group in (I); and preferably with the proviso that if B is fluoro than $S^2$ does not comprise a non-aromatic, aromatic, unsubstituted or substituted carbocyclic or heterocyclic group, and if $S^2$ comprises a non-aromatic, aromatic, unsubstituted or substituted carbocyclic or heterocyclic group which is substituted with fluoro then B comprises nitril, preferably terminal substituted with nitril;

preferably, wherein, if n>1, compound (I) has several side-chains [wherein side-chain has the meaning of structures (I) without the group D], which are linked to residue D at one atomic position within group D, e.g. two or three side chains linked to one single carbon atom within group D, or they can be linked to group D at different atomic positions within group D, e.g. at adjacent atomic positions within group D, or/and they can linked spaced further apart.

In a further preferred embodiment of the invention B of (I) is unsubstituted or substituted, branched or straight-chain $C_1$-$C_{16}$alkyl, respectively $C_1$-$C_{16}$alkylene, more preferably $C_1$-$C_{12}$alkyl, respectively $C_1$-$C_{12}$alkylene, wherein one or more, preferably non-adjacent, —C—, —CH—, —$CH_2$—, —$CH_3$ groups are unreplaced or independently from each other be replaced by at least a single bond, —CN, fluor, phenyl, —O—, NH, -diethylamine, $\equiv$, —COO, OCO.

The wording "polymerizable group" as used in the context of the present invention refers to a functional group that can be subjected to polymerization (optionally with other comonomers) to yield an oligomer, dendrimer or polymer according to the present invention. For a person skilled in the art it will be obvious which functional groups are intended for any specific polymer. Thus for example in case of "imid monomer" as the indicated polymer backbone group it is obvious to a person skilled in the art that the actual monomer units for polymerization to yield a polyimid are e.g. diamines and dianhydrides. Similarly regarding "urethane monomer" the actual monomer units are diols and diisocyanates.

D is preferably selected from unsubstituted or substituted acrylate, methacrylate, 2-chloroacrylate, 2-phenylacrylate, optionally N-lower alkyl substituted acrylamide, methacrylamide, 2-chloroacrylamide, 2-phenylacrylamide, vinyl, allyl, vinyl ether and ester, allyl ether and ester, carbonic acid ester, acetal, urea, maleinimide, norbornene, norbornene derivatives, epoxy, styrene and styrene derivatives, for example alpha-methylstyrene, p-methylstyrene, p-tert-butyl styrene, p-chlorostyrene, siloxane, silane, diamine, imide monomers, amic acid monomers and their esters, amidimide monomers, maleic acid and maleic acid derivatives, for example di-n-butyl maleate, dimethyl maleate, diethyl maleate, etc, fumaric acid and fumaric acid derivatives, for example, di-n-butyl fumarate, di-(2-ethylhexyl) fumarate, etc, urethanes or their corresponding homo- and copolymers.

More preferably the polymerizable group D is selected from acrylate, methacrylate, vinyl ether and ester, epoxy, styrene derivatives, siloxane, silane, maleinimide, diamine, norbornene, norbornene derivatives, imide monomers, amic acid monomers and their corresponding homo and copolymers, or an unsubstituted or substituted, aliphatic, aromatic and/or alicyclic diamine group.

More preferably D represents an unsubstituted or substituted, aliphatic, aromatic and/or alicyclic diamine group, siloxane, maleinimide, especially diamine group having from 1 to 40 carbon atoms; wherein the diamine group comprises an aliphatic group, which may comprise one or more heteroatom and/or bridging group;

and/or an aromatic group; and/or an alicyclic group.

In the context of the present invention the wording "polar group" has the above-given meaning and preferences and represents for example more preferably halogens, preferably fluoro, chloro, bromo or iodo, especially chloro or fluoro;

groups containing halogen, preferably fluoro-, chloro-, bromo-, iodo-alkyl, especially fluoro-, chloro-, -alkyl, more preferably fluoro-alkyl, especially trifluormethyl;

groups containing oxygen, preferably hydroxy, carbonyl, such as a ketone or aldehyde group, carbonate ester, carboxylate, carboxyl acid, carboxyl ester, ether, such as $C_1$-$C_6$alkoxy, acetal or ketal group, orthocarbonate ester, groups containing cations, anions, salts;

groups containing nitrogen, preferably carboxamide, primary amine, secondary amine, such as di-($C_1$-$C_{16}$alkyl) amino, tertiary amine, ammonium ion, primary ketimine, secondary ketimine, primary aldimine, secondary aldimine, aminocarbonyl, imide, azide, azo, cyanate, isocyanate, nitrate, nitrile, isonitrile, nitrosooxy, nitro, nitroso, pyridyl, groups containing sulfur, preferably sulfhydryl, sulfide, disulfide, sulfinyl, sulfonyl, sulfino, sulfo, thiocyanate, isothiocyanate, carbonothioyl groups containing phosphorus, preferably phosphino, phosphono, phosphate, unsubstituted or substituted, branched alkyl, wherein it may be at least one —C—, —CH—, or —$CH_2$— group be unreplaced or replaced by a heteroatom such as —O—, —S—, or by a primary, secondary, tertiary or quaternary nitrogen, which is the ammonium cation; preferably isopropyl, tert-butyl, sec-butyl, neopentyl, isopentyl;

unsubstituted or substituted, straight-chain alkyl, wherein at least one —C—, —CH—, or —$CH_2$— group is replaced by a heteroatom or by a primary, secondary, tertiary or quaternary nitrogen, which is the ammonium cation;

unsubstituted or substituted straight-chain or branched alkenyl, wherein one or more —C—, —CH—, —$CH_2$— group(s) may be independently from each other unreplaced or replaced by a linking group, and preferably wherein the -en-group is in the terminal position of the alkenyl group, especially —O-alkenyl, —OOC-alkenyl, —OCO-alkenyl, —OCNHalkenyl, —NHCOalkenyl, which is preferably alkylacryloyloxy, preferably methacryloyloxy, acryloyloxy, vinyl, vinyloxy, allyl, allyloxy;

unsubstituted or substituted straight-chain or branched alkynyl, wherein at least one —C—, —CH—, or —CH₂— group be unreplaced or replaced by a linking group, and preferably wherein the -yl-group is in the terminal position of the alkynyl group, especially —O-alkynyl, —OOC-alkynyl, —OCO-alkynyl, —OCN-Halkynyl, —NHCOalkynyl, which is preferably -≡-, -≡—CH₃, acetyl;

unsubstituted or substituted carbocyclic or heterocyclic aromatic group or alicyclic group, incorporating preferably five, six, ten of 14 ring atoms, e.g. furan, benzyl or phenyl, pyridinyl, pyridinium cation, pyrimidinyl, pyrimidinium cation, naphthyl, which may form ring assemblies, such as biphenylyl or triphenyl, which are uninterrupted or interrupted by at least a single heteroatom and/or at least a single bridging group; or fused polycyclic systems, such as phenanthryl, tetralinyl. Preferably aromatic group are benzyl, phenyl, biphenyl or triphenyl. More preferred aromatic groups are benzyl, phenyl and biphenyl; further unsubstituted or substituted alicyclic group is preferably a non-aromatic carbocyclic or heterocyclic group, wherein heterocyclic group denotes a carbocyclic group, wherein at least one —C—, —CH—, or —CH₂— group is unreplaced or replaced by a heteroatom such as —O—, —S—, or by a primary, secondary, tertiary or quaternary nitrogen, which is the ammonium cation; and preferably the alicyclic group is a ring system, with 3 to 30 carbon atoms, and preferably cyclopropyl, cyclobutyl, cyclopentyl, cyclopentyl, cyclohexyl, cyclohexyl, cyclohexadienyl, decalinyl, aziridinyl, oxiranyl, azrinyl, aziridium cation, oxirenyl, thiirenyl, diazirine diaziridium cation, oxaziridinyl, oxaziridium cation, dioxiranyl, azetidinyl, azetinium cation azete, azetidin cation, oxetanyl, oxetyl, thietanyl, thietyl, diazetidinyl, diazetidinium cation, dioxetanyl, dioxetyl, dithietanyl, dithietyl, oxolanyl, thiolanyl, pyrrolidinyl, pyrrolidinium cationpyrrole, thiophe, pyrrolyl, furanyl, dioxanyl, dioxolanyl, dithiolanyl, maleinimidyl, maleinamidyl, oxazolinyl, oxazolidinyl, oxazolidnium cation, oxazolyl, isooxazolyl, imidazolyl, imidazolium cation, imidazolidinyl, imidazolidinium cation, pyrazolidinyl, pyrazolidinium cation, pyrazolyl, pyrazolium cation, pyrazolinyl, thiazolidinyl, thiazolidinium cation, thiazolyl, thiazolium cation, thiazolinyl, isothiazolyl, furazanyl, oxadiazolyl, dithiazolyl, tetrazolyl, piperidinyl, a piperidium cation, a piperazium oxane, pyranyl, thianyl, thiopyranyl, piperazinyl, diazinyl, morpholinyl, oxazinyl, thiomorpholinyl, thiazinyl, dioxinyl, dioxanyl, dithianyl, dithiinyl, triazinyl, tetrazinyl, azepanyl, azepinyl, such as oxepanyl, oxepinyl, thiepanyl, thiepinyl, homopiperazinyl, diazepinyl, thiazepinyl, azocanyl, azocinyl, oxecanyl, quinolinyl, quinolinium cation, benzothiophenyl, indolyl, benzofuranyl, acridinyl, dibenzothiophenyl, carbazolyl, dibenzofuranyl; ammonium cation, selected from an imidazolium cation, a pyrazolium cation.

Preferred is in the context of the present invention the wording "polar group" represents for example preferably halogens, preferably fluoro, chloro, bromo or iodo, especially chloro or fluoro;

groups containing halogen, preferably fluoro-, chloro-, bromo-, iodo-alkyl, especially fluoro-, chloro-, -alkyl, more preferably fluoro-alkyl, especially trifluormethyl;

groups containing oxygen, preferably hydroxy, carbonyl, such as a ketone or aldehyde group, carbonate ester, carboxylate, carboxyl acid, carboxyl ester, ether, such as $C_1$-$C_6$alkoxy, acetal or ketal group, orthocarbonate ester, groups containing nitrogen, preferably carboxamide, primary amine, secondary amine, such as di-($C_1$-$C_{16}$alkyl)amino, tertiary amine, ammonium ion, primary ketimine, secondary ketimine, primary aldimine, secondary aldimine, aminocarbonyl, imide, azide, azo, cyanate, isocyanate, nitrate, nitrile, isonitrile, nitrosooxy, nitro, nitroso, pyridyl, unsubstituted or substituted straight-chain or branched alkynyl, which is preferably -≡-, -≡—CH₃, acetyl;

unsubstituted or substituted carbocyclic or heterocyclic aromatic group or alicyclic group, incorporating preferably five, six, ten or 14 ring atoms, e.g. furan, benzyl or phenyl, pyridinyl, pyridinium cation, pyrimidinyl, pyrimidinium cation, naphthyl, which may form ring assemblies, such as biphenylyl or triphenyl, which are uninterrupted or interrupted by at least a single heteroatom and/or at least a single bridging group; or fused polycyclic systems, such as phenanthryl, tetralinyl. Preferably aromatic group are benzyl, phenyl, biphenyl or triphenyl. More preferred aromatic groups are benzyl, phenyl and biphenyl;

More preferred are chloro or fluoro, trifluoromethyl, ether, such as $C_1$-$C_6$alkoxy, di-($C_1$-$C_{16}$alkyl)amino, nitrile, pyridyl, unsubstituted or substituted straight-chain or branched alkynyl, which is preferably -≡-, -≡—CH₃, acetyl; unsubstituted or substituted carbocyclic or heterocyclic aromatic group or alicyclic group, incorporating preferably five, six, ten or 14 ring atoms, e.g. furan, benzyl or phenyl, pyridinyl, pyridinium cation, pyrimidinyl, pyrimidinium cation, naphthyl, which may form ring assemblies, such as biphenylyl or triphenyl, which are uninterrupted or interrupted by at least a single heteroatom and/or at least a single bridging group; or fused polycyclic systems, such as phenanthryl, tetralinyl. Preferably aromatic group are benzyl, phenyl, biphenyl or triphenyl. More preferred aromatic groups are benzyl, phenyl and biphenyl;

Most preferred is chloro or fluoro, trifluoromethyl, ether, such as $C_1$-$C_6$alkoxy, di-($C_1$-$C_{16}$alkyl)amino, nitrile, pyridyl, unsubstituted or substituted straight-chain or branched alkynyl, which is preferably -≡-, -≡—CH₃, acetyl; unsubstituted or substituted benzyl, phenyl or biphenyl; and especially preferred is nitrile.

In a preferred embodiment of the invention any substituent of the invention may represent a polar group.

In a further preferred embodiment the present invention relates to compound of formula (I'):

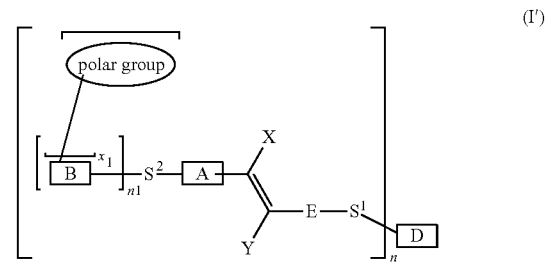

wherein,

A represents an unsubstituted or substituted carbocyclic or heterocyclic aromatic group selected from a monocyclic ring of five or six atoms, two adjacent monocyclic rings of five or six atoms, a bicyclic ring system of eight, nine or ten atoms, or a tricyclic ring system of thirteen or fourteen atoms or a group "E";
and
wherein the following compound residue of formula (I'), the compound residue (Ia)

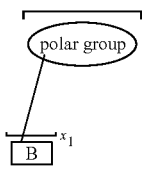

(Ia)

represents a straight-chain or branched $C_1$-$C_{16}$alkyl group having at least one terminal polar group,
$x_1$ is an integer from 1 to 15, preferably an integer from 1 to 10; more preferably 1, 2, or 3 and most preferred 1;
A, D, B, E, $S^1$, $S^2$, X, Y, n, n1 have the above-described meanings and preferences.

In a further preferred embodiment the present invention relates to compound of formula (I):
wherein,
A represents a unsubstituted or substituted carbocyclic or heterocyclic aromatic group selected from a monocyclic ring of five or six atoms, two adjacent monocyclic rings of five or six atoms, a bicyclic ring system of eight, nine or ten atoms, or a tricyclic ring system of thirteen or fourteen atoms; or represents a single bond, an oxygen atom, a sulphur atom, —NH—, —N($C_1$-$C_6$alkyl)-, —$CR^2R^3$, —OCO—, —COO—, —OOC—, —NHCO—, —CONH—, —$CONR^2$—, —$NR^2CO$, —SCS, —CO—, wherein $R^2$ and $R^3$ are independently from each other hydrogen or a cyclic, straight-chain or branched, substituted or unsubstituted $C_1$-$C_{24}$alkyl, wherein one or more —C—, —CH—, —$CH_2$— group(s) may be independently from each other unreplaced or replaced by a linking group, and with the proviso that at least one of $R^2$ and $R^3$ is not hydrogen;
polar group as described above within the above given meanings and preferences, and most preferably a nitrile group, and
$x_1$ is an integer from 1 to 3, preferably 1,
B has the meanings and preferences and provisos as described above;
D represents unsubstituted or substituted diamine, acrylate, methacrylate, siloxane silane, maleinimide, preferably diamine, preferably an aliphatic, aromatic or alicyclic polymerizable diamine group having from 1 to 40 carbon atoms,
E represents an aromatic group, a single bond, an oxygen atom, a sulphur atom, —NH—, —N($C_1$-$C_6$alkyl)-, —$CR^2R^3$, —OCO—, —COO—, —OOC—, —NHCO—, —CONH—, —$CONR^2$—, —$NR^2CO$, —SCS, —CO—, wherein $R^2$ and $R^3$ are independently from each other hydrogen or a cyclic, straight-chain or branched, substituted or unsubstituted $C_1$-$C_{24}$alkyl, wherein one or more —C—, —CH—, —$CH_2$— group(s) may be independently from each other unreplaced or replaced by a linking group, and with the proviso that at least one of $R^2$ and $R^3$ is not hydrogen;
$S^1$, $S^2$ each independently from each other represents a spacer unit;
X, Y each independently from each other represents hydrogen, fluorine, chlorine, nitrile, unsubstituted or with fluorine substituted $C_1$-$C_{12}$alkyl, in which one or more —C—, —CH—, —$CH_2$— groups may be unreplaced or replaced by a linking group;
n is 1, 2, 3 or 4,
with the proviso that if n is 2, 3, or 4, each A, B, $x_1$, D, E, $S^1$, $S^2$, X, Y may be identical or different.

The term "linking group", as used in the context of the present invention is preferably be selected from an unsubstituted or substituted alicyclic group, preferably cyclohexylen, or an unsubstituted or substituted aromatic group, single bond, heteroatom, cationic carbohydrogen group such as —(C+)—, —O—, —CO, -arylen-, —CO—O—, —O—CO—,

—CN, —$NR^1$—, —$NR^1$—CO—, —CO—$NR^1$—, —$NR^1$—CO—O—, —O—CO—$NR^1$—, —$NR^1$—CO—$NR^1$—, —CH═CH—, —C≡C—, —O—CO—O—, and —Si($CH_3$)$_2$—O—Si($CH_3$)$_2$—, and wherein:
$R^1$ represents a hydrogen atom or $C_1$-$C_6$alkyl;
with the proviso that oxygen atoms of linking groups are not directly linked to each other.

Substituents of the substituted alicyclic or aromatic group of the linking groups my be one or more and, are preferably halogen, such as fluor, chloro, bromo, iodo, and preferably fluoro and/chloro and more preferably fluor; or $C_1$-$C_6$alkoxy, such as preferably methoxy, or trifluoromethyl.

The term "spacer unit" as used in the context of the present invention, is preferably a single bond, a cyclic, straight-chain or branched, substituted or unsubstituted $C_1$-$C_{24}$alkylen, wherein one or more, preferably non-adjacent, —C—, —CH—, —$CH_2$— group may independently from each other be unreplaced or replaced by at least one linking group as described above and/or by at least one non-aromatic, aromatic, unsubstituted or substituted carbocyclic or heterocyclic group connected via bridging groups.

In a further preferred embodiment the spacer $S^1$ and $S^2$ independently from each other represent a single bond or a spacer unit, which is a cyclic, straight-chain or branched, substituted or unsubstituted $C_1$-$C_{24}$alkylen, especially $C_1$-$C_{12}$alkylen, especially $C_1$-$C_8$alkylen, more especially $C_1$-$C_6$alkylen, most especially $C_1$-$C_4$alkylen; within the above-given preferences;
in which one or more, preferably non-adjacent, —C—, —CH—, —$CH_2$— group may be unreplaced or at least once replaced by a linking group, wherein the linking group is preferably an unsubstituted or substituted alicyclic group, preferably cyclohexylen, or an unsubstituted or substituted aromatic group, single bond, heteroatom, —O—, —CO, -arylen-, —CO—O—, —O—CO—, —$NR^1$—, —$NR^1$—CO—O—, —CO—$NR^1$—, —$NR^1$—CO—O—, —O—CO—$NR^1$—, —$NR^1$—CO—$NR^1$—, —CH═CH—, —C≡C—, —O—CO—O— and wherein:
$R^1$ represents a hydrogen atom or $C_1$-$C_6$alkyl; and more preferably an unsubstituted or substituted cyclohexylen, or an unsubstituted or substituted phenylen, single bond, —O—, —CO, -arylen-, —CO—O—, —O—CO—, —$NR^1$—, —$NR^1$—CO—O—, —CO—$NR^1$—, —$NR^1$—CO—O—, —O—CO—$NR^1$—, —$NR^1$—CO—$NR^1$—, —CH═CH—, —C≡C—, —O—CO—O— and wherein:

$R^1$ represents a hydrogen atom or $C_1$-$C_6$alkyl,
with the proviso that oxygen atoms of linking groups are not directly linked to each other; or/and
$C_1$-$C_{24}$alkylen, in which one or more, preferably non-adjacent, —C—, —CH—, —CH$_2$— group may be unreplaced or at least once replaced by a non-aromatic, aromatic, unsubstituted or substituted carbocyclic or heterocyclic group connected via bridging groups.

Substituents of the aromatic, alicyclic group or phenylene, cylohexylen or the carbocyclic or heterocyclic group in $S^1$ or $S^2$ are preferably, at least one halogen, such as preferably chloro or fluoro, trifluoromethyl, $C_1$-$C_6$alkoxy, preferably methoxy, ethoxy, propoxy, butoxy, pentoxy, hexoxy.

Preferably, the non-aromatic, aromatic, unsubstituted or substituted carbocyclic or heterocyclic group connected via bridging groups of $S^1$ and $S^2$ each independently from each other represents formula (IV):

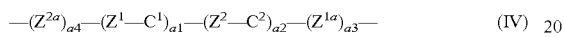

wherein:

$C^1$, $C^2$ each independently represents a non-aromatic, aromatic, optionally substituted carbocyclic or heterocyclic group, preferably connected to each other via the bridging groups $Z^1$ and $Z^2$ and/or $Z^{1a}$, preferably $C^1$ and $C^2$ are connected at the opposite positions via the bridging groups $Z^1$ and $Z^2$ and/or $Z^{1a}$, so that groups $S^1$ and/or $S^2$ have a long molecular axis, and $Z^1$, $Z^2$, $Z^{1a}$, $Z^{2a}$ each independently represents a bridging group, preferably selected from —CH(OH)—, —CH$_2$—, —O—, —CO—, —CH$_2$(SO)—, —SO—, —CH$_2$(SO)—, —SO$_2$—, —CH$_2$(SO$_2$)—, —COO—, —OCO—, —COCF$_2$—, —CF$_2$CO—, —S—CO—, —CO—S—, —SOO—, —OSO—, —SOS—, —CH$_2$—CH$_2$—, —OCH$_2$—, —CH$_2$O—, —CH=CH—, —C≡C—, —CH=CH—COO—, —OCO—CH=CH—, —CH=N—, —C(CH$_3$)=N—, —O—CO—O—, —N=N— or a single bond,
wherein $Z^{2a}$ is linked to B and $Z^{1a}$ is linked to A of formula (I) or (I'), $a_1$, $a_2$, $a_3$, $a_4$ each independently represents an integer from 0 to 3, such that $a_1+a_2+a_3+a_4 \leq 6$; preferably $a_3$ and $a_4$ are 0 and $a_1+a_2$ are 1, 2, 3 or 4, more preferably 1, 2, and most preferably 1, preferably with the proviso that if $S^2$ is substituted or unsubstituted phenyl linked by a single bond to A in formula (I) or (I') is excluded.

Further more preferably, the non-aromatic, aromatic, unsubstituted or substituted carbocyclic or heterocyclic group of $S^1$ represents formula (IV):

$C^1$, $C^2$ are selected from a compound of group $G^1$, wherein group $G^1$ is:

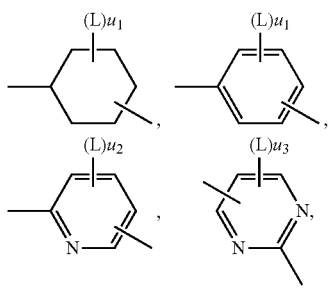

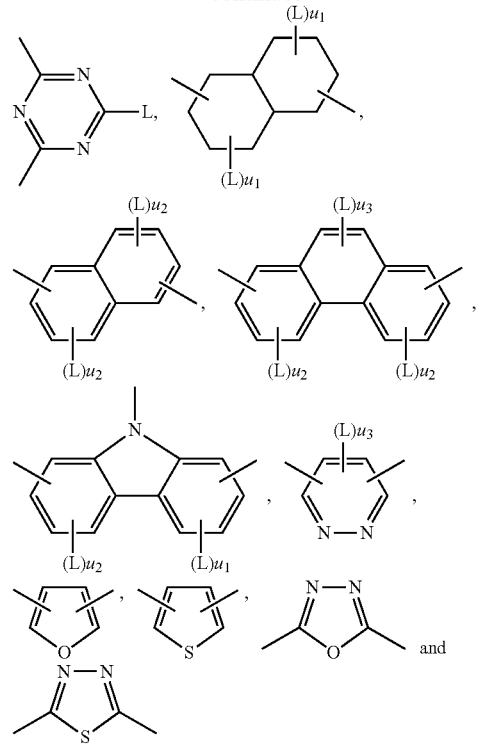

wherein:

"—" denotes the connecting bonds of $C^1$ and $C^2$ to the adjacent groups in formula (IV); and L is —CH$_3$, —OCH$_3$, CF$_3$, —COCH$_3$, polar group, nitro, nitrile, halogen, such as fluor or chlor, CH$_2$=CH—, CH$_2$=C(CH$_3$)—, CH$_2$=CH—(CO)O—, CH$_2$=CH—O—, CH$_2$=C(CH$_3$)—(CO)O—, or CH$_2$=C(CH$_3$)—O—, $u_1$ is an integer from 0 to 4; and
$u_2$ is an integer from 0 to 3; and
$u_3$ is an integer from 0 to 2; and $Z^1$, $Z^2$, $Z^{1a}$ $Z^{2a}$ each independently represents —O—, —CO—, —OCO—, —OCO—, —COCF$_2$—, —CF$_2$CO—, —CH$_2$—CH$_2$—, —OCH$_2$—, —CH$_2$O—, —CH=CH—, —C≡C—, —CH=CH—OCO—, —OCO—CH=CH— or a single bond; with the proviso that heteroatoms are not directly linked to each other, and $a_1$, $a_2$, $a_3$, $a_4$ each independently represents an integer from 0 to 3, such that $a_1+a_2+a_3+a_3 \leq 6$; preferably $a_3$ is 0 and $a^1+a^2 \leq 4$.

Most preferred, the non-aromatic, aromatic, unsubstituted or substituted carbocyclic or heterocyclic group connected via bridging groups of $S^1$ represents formula (IV):
wherein:

$C^1$, $C^2$ each independently represents a unsubstituted or substituted 1,4-phenylene, 2-methoxy-1,4-phenylene, 3-methoxy-1,4-phenylene, 2-trifluoromethyl-1,4-phenylene, 5-methoxy-1,4-phenylene, 2-fluor-1,4-phenylene, 3-fluor-1,4-phenylene, 5-fluor-1,4-phenylene, 2,3,5,6-tetrafluor-1,4-phenylene, 1,4-cyclohexylene or a 4,4'-biphenylene group; and $Z^1$, $Z^2$, $Z^{1a}$, $Z^{2a}$ each independently represents —O—, —CO—, —OCO—, —OCO—, —CH$_2$—CH$_2$—, —OCH$_2$—, —CH$_2$O—, —CH=CH—, —C≡C—, —CH=CH—COO—, —OCO—CH=CH— or a single bond; and $a_1, a_2, a_3, a_4$ are independently 0 or 1, preferably $a_3$ and $a_4$ 0.

Especially most preferably, the non-aromatic, aromatic, unsubstituted or substituted carbocyclic or heterocyclic group connected via bridging groups of $S^1$ represents formula (IV): wherein:

$C^1, C^2$ each independently represents with at least one fluor, methoxy or trifluoromethyl substituted or unsubstituted 1,4-phenylene; and $Z^1, Z^2, Z^{1a}, Z^{2a}$ each independently represents —O—, —CO—, —COO—, —OCO—, —CH$_2$—CH$_2$—, —OCH$_2$—, —CH$_2$O—, —CH=CH—, —C≡C—, —CH=CH—OCO—, —OCO—CH=CH—, or a single bond; and $a_1, a_2, a_3, a_4$ are independently 0 or 1, preferably $a_3$ and $a_4$ are 0.

More preferred, the non-aromatic, aromatic, unsubstituted or substituted carbocyclic or heterocyclic group connected via bridging groups of $S^2$ represents formula (IV), wherein:

$C^1, C^2$ are selected from group $G^1$, with the above given meaning; and $Z^1, Z^2, Z^{1a}, Z^{2a}$ each independently represents —O—, —CO—, —COO—, —OCO—, —COCF$_2$—, —CF$_2$CO—, —CH$_2$—CH$_2$—, —OCH$_2$—, —CH$_2$O—, —CH=CH—, —C≡C—, —CH=CH—COO—, —OCO—CH=CH— or a single bond; with the proviso that heteroatoms are not directly linked to each other, and $a_1, a_2, a_3, a_4$ are each independently represents an integer from 0 to 3, such that $a_1+a_2+a_3+a_4 \leq 6$, and preferably $a_1+a_2 \leq 4$ and $a_3$ and $a_4$ are 0; and wherein preferably $S^2$ is linked to A via $Z^1$.

Most preferred the non-aromatic, aromatic, unsubstituted or substituted carbocyclic or heterocyclic group connected via bridging groups of $S^2$ represents formula (IV): wherein $C^1, C^2$ each independently represents a 1,4-phenylene which is unsubstituted or mono or poly-substituted by a halogen atom, polar group, and/or by an alkoxy, alkylcarbonyloxy or an alkyloxycarbonyl group, having form 1 to 10 carbon atoms, 1,4-cyclohexylene or a 4,4'-biphenylene group; and $Z^1, Z^2, Z^{1a}, Z^{2a}$ each independently represents —COO—, —OCO—, —CH$_2$—CH$_2$—, —OCH$_2$—, —CH$_2$O—, —CH=CH—, —C≡C—, —CH=CH—COO—, —OCO—CH=CH— or a single bond; and $a_1, a_2, a_3, a_4$ are independently 0 or 1, wherein preferably $S^2$ is linked to A via $Z^1$, preferably with the proviso that in $S^2$ substituted or unsubstituted phenyl linked by a single bond to A in formula (I) or (I') is excluded.

Especially most preferred, the non-aromatic, aromatic, unsubstituted or substituted carbocyclic or heterocyclic group connected via bridging groups of $S^2$ represents formula (IV):

$S^2$ represents a group of formula (IVa)

  (IVa)

wherein:
$C^1$ represents a non-aromatic, aromatic, unsubstituted or substituted carbocyclic or heterocyclic group, preferably selected from a compound of group $G^1$, and $Z^1, Z^{1a}, Z^{2a}$ each independently from each other represent —COO—, —OCO—, —OCO(C$_1$-C$_6$)alkyl, —COOCH$_2$(C$_1$-C$_6$)alkyl-, —CH$_2$—CH$_2$—, —OCH$_2$—, —CH$_2$O—, —CH=CH—, —C≡C—, —CH=CH—COO—, —OCO—CH=CH—, or a single bond, or a straight-chain or branched, substituted or unsubstituted C$_1$-C$_8$alkylen, wherein one or more —CH$_2$— group may independently from each other be replaced by a linking group, preferably by —O—, as described above;

$a_1, a_3$, represents independently from each other 1, and $a_4$ 0 or 1, wherein preferably $S^2$ is linked to A via $Z^1$, preferably with the proviso that in $S^2$ substituted or unsubstituted phenyl linked by a single bond to A in formula (I) or (I') is excluded.

Further, especially most preferred, the non-aromatic, aromatic, unsubstituted or substituted carbocyclic or heterocyclic group connected via bridging groups of $S^2$ represents formula (IVa)

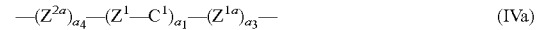  (IVa)

wherein:
$C^1$ represents a substituted or unsubstituted 1,4-phenylene, cyclohexylene which is unsubstituted or mono or poly-substituted by a halogen atom, and/or by an alkoxy, alkylcarbonyloxy or an alkyloxycarbonyl group, having form 1 to 10 carbon atoms, $Z^1, Z^{1a}, Z^{2a}$ each independently from each other represent —COO—, —OCO—, —CH$_2$—CH$_2$—, —OCH$_2$—, —CH$_2$O—, —CH=CH—, —C≡C—, —CH=CH—COO—, —OCO—CH=CH—, or a single bond, or a straight-chain or branched, substituted or unsubstituted C$_1$-C$_8$alkylen, wherein one or more —C—, —CH—, —CH$_2$— group may independently from each other be replaced by a linking group as described above, preferably by —O—, —COO—, —OCO—, more preferred $Z^{2a}$ is a single bond, $a_1, a_3$ represents independently from each other 1, $a_4$ is 0 or 1, wherein preferably $S^2$ is linked to A via $Z^1$, preferably with the proviso that in $S^2$ substituted or unsubstituted phenyl linked by a single bond to A in formula (I) or (I') is excluded.

More preferably $S^1$ is a single bond, a non-aromatic, aromatic, unsubstituted or substituted carbocyclic or heterocyclic group or

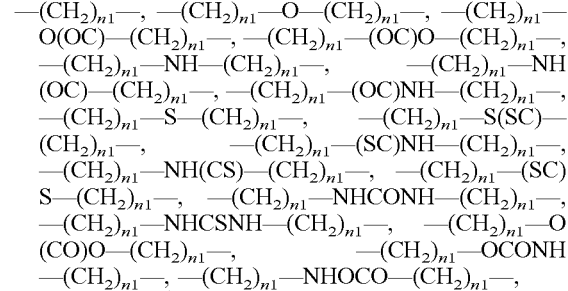

most preferably $S^1$ is a single bond, phenylene or
—(CH$_2$)$_{n1}$—, —(CH$_2$)$_{n1}$—O(OC)—(CH$_2$)$_{n1}$—, —(CH$_2$)$_{n1}$—NH(CO)O—(CH$_2$)$_{n1}$—, preferably —(CH$_2$)$_1$—, —(CH$_2$)$_2$—, —(CH$_2$)$_5$—, —(CH$_2$)$_8$—, —O(OC)—(CH$_2$)$_6$—, —O(OC)—(CH$_2$)$_8$—, —(CH$_2$)$_3$—NH(CO)O—(CH$_2$)$_3$—.

wherein n1 is independently from each other is 0, 1, 2, 3, 4, 5, 6, 7, 8, 9, 10, 11, 12 and preferably 0, 1, 2, 3, 4, 5, 6, and more preferably 0, 1, 2, 3, 4 and most preferably 0, 1 or 2.

More preferably, the spacer $S^2$ is a single bond, straight-chain or branched, substituted or unsubstituted C$_1$-C$_8$alkylen, more especially C$_1$-C$_6$alkylen, most especially C$_1$-C$_4$alkylen; within the above-given preferences; in which one or more, preferably non-adjacent, —C—, —CH—, —CH$_2$— group may be unreplaced or at least once replaced by an unsubstituted or substituted alicyclic group, preferably cyclohexylen, or an unsubstituted or substituted aromatic group, single bond, heteroatom, —O—, —CO, -arylen-, —CO—O—, —O—CO—, —O—CO—O—; and more preferably by an unsubstituted or substituted cyclohexylen, or an unsubstituted or substituted phenylen, single bond, —O—, —CO, -arylen-, —CO—O—, —O—CO—, —O—CO—O— and wherein:

with the proviso that oxygen atoms of linking groups are not directly linked to each other.

A bridging group as used in the context of the present invention is preferably selected from —CH(OH)—, —CO—, —CH$_2$(CO)—, —SO—, —CH$_2$(SO)—, —SO$_2$—, —CH$_2$(SO$_2$)—, —COO—, —OCO—, —COCF$_2$—, —CF$_2$CO, —S—CO—, —CO—S—, —SOO—, —OSO—, —SOS—, —O—CO—O—, —CH$_2$—CH$_2$—, —OCH$_2$—, —CH$_2$O—, —CH=CH—, —C≡C—, —(C$_1$-C$_5$alkyl)$_{1-6}$ C=CH—COO—, —CH=CH—COO—, —OCO—CH=CH—, —OCO—CH=C(C$_1$-C$_5$alkyl)$_{1-6}$CH—, —CH=N—, —C(CH$_3$)=N—, —N=N—, heteroatom, cationic carbohydrogen group such as —(C+)—, or a single bond; or a cyclic, straight-chain or branched, substituted or unsubstituted C$_1$-C$_{24}$alkylen, wherein one or more —C—, —CH—, —CH$_2$— groups may independently from each other be unreplaced or replaced by a linking group as described above.

In the context of the present invention alkyl has the meaning of unsubstituted or substituted alkyl, wherein substituted alkyl has also the meaning alkylen.

Alkyl, alkyloxy, alkoxy, alkylcarbonyloxy, acryloyloxyalkoxy, acryloyloxyalkyl, acryloyloxyalken, alkyloxycarbonyloxy, alkylacryloyloxy, methacryloyloxyalkoxy, methacryloyloxyalkyl, methacryloyloxyalken, alkylmethacryloyloxy, alkylmethacryloyloxy, alkylvinyl, alkylvinyloxy and alkylallyloxy and alkylene, as used in the context of the present invention denote with their alkyl residue, respectively their alkylene residue, a cyclic, straight-chain or branched, substituted or unsubstituted alkyl, respectively alkylene, in which one or more, preferably non-adjacent, —C—, —CH—, or —CH$_2$— group may be unreplaced or replaced by a linking group, preferably replaced by —O—, NH, —COO, OCO.

Further, in the context of the present invention "alkyl" is branched or straight chain, unsubstituted or substituted alkyl, preferably C$_1$-C$_{40}$alkyl, especially C$_1$-C$_{30}$alkyl, preferably C$_1$-C$_{20}$alkyl, more preferably C$_1$-C$_{16}$alkyl, most preferably C$_1$-C$_{10}$alkyl and especially most preferably C$_1$-C$_6$alkyl. Accordingly alkylen is for example C$_1$-C$_{40}$alkylen, especially C$_1$-C$_{30}$alkylen, preferably C$_1$-C$_{20}$alkylen, more preferably C$_1$-C$_{16}$alkylen, most preferably C$_1$-C$_{10}$alkylen and especially most preferably C$_1$-C$_6$alkylen.

In the context of the present invention the definitions for alkyl given below, are applicable to alkylene in analogy.

C$_1$-C$_6$alkyl is for example methyl, ethyl, propyl, isopropyl, butyl, sec.-butyl, tert.-butyl, pentyl or hexyl.

C$_1$-C$_{10}$alkyl is for example methyl, ethyl, propyl, isopropyl, butyl, sec.-butyl, tert.-butyl, pentyl, hexyl, heptyl, octyl, nonyl, decyl.

C$_1$-C$_{16}$alkyl is for example methyl, ethyl, propyl, isopropyl, butyl, sec.-butyl, tert.-butyl, pentyl, hexyl, heptyl, octyl, nonyl, decyl, undecyl, dodecyl, tridecyl, tetradecyl, pentadecyl or hexadecyl.

C$_1$-C$_{20}$alkyl is for example methyl, ethyl, propyl, isopropyl, butyl, sec.-butyl, tert.-butyl, pentyl, hexyl, heptyl, octyl, nonyl, decyl, undecyl, dodecyl, tridecyl, tetradecyl, pentadecyl, hexadecyl, heptadecyl, octadecyl, nondecyl, eicosyl.

C$_1$-C$_{24}$alkyl is for example methyl, ethyl, propyl, isopropyl, butyl, sec.-butyl, tert.-butyl, pentyl, hexyl, heptyl, octyl, nonyl, decyl, undecyl, dodecyl, tridecyl, tetradecyl, pentadecyl, hexadecyl, heptadecyl, octadecyl, nondecyl, eicosyl.

C$_1$-C$_{30}$alkyl is for example methyl, ethyl, propyl, isopropyl, butyl, sec.-butyl, tert.-butyl, pentyl, hexyl, heptyl, octyl, nonyl, decyl, undecyl, dodecyl, tridecyl, tetradecyl, pentadecyl, hexadecyl, heptadecyl, octadecyl, nondecyl, eicosyl, heneicosyl, tricosyl, tetracosy, pentacosyl, hexacosdy, heptacosyl, octacosyl, nonacosy or triacontyl.

C$_1$-C$_{40}$alkyl is for example methyl, ethyl, propyl, isopropyl, butyl, sec.-butyl, tert.-butyl, pentyl, hexyl, heptyl, octyl, nonyl, decyl, undecyl, dodecyl, tridecyl, tetradecyl, pentadecyl, hexadecyl, heptadecyl, octadecyl, nondecyl, eicosyl, heneicosyl, tricosyl, tetracosy, pentacosyl, hexacosdy, heptacosyl, octacosyl, nonacosy, triacontyl or tetracontyl.

C$_1$-C$_6$alkoxy is for example methoxy, ethoxy, propoxy, isopropoxy, butoxy, sec.-butoxy, tert.-butoxy, pentoxy or hexoxy.

C$_1$-C$_{20}$acryloyloxyalkylene, preferably C$_1$-C$_{10}$acryloyloxyalkylene, C$_1$-C$_6$ acryloyloxyalkylene is for example acryloyloxymethylen, acryloyloxyethylene, acryloyloxypropylene, acryloyloxyisopropylene, acryloyloxybutylene, acryloyloxy-sec.-butylene, acryloyloxypentylene, acryloyloxyhexylene, acryloyloxyheptylene, acryloyloxyoctylene, acryloyloxynonylene, acryloyloxydecylene, acryloyloxyundecylene, acryloyloxydodecane, acryloyloxytridecylene, acryloyloxytetradecylene, acryloyloxypentyldecane, acryloyloxyhexadecylene, acryloyloxyheptadecylene, acryloyloxyoctadecylene, acryloyloxynondecylene, acryloyloxyeicosylene.

C$_1$-C$_{20}$methacryloyloxyalkylene, preferably C$_1$-C$_{10}$methacryloyloxyalkylene, C$_1$-C$_6$ methacryloyloxyalkylene is for example methacryloyloxymethylen, methacryloyloxyethylene, methacryloyloxypropylene, methacryloyloxyisopropylene, methacryloyloxybutylene, methacryloyloxy-sec.-butylene, methacryloyloxypentylene, methacryloyloxyhexylene, methacryloyloxyheptylene, methacryloyloxyoctylene, methacryloyloxynonylene, methacryloyloxydecylene, methacryloyloxyundecylene, methacryloyloxydodecane, methacryloyloxytridecylene, methacryloyloxytetradecylene, methacryloyloxypentyldecane, methacryloyloxyhexadecylene, methacryloyloxyheptadecylene, methacryloyloxyoctadecylene, methacryloyloxynondecylene, methacryloyloxyeicosylene.

C$_1$-C$_{20}$acryloyloxyalkoxy, preferably C$_1$-C$_{10}$acryloyloxyalkoxy, C$_1$-C$_6$acryloyloxyalkoxy is for example acryloyloxymethoxy, acryloyloxyethoxy, acryloyloxypropoxy, acryloyloxyisopropoxy, acryloyloxybutoxy, acryloyloxy-sec.-butoxy, acryloyloxypentoxy, acryloyloxyhexoxy, acryloyloxyheptoxy, acryloyloxyoctoxy, acryloyloxynonoxy, acryloyloxydecoxy, acryloyloxyundecoxy, acryloyloxydodecanoxy, acryloyloxytridecyloxy.

C$_1$-C$_{20}$methacryloyloxyalkoxy, preferably C$_1$-C$_{10}$methacryloyloxyalkoxy, C$_1$-C$_6$ methacryloyloxyalkoxy is for example methacryloyloxymethoxy, methacryloyloxyethoxy, methacryloyloxypropoxy, methacryloyloxyisopropoxy, methacryloyloxybutoxy, methacryloyloxy-sec.-butoxy, methacryloyloxypentoxy, methacryloyloxyhexoxy, methacryloyloxyheptoxy, methacryloyloxyoctoxy, methacryloyloxynonoxy, methacryloyloxydecoxy, methacryloyloxyundecoxy, methacryloyloxydodecanoxy, methacryloyloxytridecyloxy.

An aliphatic group is for example a saturated or unsaturated, mono-, bi-, tri-, tetra-, penta-, hexa-, hepta-, octa-, nona-, deca-valent alkyl, alkylene, alkyloxy, alkylcarbonyloxy, acryloyloxy, alkylacryl, alkylmethacryl, alkyl(en)acryl (en), alkyl(en)methacryl(en), alkyloxycarbonyloxy, alkyloxycarbonyloxy methacryloyloxy, alkylvinyl, alkylvinyloxy or alkylallyloxy, which may comprise one or more heteroatom and/or bridging group.

An alicyclic group is preferably a non-aromatic group or unit and may be substituted or unsubstituted. Preferably an alicyclic group is a non-aromatic carbocyclic or heterocyclic group and represents for example ring systems, with 3 to 30 carbon atoms, as for example cyclopropane, cyclobutane, cyclopentane, cyclopentene, cyclohexane, cyclohexene, cyclohexadiene, decaline, tetrahydrofuran, dioxane, pyrrolidine, piperidine or a steroidal skeleton such as cholesterol. Preferred alicyclic group is cyclohexene. Substituents of an alicyclic group are halogen, preferably fluor or/and chloro, $C_1$-$C_6$alkoxy, preferably methoxy or trifluormethyl.

The term "aromatic", as used in the context of the present invention, preferably denotes unsubstituted or substituted carbocyclic and heterocyclic groups, incorporating five, six, ten or 14 ring atoms, e.g. furan, benzene or phenylene, pyridine, pyrimidine, naphthalene, which may form ring assemblies, such as biphenylene or triphenylene, which are uninterrupted or interrupted by at least a single heteroatom and/or at least a single bridging group; or fused polycyclic systems, such as phenanthrene, tetraline. Preferably aromatic group are benzene, phenylene, biphenylene or triphenylene. More preferred aromatic group is benzene, phenylene and biphenylene. Especially preferred substituents of an aromatic group or of a carbocyclic and heterocyclic groups are halogen, preferably fluor or/and chloro, $C_1$-$C_6$alkoxy, preferably methoxy or trifluormethyl.

A carbocyclic or heterocyclic aromatic group or alicyclic group incorporates preferably three, four, five, six, ten or 14 ring atoms, as for example aziridin, epoxy, cyclopropyl, furan, pyrolidin, oxazolin, imidazol, benzene, pyridine, triazine, pyrimidine, naphthalene, phenanthrene, biphenylene or tetraline units, preferably naphthalene, phenanthrene, biphenylene or phenylene, more preferably naphthalene, biphenylene or phenylene, and most preferably phenylene. Especially preferred substituents of carbocyclic and heterocyclic aromatic groups are halogen, preferably fluor or/and chloro, $C_1$-$C_6$alkoxy, preferably methoxy or trifluormethyl.

The unsubstituted or substituted carbocyclic or heterocyclic aromatic or alicyclic group is for example unsubstituted or mono- or poly-substituted. Preferred substituents of carbocyclic or heterocyclic aromatic groups are at least one trifluormethyl, halogen, such as fluor, chloro, bromo, iodo, especially fluor or/and cloro, and more especially fluor; hydroxyl, a polar group, acryloyloxy, alkylacryloyloxy, alkoxy, especially methoxy, ethoxy, propoxy; alkylcarbonyloxy, alkyloxycarbonyloxy, alkyloxocarbonyloxy, methacryloyloxy, vinyl, vinyloxy and/or allyloxy group, wherein the alkyl residue has preferably from 1 to 20 carbon atoms, and more preferably having from 1 to 10 carbon atoms. Preferred polar groups are nitro, nitrile or a carboxy group, and/or a cyclic, straight-chain or branched $C_1$-$C_{30}$alkyl, which is unsubstituted, mono- or poly-substituted. Preferred substitutents of $C_1$-$C_{30}$alkyl are methyl, fluorine and/or chlorine, wherein one or more, preferably non-adjacent, —C—, —CH—, —CH$_2$— group may independently of each other be replaced by a linking group. Preferably, the linking group is selected from —O—, —CO—, —COO— and/or —OCO—.

A monocyclic ring of five or six atoms is for example furan, benzene, preferably phenylene, pyridine, pyrimidine, pyridine cation, pyrimidine cation.

A bicyclic ring system of eight, nine or ten atoms is for example naphthalene, biphenylene or tetraline.

A tricyclic ring system of thirteen or fourteen atoms is for example phenanthrene.

The term "phenylene", as used in the context of the present invention, preferably denotes a 1,2-, 1,3- or 1,4-phenylene group, which is optionally substituted. Especially preferred substituents of phenylene are halogen, preferably fluor or/and chloro, $C_1$-$C_6$alkoxy, preferably methoxy or trifluormethyl. It is preferred that the phenylene group is either a 1,3- or a 1,4-phenylene group. 1,4-phenylene groups are especially preferred.

The term "halogen" denotes a chloro, fluoro, bromo or iodo substituent, preferably a chloro or fluoro substituent, and more preferably fluoro.

The term "heteroatom", as used in the context of the present invention is a neutral, anionic or cationic heteroatom and primarily denotes oxygen, sulphur and nitrogen, halogen, such as fluoro, chloro, bromo, iodo, and more preferably fluoro and/or chloro, and most preferably fluoro; preferably halogen, oxygen and nitrogen, in the latter case primary amine, secondary amine, tertiary amine or quaternary ammonium cation, preferably in the form of —NH—.

The term "optionally substituted" as used in the context of the present invention primarily means substituted by lower alkyl, such as $C_1$-$C_6$alkyl, lower alkoxy, such as $C_1$-$C_6$alkoxy, hydroxy, halogen or by a polar group as defined above.

The term "diamine" or "diamine compound" is to be understood as designating a chemical structure which has at least two amino groups, i.e. which may also have 3 or more amino groups. The at least two amino groups are preferably able to react with e.g. anhydrides as outlined in more detail below.

The term "dinitro" or "dinitro compound" is to be understood as designating a chemical structure which has at least two nitro groups, i.e. which may also have 3 or more nitro groups, and wherein the dinitro group is a precursor compound of the "diamino compound". The dinitro compound is conventionally converted to the diamino compound by reduction methods known in the art.

With respect to straight chain or branched alkyl, alkylene, alkoxy, alkylcarbonyloxy, acryloyloxyalkoxy, acryloyloxyalkyl, acryloyloxyalkene, alkyloxycarbonyloxy, alkylacryloyloxy, methacryloyloxyalkoxy, methacryloyloxyalkyl, methacryloyloxyalkene, alkylmethacryloyloxy, alkylmethacryloyloxy, alkylvinyl, alkylvinyloxy, alkylallyloxy and alkylene groups it is repeatedly pointed out that some or several of the —C—, —CH—, —CH$_2$— groups may be replaced e.g. by heteroatoms, but also by other groups, preferably bridging groups. In such cases it is generally preferred that such replacement groups are not directly linked to each other. It is alternatively preferred that heteroatoms, and in particular oxygen atoms are not directly linked to each other.

Preferably, A is unsubstituted or substituted phenanthrylene, naphthylene, biphenylene or phenylene, wherein the preferred substituent(s) is (are) a halogen atom, a hydroxy group and/or by a polar group, wherein the polar group is preferably nitro, nitrile, carboxy; and/or by acryloyloxy, alkylacryl, alkylmethacryl, alkyl(en)acryl, alkyl(en)methacryl, acrylenacryl, methacrylenalkyl, methacryloyloxy, vinyl, vinyloxy, allyl, allyloxy, and/or by a cyclic, straight-chain or branched alkyl, which is unsubstituted, mono- or poly-substituted by fluorine and/or chlorine, having from 1 to 20 carbon atoms, wherein one or more, preferably non-adjacent, —C—, —CH—, —CH$_2$— groups may independently be replaced by a linking group and or an aromatic or an alicyclic group, preferably the linking group is selected from —O—, —CO—, —CO—O—, —O—CO—.

More preferably A is substituted or unsubstituted naphthylene, biphenylene or phenylene, wherein the preferred substituent(s) is (are) halogen atom, hydroxy group and/or by acryloyloxy, alkylacryl, alkylmethacryl, acrylenacryl, methacrylenalkyl, methacryloyloxy, straight-chain or branched alkyl, alkoxy, alkylcarbonyloxy, and/or alkyloxycarbonyl groups, wherein the alkyl residue has from 1 to 20 carbon atoms.

Most preferably A is substituted or unsubstituted phenylene, preferably 1,4-phenylen, wherein the preferred substituent(s) is (are) a halogen atom, and/or by acryloyloxy or methacryloyloxy, and/or by an alkoxy, trifluoromethyl, alkylacryl, alkylmethacryl, acrylenacryl, methacrylenalkyl, alkylcarbonyloxy, and/or alkyloxycarbonyl groups, wherein the alkyl residue has from 1 to 10 carbon atoms.

A preferred embodiment of the present invention relates to polymer, homo- or copolymer or oligomer, which derives from or comprises at least one monomer (I), which is a compound of formula (I') as described above, wherein the following compound residue (Ia)

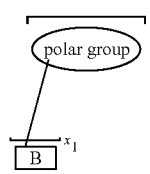

(Ia)

represents —CN, -halogen, especially chloro and/or fluor, —O—$C_1$-$C_6$alkoxy, a straight-chain or branched —O—$C_1$-$C_{16}$alkyl-O—$C_1$-$C_{16}$alkyl, a straight-chain or branched —O—$C_1$-$C_{16}$alkyl-Cl, a straight-chain or branched —O—$C_1$-$C_{16}$alkyl-≡, a straight-chain or branched —O—$C_1$-$C_{16}$alkyl-≡-$C_1$-$C_6$alkyl, phenylene, —N($C_1$-$C_6$alkyl)$_2$, a straight-chain or branched $C_1$-$C_{16}$alkyl-(polar group) group, especially a —O—$C_1$-$C_{16}$alkyl-(polar group) group, —NH—$C_1$-$C_{16}$alkyl-(polar group) group, —OOC—$C_1$-$C_{16}$alkyl-(polar group) group, —OCO—$C_1$-$C_{16}$alkyl-(polar group) group, —OCOO—$C_1$-$C_{16}$alkyl-(polar group) group, —NHCO—$C_1$-$C_{16}$alkyl-(polar group) group, —OCNH—$C_1$-$C_{16}$alkyl-(polar group) group, wherein $C_1$-$C_{16}$alkyl is preferably $C_1$-$C_6$alkyl more preferably $C_1$-$C_4$alkyl, and polar group is as described above within the above given meanings and preferences;

In a more preferred embodiment the polar group is preferably a nitrile group in the terminal position of the alkyl chain, and $x_1$ is 1.

D is preferably a diamines group, and more preferably a diamine group selected from formula (III):

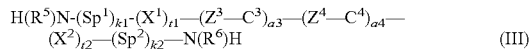

(III)

wherein:
$R^5$, $R^6$ each independently from each other represents a hydrogen atom or $C_1$-$C_6$alkyl;
$Sp^1$, $Sp^2$ each independently from each other represent an unsubstituted or substituted straight-chain or branched $C_1$-$C_{20}$alkylene, in which one or more —C—, —CH—, —CH$_2$— group may independently from each other be unreplaced or replaced by a linking group, and
$k^1$, $k^2$ each independently is an integer having a value of 0 or 1; and $X^1$, $X^2$ each independently represents a linking spacer, preferably selected from —O—, —S—, —NH—, N(CH$_3$)—, —CH(OH)—, —CO—, —CH$_2$(CO)—, —SO—, —CH$_2$(SO)—, —SO$_2$—, —CH$_2$(SO$_2$)—, —COO—, —OCO—, —OCO—O—, —S—CO—, —CO—S—, —SOO—, —OSO—, —SOS—, —CH$_2$—CH$_2$—, —OCH$_2$—, —CH$_2$O—, —CH═CH—, or —C≡C— or a single bond; and
$t^1$, $t^2$ each independently is an integer having a value of 0 or 1; and
$C^3$, $C^4$ each independently represents a non-aromatic, aromatic, substituted or unsubstituted carbocyclic or heterocyclic group, which may have a side chain T, and
$Z^3$ represents a bridging group; and
$Z^4$ represents a substituted or unsubstituted straight-chain or branched $C_1$-$C_{20}$alkylene group, in which one or more —C—, —CH—, —CH$_2$— group may independently from each other be unreplaced or replaced by a non-aromatic, aromatic, unsubstituted or substituted carbocyclic or heterocyclic group; and/or a heteroatom and/or by a bridging group as described above; preferably, $Z^4$ has one of the meanings of $Z^3$ or represents an unsubstituted or substituted straight-chain or branched $C_1$-$C_{14}$alkylene group, in which one or more, preferably non-adjacent, —C—, —CH—, —CH$_2$— group may be unreplaced or replaced by an oxygen atom and/or one or more carbon-carbon single bond is replaced by a carbon-carbon double or a carbon-carbon triple bond; and
$a_3$, $a_4$ are independently integers from 0 to 3, such that $a_3+a_4 \leq 4$; and wherein
D is at least once linked to at least one group $S^1$ in formula (I) via group $Sp^1$ and/or $Sp^2$; and/or linked via at least one non-aromatic, aromatic, substituted or unsubstituted carbocyclic or heterocyclic group of $C^3$ and/or of group $C^4$, and/or linked via at least one side chain T of group $C^4$ and/or of group $C^3$; and/or linked via group $Z^4$; and at least one of $k^1$, $k^2$, $a^3$ and $a^4$ is not equal to zero; and wherein
linking group and bridging group are as described above, and preferably compound of formula (I), wherein preferably, if n>1, then the side chains [i.e. structures (I) without the group D] can either be linked to the group D at one atomic position within group D, e.g. two or three side chains connected to one single carbon atom within group D, or they can be linked to group D at different atomic positions within group D, e.g. at adjacent atomic positions within group D, but also spaced further apart.

The term "side chain", T, represents a substituted or unsubstituted straight-chain or branched $C_1$-$C_{20}$alkylene group(s), in which one or more —C—, —CH—, —CH$_2$— group may independently from each other be unreplaced or replaced by a non-aromatic, aromatic, unsubstituted or substituted carbocyclic or heterocyclic group, or a heteroatom and/or by a bridging group, which is at least once linked to at least one group $S^1$ in formula (I).

Preferably D is selected from formula (III), wherein:
$C^3$, $C^4$ independently from each other are selected from a compound of group $G^2$, wherein group $G^2$ denotes:

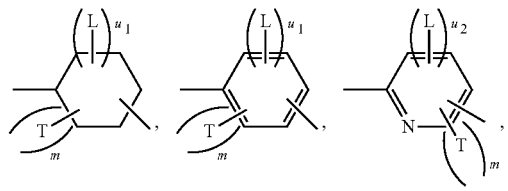

-continued

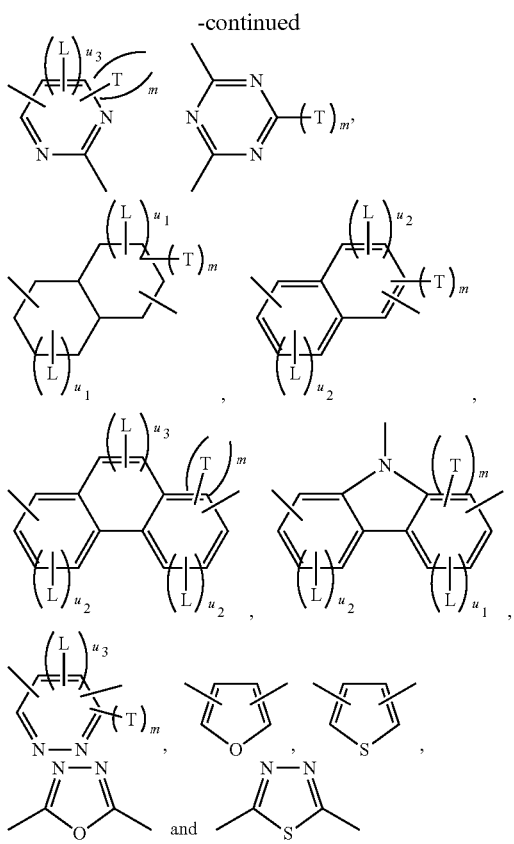

wherein

"—" denotes the connecting bonds of $C^3$ and $C^4$ to the adjacent groups of compound of formula (III) as described above; and L is —CH$_3$, —COCH$_3$, —OCH$_3$, nitro, nitrile, halogen, CH$_2$=CH—, CH$_2$=C(CH$_3$)—, CH$_2$=CH—(CO)O—, CH$_2$=CH—O—, —NR$^5$R$^6$, CH$_2$=C(CH$_3$)—(CO)O—, CH$_2$=C(CH$_3$)—O—, wherein:

R$^5$, R$^6$ each independently from each other represents a hydrogen atom or C$_1$-C$_6$alkyl;

T represents a substituted or unsubstituted straight-chain or branched C$_1$-C$_{20}$alkylene group, in which one or more —C—, —CH—, —CH$_2$— group may independently from each other be replaced by a non-aromatic, aromatic, unsubstituted or substituted carbocyclic or heterocyclic group, or a heteroatom and/or by a bridging group;

m is an integer from 0 to 2; preferably 1 or 0; and more preferably 0;

u$_1$ is an integer from 0 to 4, with the proviso that m+u$_1$ is ≤4; and u$_2$ is an integer from 0 to 3; with the proviso that m+u$_2$ is ≤0.3; and u$_3$ is an integer from 0 to 2; with the proviso that m+u$_3$ is ≤2.

D is more preferably selected from the following group of structures: substituted or unsubstituted o-phenylenediamine, p-phenylenediamine, m-phenylenediamine, biphenyl-diamine, aminophenylen-Z$^4$-phenylenamino, wherein Z$^4$ has the same meaning and preferences as given above; naphthylenediamine, benzidine, diaminofluorene, 3,4-diaminobenzoic acid, 3,4-diaminobenzyl alcohol dihydrochloride, 2,4-diaminobenzoic acid, L-(+)-threo-2-amino-1-(4-aminophenyl)-1,3-propanediol, p-aminobenzoic acid, [3,5-3h]-4-amino-2-methoxybenzoic acid, L-(+)-threo-2-(N,N-dimethylamino)-1-(4-aminophenyl)-1,3-propanediol, 2,7-diaminofluorene, 4,4'-diaminooctafluorobiphenyl, 3,3'-diaminobenzidine, 2,7-diamino-9-fluorenone, 3,5,3',5'-tetrabromo-biphenyl-4,4'-diamine, 2,2'-dichloro[1,1'-biphenyl]-4,4'-diamine, 3,9-diamino-1,11-dimethyl-5,7-dihydro-dibenzo(a,c)cyclohepten-6-one, dibenzo(1,2) dithiine-3,8-diamine, 3,3'-diaminobenzophenone, 3,3'-diaminodiphenylmethane, 4,4-bis-(3-amino-4-hydroxyphenyl)-valeric acid, 2,2-bis(3-amino-4-hydroxyphenyl)hexafluoropropane, 2,2-bis(3-amino-4-methylphenyl)hexafluoropropane, tetrabromo methylenedianiline, 2,7-diamino-9-fluorenone, 2,2-bis(3-aminophenyl)hexafluoropropane, bis-(3-amino-4-chlorophenyl)-methanone, bis-(3-amino-4-dimethylamino-phenyl)-methanone, 3-[3-amino-5-(trifluoromethyl)benzyl]-5-(trifluoromethyl)aniline, 1,5-diaminonaphthalene, benzidine-3,3'-dicarboxylic acid, 4,4'-diamino-1,1'-binaphthyl, 4,4'-diaminodiphenyl-3,3'-diglycolic acid, dihydroethidium, o-dianisidine, 2,2'-dichloro-5,5'-dimethoxybenzidine, 3-methoxybenzidine, 3,3'-dichlorobenzidine (diphenyl-d6), 2,2'-bis(trifluoromethyl)benzidine, 3,3'-bis(trifluoromethyl)benzidine, 3,3'-dichlorobenzidine-d6, tetramethylbenzidine, di-(aminophenyl)alkylen and from amino compounds listed below, which do not carry two amino groups and are taken as derivatives with at least one additional amino group:

aniline, 4-amino-2,3,5,6-tetrafluorobenzoic acid, 4-amino-3,5-diiodobenzoic acid, 4-amino-3-methylbenzoic acid, 4-amino-2-chlorobenzoic acid, 4-aminosalicylic acid, 4-aminobenzoic acid, 4-aminophthalic acid, 1-(4-aminophenyl)ethanol, 4-aminobenzyl alcohol, 4-amino-3-methoxybenzoic acid, 4-aminophenyl ethyl carbinol, 4-amino-3-nitrobenzoic acid, 4-amino-3,5-dinitrobenzoic acid, 4-amino-3,5-dichlorobenzoic acid, 4-amino-3-hydroxybenzoic acid, 4-aminobenzyl alcohol hydrochloride, 4-aminobenzoic acid hydrochloride, pararosaniline base, 4-amino-5-chloro-2-methoxybenzoic acid, 4-(hexafluoro-2-hydroxyisopropyl)aniline, piperazine-p-amino benzoate, 4-amino-3,5-dibromobenzoic acid, isonicotinic acid hydrazide p-aminosalicylate salt, 4-amino-3,5-diiodosalicylic acid, 4-amino-2-methoxybenzoic acid, 2-[2-(4-aminophenyl)-2-hydroxy-1-(hydroxymethyl)ethyl]isoindoline-1,3-dione, 4-amino-2-nitrobenzoic acid, ethyl 2-(4-aminophenyl)-3,3,3-trifluoro-2-hydroxypropanoate, ethyl 2-(4-amino-3-methylphenyl)-3,3,3-trifluoro-2-hydroxypropanoate, ethyl 2-(4-amino-3-methoxyphenyl)-3,3,3-trifluoro-2-hydroxypropanoate, 4-aminonaphthalene-1,8-dicarboxylic acid, 4-amino-3-chloro-5-methylbenzoic acid, 4-amino-2,6-dimethylbenzoic acid, 4-amino-3-fluorobenzoic acid, 4-amino-5-bromo-2-methoxybenzenecarboxylic acid, 3,3'-tolidine-5-sulfonic acid, or their derivatives, again with the proviso that compounds listed which do not carry two amino groups are taken as derivatives with at least one additional amino group.

The diamine groups D are commercial available or accessible by known methods. The second amino group is accessible for example by substitution reaction.

D is further more preferably selected from the group of the following compounds:

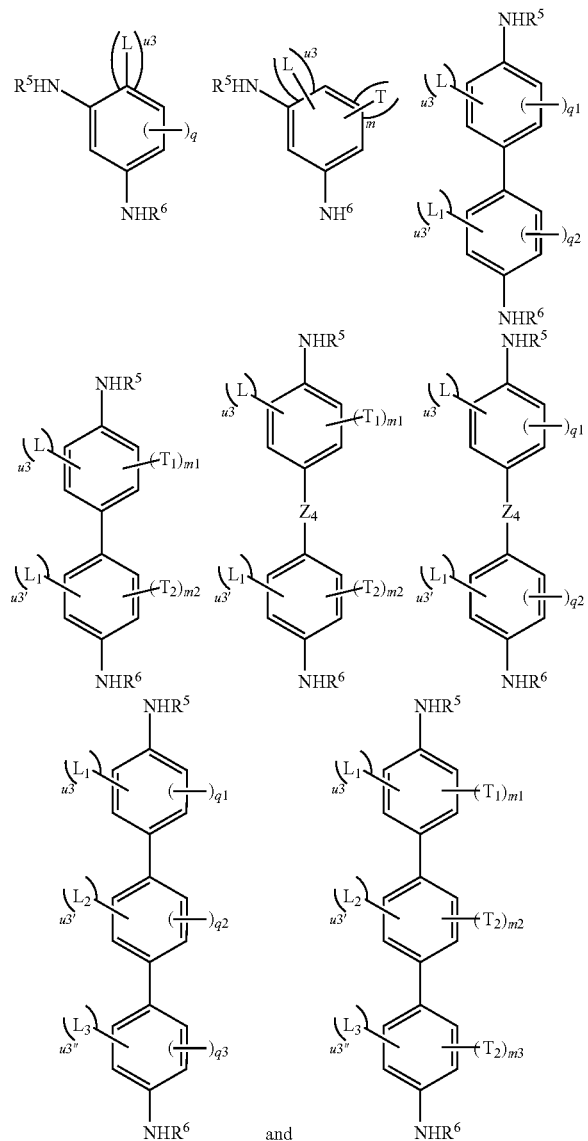

$R^5$, $R^6$ and $Z^4$ are as described above; and wherein

D is at least once linked to at least one group $S^1$ in formula (I) via a single bond "—"; or via a side chain T, $T_1$, $T_2$ or $T_3$; or via group $Z^4$;

with the proviso that u3+q, or u3+m is ≤4;

u3+q1 and/or u3'+q2 or/and u3+m1, or/and u3'+m2, or/and u3"+q3, or/and u3"+m3 is ≤4;

q1+q2, and m1+m2; and q1+q2+q3, and m1+m2+m3 is ≥1.

Most preferred are diamine compounds according to the invention, wherein D is a selected from the group of the following compounds: represents unsubstituted or substituted diamine, acrylate, methacrylate, siloxane silane, maleinimide, preferably diamine of the below given formulas

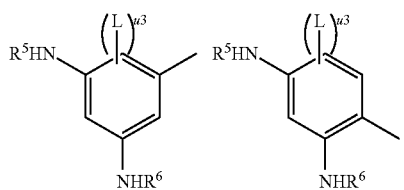

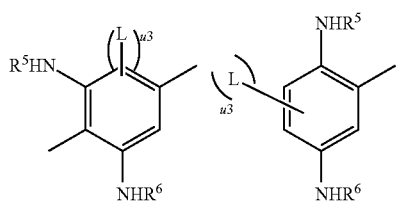

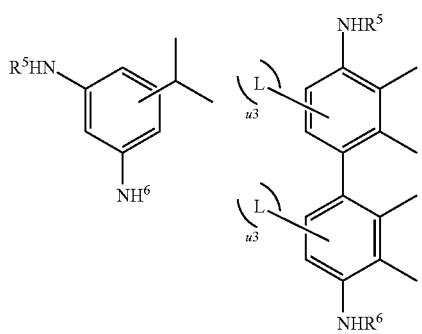

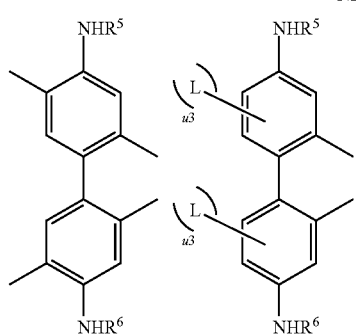

wherein

L, $L_1$, $L_2$ and $L_3$ are independently from each other —$CH_3$, —$COCH_3$, —$OCH_3$, nitro, nitrile, halogen, $CH_2$=CH—, $CH_2$=C($CH_3$)—, $CH_2$=CH—(CO)O—, $CH_2$=CH—O—, —$NR^5R^6$, $CH_2$=C($CH_3$)—(CO)O— or $CH_2$=C($CH_3$)—O—, T, $T_1$, $T_2$ and $T_3$ are independently from each other a substituted or unsubstituted straight-chain or branched $C_1$-$C_{20}$alkylene group, in which one or more —C—, —CH—, —$CH_2$— group(s) may independently from each other be replaced by a non-aromatic, aromatic, unsubstituted or substituted carbocyclic or heterocyclic group, and/or a heteroatom and/or by a bridging group;

"—" is a single bond, q is an integer of 1 or 2; and q1, q2 and q3 are independently from each other an integer from 0 to 2; preferably 1 or 2;

m is an integer of 1 or 2;

m1, m2 and m3 are independently from each other an integer from 0 to 2; preferably 1 or 2;

$u_3$, $u_3'$ and $u_3"$ are independently from each other an integer from 0 to 2;

-continued

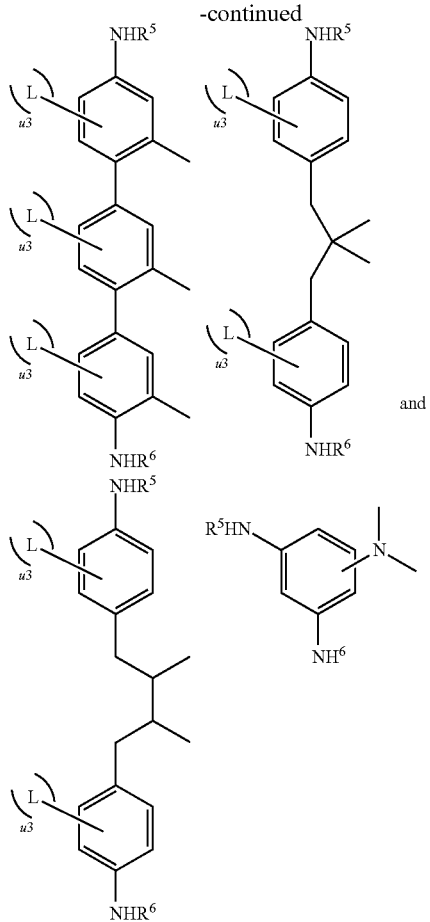

and

"—" denotes the linking(s) of D to $S^1$ in compound (I) and represents a single bond; and L is —CH$_3$, —COCH$_3$, —OCH$_3$, nitro, nitrile, halogen, CH$_2$=CH—, CH$_2$=C(CH$_3$)—, CH$_2$=CH—(CO)O—, CH$_2$=CH—O—, —NR$^5$R$^6$, CH$_2$=C(CH$_3$)—(CO)O— or CH$_2$=C(CH$_3$)—O—, wherein:

$R^5$, $R^6$ each independently from each other represents a hydrogen atom or $C_1$-$C_6$alkyl;

$u_3$ is an integer from 0 to 2.

In a further embodiment of the invention E preferably represents a substituted or unsubstituted phenylene, a single bond, —O—, —COO—, —OOC—, —NHCO—, —CONH—, —CONR$^2$—, —NR$^2$CO, —SCS, —CO—, most preferred E is —O—, —COO—, —OOC— or substituted or unsubstituted phenylene.

Another preferred embodiment of the present invention relates to a compound (I), referring to any of the preceding definitions comprising these compounds, wherein A represents phenanthrylene, biphenylene, naphthylene, or phenylene, which is unsubstituted or mono- or polysubstituted by a halogen atom, hydroxy group and/or by a polar group, preferably nitro, nitrile, carboxy; and/or by acryloyloxy, methacryloyloxy, vinyl, vinyloxy, allyl, allyloxy, and/or by a cyclic, straight-chain or branched $C_1$-$C_{12}$alkyl residue, which is unsubstituted, mono- or poly-substituted by fluorine and/or chlorine, wherein one or more —C—, —CH—, —CH$_2$— group may independently be replaced by a linking group and or an aromatic or an alicyclic group, or A is a single bond, —OCO—, —COO—, —OOC—, —NHCO—, —CONH—, —CONR$^2$—, —NR$^2$CO, —SCS, —CO—, wherein $R^2$ and $R^3$ are independently from each other hydrogen or a cyclic, straight-chain or branched, substituted or unsubstituted $C_1$-$C_{24}$alkyl, wherein one or more —C—, —CH—, —CH$_2$— group(s) may be independently from each other replaced by a linking group, and with the proviso that at least one of $R^2$ and $R^3$ is not hydrogen; and wherein the compound residue (Ia) of compound of formula (I) as described above

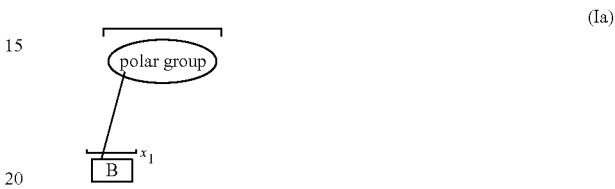 (Ia)

represents —CN, -halogen, especially chloro and/or fluor, —O—$C_1$-$C_6$alkoxy, a straight-chain or branched —O—$C_1$-$C_{16}$alkyl-O—$C_1$-$C_{16}$alkyl, a straight-chain or branched —O—$C_1$-$C_{16}$alkyl-Cl, a straight-chain or branched —O—$C_1$-$C_{16}$alkyl-≡, a straight-chain or branched —O—$C_1$-$C_{16}$alkyl-≡-$C_1$-$C_6$alkyl, phenylene, —N($C_1$-$C_6$alkyl)$_2$, a straight-chain or branched $C_1$-$C_{16}$alkyl-(polar group) group, especially a —O—$C_1$-$C_{16}$alkyl-(polar group) group, —NH—$C_1$-$C_{16}$alkyl-(polar group) group, —OOC—$C_1$-$C_{16}$alkyl-(polar group) group, —OCO—$C_1$-$C_{16}$alkyl-(polar group) group, —OCOO—$C_1$-$C_{16}$alkyl-(polar group) group, —NHCO—$C_1$-$C_{16}$alkyl-(polar group) group, —OCNH—$C_1$-$C_{16}$alkyl-(polar group) group, wherein $C_1$-$C_{16}$alkyl is preferably $C_1$-$C_6$alkyl more preferably $C_1$-$C_4$alkyl, and polar group is as described above within the above given meanings and preferences;

in a more preferred embodiment the polar group is preferably a nitrile group in the terminal position of the alkyl chain, and $x_1$ is 1, especially more preferred is a straight-chain or branched $C_1$-$C_{12}$alkyl group having a terminal polar group, wherein polar group is a nitrile group, and D represents unsubstituted or substituted diamine, acrylate, methacrylate, siloxane silane, maleinimide, preferably diamine, more preferably an optionally substituted aliphatic, aromatic or alicyclic diamine group having from 1 to 40 carbon atoms selected from formula (III),

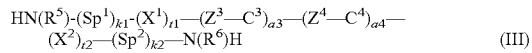 (III)

wherein $k^1$, $k^2$ are 0 or 1, and $t^1$, $t^2$ are 0, and $R^5$, $R^6$ are identical and represent a hydrogen atom, a methyl, an ethyl or an isopropyl group; and $C^3$, $C^4$ independently from each other are selected from compound of a group $G^2$ as described above;

$Z^3$ represents a group selected from —CH(OH)—, —CH(CH$_3$)—, —C(CH$_3$)$_2$—, —CO—, —COO—, —OCO—, —COCF$_2$—, —CF$_2$CO— or a single bond; and $Z^4$ has one of the meanings of $Z^3$ or represents a substituted or unsubstituted straight-chain or branched $C_1$-$C_{20}$alkylene, in which one or more, preferably non-adjacent, —C—, —CH—, —CH$_2$— group may independently from each other be replaced by cyclohexylen, phenylen, aromatic or non-aromatic N-heterocycle; or by a heteroatom and/or by an oxygen atom; and/or one or more carbon-carbon single bond is replaced by a carbon-carbon double or a carbon-carbon triple bond;

$a^3$, $a^4$ each independently represents an integer from 0 to 2 such that $a^3+-a^4 \leq 3$;

$Sp^1$, $Sp^2$, $X^1$, $X^2$ have the same meaning as described above;

E represents a substituted or unsubstituted aromatic group, preferably a, with flour, chlor, methoxy or trifluoromethyl substituted or unsubstituted phenylene, a single bond, —O—, —OCO—, —COO—, —OOC—, —NHCO—, —CONH—, —CONR²—, —NR²CO, —SCS, —CO—, $S^1$ represents a single bond or a spacer unit, which is a cyclic, straight-chain or branched, substituted or unsubstituted $C_1$-$C_{24}$alkylen, especially $C_1$-$C_{12}$alkylen, especially $C_1$-$C_8$alkylen, more especially $C_1$-$C_6$alkylen, most especially $C_1$-$C_4$alkylen; within the above-given preferences;

in which one or more, preferably non-adjacent, —C—, —CH—, —CH₂— group may be unreplaced or at least once replaced by a linking group, wherein the linking group is preferably an unsubstituted or substituted alicyclic group, preferably cyclohexylen, or an unsubstituted or substituted aromatic group, single bond, heteroatom, —O—, —CO, -arylen-, —CO—O—, —O—CO—, —NR¹—, —NR¹—CO—, —CO—NR¹—, —NR¹—CO—O—, —O—CO—NR¹—, —NR¹—CO—NR¹—, —CH=CH—, —C≡C—, —O—CO—O— and wherein:

$R^1$ represents a hydrogen atom or $C_1$-$C_6$alkyl; and more preferably an unsubstituted or substituted cyclohexylen, or an unsubstituted or substituted phenylen, single bond, —O—, —CO, -arylen-, —CO—O—, —O—CO—, —NR¹—, —NR¹—CO—, —CO—NR¹—, —NR¹—CO—O—, —O—CO—NR¹—, —NR¹—CO—NR¹—, —CH=CH—, —C≡C—, —O—CO—O— and wherein:

$R^1$ represents a hydrogen atom or $C_1$-$C_6$alkyl, with the proviso that oxygen atoms of linking groups are not directly linked to each other; or/and $C_1$-$C_{24}$alkylen, in which one or more, preferably non-adjacent, —C—, —CH—, —CH₂— group may be unreplaced or at least once replaced by a non-aromatic, aromatic, unsubstituted or substituted carbocyclic or heterocyclic group connected via bridging groups;

$S^2$ represents a single bond or a spacer unit, which is a cyclic, straight-chain or branched, substituted or unsubstituted $C_1$-$C_{24}$alkylen, especially $C_1$-$C_{12}$alkylen, especially $C_1$-$C_8$alkylen, more especially $C_1$-$C_6$alkylen, most especially $C_1$-$C_4$alkylen; within the above-given preferences; in which one or more, preferably non-adjacent, —C—, —CH—, —CH₂— group may be unreplaced or at least once replaced by a linking group, wherein the linking group is preferably an unsubstituted or substituted alicyclic group, preferably cyclohexylen, or an unsubstituted or substituted aromatic group, single bond, heteroatom, —O—, —CO, -arylen-, —CO—O—, —O—CO—, —NR¹—, —NR¹—CO—, —CO—NR¹—, —NR¹—CO—O—, —O—CO—NR¹—, —NR¹—CO—NR¹—, —CH=CH—, —C≡C—, —O—CO—O— and wherein:

$R^1$ represents a hydrogen atom or $C_1$-$C_6$alkyl; and more preferably an unsubstituted or substituted cyclohexylen, or an unsubstituted or substituted phenylen, single bond, —O—, —CO, -arylen-, —CO—O—, —O—CO—, —NR¹—, —NR¹—CO—, —CO—NR¹—, —NR¹—

CO—O—, —O—CO—NR¹—, —NR¹—CO—NR¹—, —CH=CH—, —C≡C—, —O—CO—O— and wherein:

$R^1$ represents a hydrogen atom or $C_1$-$C_6$alkyl, with the proviso that oxygen atoms of linking groups are not directly linked to each other; or/and $C_1$-$C_{24}$alkylen, in which one or more, preferably non-adjacent, —C—, —CH—, —CH₂— group may be unreplaced or at least once replaced by a non-aromatic, aromatic, unsubstituted or substituted carbocyclic or heterocyclic group of formula (IV):

$$—(Z^{2a})_{a4}—(Z^1—C^1)_{a1}—(Z^2—C^2)_{a2}—(Z^{1a})_{a3}— \quad (IV)$$

wherein:

$C^1$, $C^2$ each independently represents a non-aromatic, aromatic, unsubstituted or substituted carbocyclic or heterocyclic group, and $Z^1$, $Z^2$, $Z^{1a}$, $Z^{2a}$ each independently represents a bridging group, and $a^1$, $a^2$, $a^3$ each independently represents an integer from 0 to 3, such that $a_1+a_2+a_3+a_4 \leq 6$; preferably $a_3$ and $a_4$ are 0 and $a_1+a_2$ are 1, 2, 3 or 4, more preferably 1, 2, and most preferably 1, wherein the bridging groups $Z^1$, $Z^{1a}$ and $Z^2$, $Z^{2a}$ are as described above, preferably with the proviso that in S2 substituted or unsubstituted phenyl linked by a single bond to A in formula (I) or (I') is excluded;

X, Y are independently from each other hydrogen or nitrile, and n is 1, 2 or 3, and n1 is 1 or 2; preferably n1 is 1 with the proviso that if n is 2 or 3 each A, B, $x_1$, D, E, $S^1$ and $S^2$ may be identical or different, and if n1 is 2 each B, x1 may be identical or different.

A more preferred embodiment of the present invention relates to compounds (I), referring to any of the preceding definitions, and to alignment materials comprising these compounds wherein A represents a biphenylene, naphthylene or phenylene group, which is unsubstituted or mono- or poly-substituted by a halogen atom, a hydroxy group, and/or by acryloyloxy, and/or methacryloyloxy groups, and/or by straight-chain or branched alkyl, alkoxy, alkylcarbonyloxy, and/or alkyloxycarbonyl groups having from 1 to 20 carbon atoms, or a single bond, —OCO—, —COO—, —OOC—, —NHCO—, —CONH—, —CONR²—, —NR²CO, —SCS, —CO— wherein $R^2$ and $R^3$ are independently from each other hydrogen or a cyclic, straight-chain or branched, substituted or unsubstituted $C_1$-$C_{24}$alkyl, wherein one or more —C—, —CH—, —CH₂— group(s) may be independently from each other replaced by a linking group, and with the proviso that at least one of $R^2$ and $R^3$ is not hydrogen;

and wherein the compound residue (Ia) of compound of formula (I)

represents —CN, -halogen, especially chloro and/or fluor, —O—$C_1$-$C_6$alkoxy, a straight-chain or branched —O—$C_1$-

$C_{16}$alkyl-O—$C_1$-$C_{16}$alkyl, a straight-chain or branched —O—$C_1$-$C_{16}$alkyl-Cl, a straight-chain or branched —O—$C_1$-$C_{16}$alkyl-Ξ, a straight-chain or branched —O—$C_1$-$C_{16}$alkyl-Ξ-$C_1$-$C_6$alkyl, phenylene, —N($C_1$-$C_5$alkyl)$_2$, a straight-chain or branched $C_1$-$C_{16}$alkyl-(polar group) group, especially a —O—$C_1$-$C_{16}$alkyl-(polar group) group, —NH—$C_1$-$C_{16}$alkyl-(polar group) group, —OOC—$C_1$-$C_{16}$alkyl-(polar group) group, —OCO—$C_1$-$C_{16}$alkyl-(polar group) group, —OCOO—$C_1$-$C_{16}$alkyl-(polar group) group, —NHCO—$C_1$-$C_{16}$alkyl-(polar group) group, —OCNH—$C_1$-$C_{16}$alkyl-(polar group) group, wherein $C_1$-$C_{16}$alkyl is preferably $C_1$-$C_6$alkyl more preferably $C_1$-$C_4$alkyl, and polar group is as described above within the above given meanings and preferences;

in a more preferred embodiment the polar group is preferably a nitrile group in the terminal position of the alkyl chain, and $x_1$ is 1, especially more preferred is a straight-chain or branched $C_1$-$C_{12}$alkyl group having a terminal polar group, wherein polar group is a nitrile group, and D represents unsubstituted or substituted diamine, acrylate, methacrylate, siloxane silane, maleinimide, preferably diamine, preferably an unsubstituted or substituted diamine, acrylate, methacrylate, siloxane silane, maleinimide, preferably diamine, preferably an optionally substituted aliphatic, aromatic or alicyclic diamine group having from 1 to 40 carbon atoms, represented by formula (III) and is most preferably selected from the following group of structures: substituted or unsubstituted o-phenylenediamine, p-phenylenediamine, m-phenylenediamine, aminophenylen-$Z^4$-phenylenamino; or m-phenylenediamine with a substituted or unsubstituted straight-chain or branched $C_1$-$C_{20}$alkylene group, in which one or more —C—, —CH—, —CH$_2$— group may independently from each other be replaced by a non-aromatic, aromatic, unsubstituted or substituted carbocyclic or heterocyclic group, or a heteroatom and/or by a bridging group; wherein $Z^4$ has the above given meaning; benzidine, diaminofluorene, 3,4-diaminobenzoic acid, 3,4-diaminobenzyl alcohol dihydrochloride, 2,4-diaminobenzoic acid, L-(+)-threo-2-amino-1-(4-aminophenyl)-1,3-propanediol, p-aminobenzoic acid, [3,5-3h]-4-amino-2-methoxybenzoic acid, L-(+)-threo-2-(N,N-dimethylamino)-1-(4-aminophenyl)-1,3-propanediol, 2,7-diaminofluorene, 4,4'-diaminooctafluorobiphenyl, 3,3'-diaminobenzidine, 2,7-diamine-9-fluorenone, 3,5,3',5'-tetrabromo-biphenyl-4,4'-diamine, 2,2'-dichloro[1,1'-biphenyl]-4,4'-diamine, 3,9-diamine-1,11-dimethyl-5,7-dihydro-dibenzo(a,c)cyclohepten-6-one, dibenzo(1,2) dithiine-3,8-diamine, 3,3'-diaminobenzophenone, 3,3'-diaminediphenylmethane, 4,4-bis-(3-amino-4-hydroxyphenyl)-valeric acid, 2,2-bis(3-amino-4-hydroxyphenyl)hexafluoropropane, 2,2-bis(3-amino-4-methylphenyl)hexafluoropropane, tetrabromo methylenedianiline, 2,7-diamine-9-fluorenone, 2,2-bis(3-aminophenyl)hexafluoropropane, bis-(3-amino-4-chlorophenyl)-methanone, bis-(3-amino-4-dimethylamino-phenyl)-methanone, 3-[3-amino-5-(trifluoromethyl)benzyl]-5-(trifluoromethyl)aniline, 1,5-diaminonaphthalene, benzidine-3,3'-dicarboxylic acid, 4,4'-diamino-1,1'-binaphthyl, 4,4'-diaminediphenyl-3,3'-diglycolic acid, dihydroethidium, o-dianisidine, 2,2'-dichloro-5,5'-dimethoxybenzidine, 3-methoxybenzidine, 3,3'-dichlorobenzidine (diphenyl-d6), 2,2'-bis(trifluoromethyl)benzidine, 3,3'-bis (trifluoromethyl)benzidine, 3,3'-dichlorobenzidine-d6, tetramethylbenzidine, di-(aminophenyl)alkylen and from amino compounds listed below, which do not carry two amino groups and are taken as derivatives with at least one additional amino group: aniline, 4-amino-2,3,5,6-tetrafluorobenzoic acid, 4-amino-3,5-diiodobenzoic acid, 4-amino-3-methylbenzoic acid, 4-amino-2-chlorobenzoic acid, 4-aminosalicylic acid, 4-aminobenzoic acid, 4-aminophthalic acid, 1-(4-aminophenyl)ethanol, 4-aminobenzyl alcohol, 4-amino-3-methoxybenzoic acid, 4-aminophenyl ethyl carbinol, 4-amino-3-nitrobenzoic acid, 4-amino-3,5-dinitrobenzoic acid, 4-amino-3,5-dichlorobenzoic acid, 4-amino-3-hydroxybenzoic acid, 4-aminobenzyl alcohol hydrochloride, 4-aminobenzoic acid hydrochloride, pararosaniline base, 4-amino-5-chloro-2-methoxybenzoic acid, 4-(hexafluoro-2-hydroxyisopropyl)aniline, piperazine-p-amino benzoate, 4-amino-3,5-dibromobenzoic acid, isonicotinic acid hydrazide p-aminosalicylate salt, 4-amino-3,5-diiodosalicylic acid, 4-amino-2-methoxybenzoic acid, 2-[2-(4-aminophenyl)-2-hydroxy-1-(hydroxymethyl)ethyl]isoindoline-1,3-dione, 4-amino-2-nitrobenzoic acid, ethyl 2-(4-aminophenyl)-3,3,3-trifluoro-2-hydroxypropanoate, ethyl 2-(4-amino-3-methylphenyl)-3,3,3-trifluoro-2-hydroxypropanoate, ethyl 2-(4-amino-3-methoxyphenyl)-3,3,3-trifluoro-2-hydroxypropanoate, 4-aminonaphthalene-1,8-dicarboxylic acid, 4-amino-3-chloro-5-methylbenzoic acid, 4-amino-2,6-dimethylbenzoic acid, 4-amino-3-fluorobenzoic acid, 4-amino-5-bromo-2-methoxybenzenecarboxylic acid, 3,3'-tolidine-5-sulfonic acid, or their derivatives, again with the proviso that compounds listed which do not carry two amino groups are taken as derivatives with at least one additional amino group, and E represents a with flour, chlor, methoxy or trifluoromethyl substituted or unsubstituted phenylene, a single bond, —O—, —OCO—, —COO—, —OOC—, —NHCO—, —CONH—, —CONR$^2$—, —NR$^2$CO, —SCS, —CO—, $S^1$ is a single bond, a non-aromatic, aromatic, unsubstituted or substituted carbocyclic or heterocyclic group or —(CH$_2$)$_{n1}$—, —(CH$_2$)$_{n1}$—O—(CH$_2$)$_{n1}$—, —(CH$_2$)$_{n1}$—O(OC)—(CH$_2$)$_{n1}$—, —(CH$_2$)$_{n1}$—(OC)O—(CH$_2$)$_{n1}$—, —(CH$_2$)$_{n1}$—NH—(CH$_2$)$_{n1}$—, —(CH$_2$)$_{n1}$—NH(OC)—(CH$_2$)$_{n1}$—, —(CH$_2$)$_{n1}$—(OC)NH—(CH$_2$)$_{n1}$—, —(CH$_2$)$_{n1}$—S—(CH$_2$)$_{n1}$—, —(CH$_2$)$_{n1}$—S(SC)—(CH$_2$)$_{n1}$—, —(CH$_2$)$_{n1}$—(SC)NH—(CH$_2$)$_{n1}$—, —(CH$_2$)$_{n1}$—NH(CS)—(CH$_2$)$_{n1}$—, —(CH$_2$)$_{n1}$—(SC)S—(CH$_2$)$_{n1}$—, —(CH$_2$)$_{n1}$—NHCONH—(CH$_2$)$_{n1}$—, —(CH$_2$)$_{n1}$—NHCSNH—(CH$_2$)$_{n1}$—, —(CH$_2$)$_{n1}$—O(CO)O—(CH$_2$)$_{n1}$—, —(CH$_2$)$_{n1}$—OCONH—(CH$_2$)$_{n1}$—, —(CH$_2$)$_{n1}$—NHOCO—(CH$_2$)$_{n1}$—, wherein n1 is independently from each other is 0, 1, 2, 3, 4, 5, 6, 7, 8, 9, 10, 11, 12 and preferably 0, 1, 2, 3, 4, 5, 6, and more preferably 0, 1, 2, 3, 4 and most preferably 0, 1 or 2, $S^2$ is a single bond, straight-chain or branched, substituted or unsubstituted $C_1$-$C_8$alkylen, more especially $C_1$-$C_6$alkylen, most especially $C_1$-$C_4$alkylen; within the above-given preferences; in which one or more, preferably non-adjacent, —C—, —CH—, —CH$_2$— group may be unreplaced or at least once replaced by an unsubstituted or substituted alicyclic group, preferably cyclohexylen, or an unsubstituted or substituted aromatic group, single bond, heteroatom, —O—, —CO, -arylen-, —CO—O—, —O—CO—, —O—CO—O—; and more preferably
by an unsubstituted or substituted cyclohexylen, or an unsubstituted or substituted phenylen, single bond, —O—, —CO, -arylen-, —CO—O—, —O—CO—, —O—CO—O— and wherein:

with the proviso that oxygen atoms of linking groups are not directly linked to each other,
n is 1 or 2, and n1 is 1, or 2, preferably 1;
with the proviso that if n is 2 or 3 each A, B, $x_1$, D, E, $S^1$, $S^2$, X, Y may be identical or different; and if n1 is 2 each B, $x_1$ is identical or different.

Another preferred embodiment of the present invention relates to a diamine compound represented by one of the general formula (I), referring to any of the preceding definitions, and preferably to alignment materials comprising this diamine compound wherein A represents 1,4-phenylene, which is unsubstituted or mono- or poly-substituted by a halogen atom, and/or by acryloyloxy or methacryloyloxy, trifluormethyl, and/or by an alkoxy, alkylcarbonyloxy or an alkyloxycarbonyl group, having from 1 to 10 carbon atoms, or A is a single bond, —OCO—, —COO—, —OOC—, —NHCO—, —CONH—, —CONR$^2$—, —NR$^2$CO, —SCS, —CO—, wherein $R^2$ and $R^3$ are independently from each other hydrogen or a cyclic, straight-chain or branched, substituted or unsubstituted $C_1$-$C_{24}$alkyl, wherein one or more —C—, —CH—, —CH$_2$— group(s) may be independently from each other replaced by a linking group, and with the proviso that at least one of $R^2$ and $R^3$ is not hydrogen;
and
wherein the compound residue (Ia) of compound of formula (I) as described above

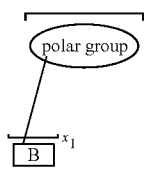

(Ia)

represents —CN, -halogen, especially chloro and/or fluor, —O—$C_1$-$C_5$alkoxy, a straight-chain or branched —O—$C_1$-$C_{16}$alkyl-O—$C_1$-$C_{16}$alkyl, a straight-chain or branched —O—$C_1$-$C_{16}$alkyl-Cl, a straight-chain or branched —O—$C_1$-$C_{16}$alkyl-≡, a straight-chain or branched —O—$C_1$-$C_{16}$alkyl-≡-$C_1$-$C_6$alkyl, phenylene, —N($C_1$-$C_6$alkyl)$_2$, a straight-chain or branched $C_1$-$C_{16}$alkyl-(polar group) group, especially a —O—$C_1$-$C_{16}$alkyl-(polar group) group, —NH—$C_1$-$C_{16}$alkyl-(polar group) group, —OOC—$C_1$-$C_{16}$alkyl-(polar group) group, —OCO—$C_1$-$C_{16}$alkyl-(polar group) group, —OCOO—$C_1$-$C_{16}$alkyl-(polar group) group, —NHCO—$C_1$-$C_{16}$alkyl-(polar group) group, —OCNH—$C_1$-$C_{16}$alkyl-(polar group) group, wherein $C_1$-$C_{16}$alkyl is preferably $C_1$-$C_6$alkyl more preferably $C_1$-$C_4$alkyl, and polar group is as described above within the above given meanings and preferences;
in a more preferred embodiment the polar group is preferably a nitrile group in the terminal position of the alkyl chain, and $x_1$ is 1,
especially more preferred is a straight-chain or branched $C_1$-$C_{12}$alkyl group having a terminal polar group, wherein polar group is a nitrile group, and D represents unsubstituted or substituted diamine, acrylate, methacrylate, siloxane silane, maleinimide, preferably diamine, preferably an unsubstituted o-phenylenediamine, p-phenylenediamine, m-phenylenediamine, biphenyldiamine, aminophenylen-$Z^4$-phenylenamino, naphthylenediamine, or a m-phenylenediamine with a substituted or unsubstituted straight-chain or branched $C_1$-$C_{20}$alkylene group, in which one or more —C—, —CH—, —CH$_2$— group may independently from each other be replaced by a non-aromatic, aromatic, unsubstituted or substituted carbocyclic or heterocyclic group, or a heteroatom and/or by a bridging group;
wherein
$Z^4$ is as defined above;

E represents an unsubstituted or substituted phenylene, a single bond, —O—, —OCO—, —COO—, —OOC—, —NHCO—, —CONH—, —CONR$^2$—, —NR$^2$CO, —SCS, —CO—, $S^1$ is a single bond, phenylene or
—(CH$_2$)$_{n1}$—, —(CH$_2$)$_{n1}$—O(OC)—(CH$_2$)$_{n1}$—, —(CH$_2$)$_{n1}$—NH(CO)O—(CH$_2$)$_{n1}$—, preferably —(CH$_2$)$_1$—, —(CH$_2$)$_2$—, —(CH$_2$)$_5$—, —(CH$_2$)$_8$—, —O(OC)—(CH$_2$)$_6$—, —O(OC)—(CH$_2$)$_8$—, —(CH$_2$)$_3$—NH(CO)O—(CH$_2$)$_3$—.
wherein n1 is independently from each other is 0, 1, 2, 3, 4, 5, 6, 7, 8, 9, 10, 11, 12 and preferably 0, 1, 2, 3, 4, 5, 6, and more preferably 0, 1, 2, 3, 4 and most preferably 0, 1 or 2, $S^2$ a single bond, straight-chain or branched, substituted or unsubstituted $C_1$-$C_8$alkylen, more especially $C_1$-$C_6$alkylen, most especially $C_1$-$C_4$alkylen; within the above-given preferences; in which one or more, preferably non-adjacent, —C—, —CH—, —CH$_2$— group may be unreplaced or at least once replaced
by an unsubstituted or substituted alicyclic group, preferably cyclohexylen, or an unsubstituted or substituted aromatic group, single bond, heteroatom, —O—, —CO, -arylen-, —CO—O—, —O—CO—, —O—CO—O—; and more preferably
by an unsubstituted or substituted cyclohexylen, or an unsubstituted or substituted phenylen, single bond, —O—, —CO, -arylen-, —CO—O—, —O—CO—, —O—CO—O— and wherein:
with the proviso that oxygen atoms of linking groups are not directly linked to each other;
X, Y are independently from each other hydrogen or nitrile, and
n is 1 or 2, and n1 is 1 or 2 and preferably 1;
with the proviso that if n or n1 is 2 each A, B, $x_1$, D, E, $S^1$ and $S^2$ may be identical or different; and if n1 is 2 each B, $x_1$ is identical or different.

Most preferred embodiment of the present invention relates to unsubstituted or substituted diamine, acrylate, methacrylate, siloxane silane, maleinimide, preferably diamine compounds represented by one of the general formula (I), referring to any of the preceding definitions, and to alignment materials comprising these diamine compounds wherein
$S^2$ is a single bond, straight-chain or branched, substituted or unsubstituted $C_1$-$C_8$alkylen, more especially $C_1$-$C_6$alkylen, most especially $C_1$-$C_4$alkylen; within the above-given preferences; in which one or more, preferably non-adjacent, —C—, —CH—, —CH$_2$— group may be unreplaced or at least once replaced
by an unsubstituted or substituted alicyclic group, preferably cyclohexylen, or an unsubstituted or substituted aromatic group, single bond, heteroatom, —O—, —CO, -arylen-, —CO—O—, —O—CO—, —O—CO—O—; and more preferably by an unsubstituted or substituted cyclohexylen, or an unsubstituted or substituted phenylen, single bond, —O—, —CO, -arylen-, —CO—O—, —O—CO—, —O—CO—O— and wherein:

with the proviso that oxygen atoms of linking groups are not directly linked to each other or is replaced by a group of formula (IV), wherein:

$C^1$ represents substituted or unsubstituted 1,4-phenylene; and $Z^1$, $Z^{1a}$ represent each independently from each other —COO—, —OCO—, —CH$_2$—CH$_2$—, —OCH$_2$—, —CH$_2$O—, —CH=CH—, —C≡C—, —CH=CH—COO—, —OCO—CH=CH—, or a single bond;

$a_1$ represents 1, and $a_3$ represents 0

$S^2$ is linked to A via $Z^1$.

Especially most preferred embodiment of the present invention relates to compounds (I), preferably diamine compounds, of formulae (Ib), (Ic), (Id)

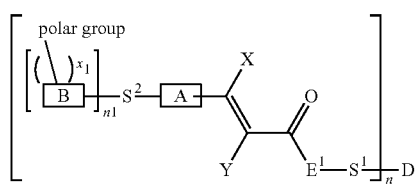

(Ib)

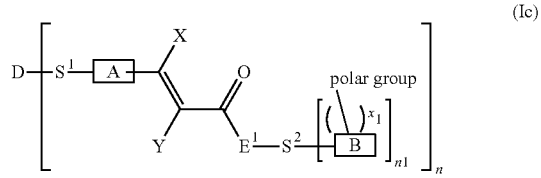

(Ic)

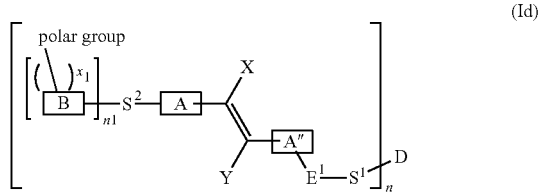

(Id)

wherein polar group, B, x1, $n_1$, n, $S^2$, A, X, Y, $S^1$ and D have the same meanings and preferences as given above, and A' and A" have independently from each other the same meanings and preferences as describe for A in the present invention, and $E^1$ has the same meaning and preferences as given above for E above.

Preferred is (Ib), (Ic), (Id), wherein A represents an unsubstituted or substituted carbocyclic or heterocyclic aromatic group selected from a monocyclic ring of five or six atoms, two adjacent monocyclic rings of five or six atoms, a bicyclic ring system of eight, nine or ten atoms, or a tricyclic ring system of thirteen or fourteen atoms;

more preferred A is unsubstituted or substituted phenanthrylene, naphthylene, biphenylene or phenylene, wherein the preferred substituent(s) is (are) a halogen atom, a hydroxy group and/or by a polar group, wherein the polar group is preferably trifluoromethyl, nitro, nitrile, carboxy; and/or by acryloyloxy, alkylacryl, alkylmethacryl, alkyl(en)acryl, alkyl(en)methacryl, acrylenacryl, methacrylenalkyl, methacryloyloxy, vinyl, vinyloxy, allyl, allyloxy, and/or by a cyclic, straight-chain or branched alkyl, which is unsubstituted, mono- or poly-substituted by fluorine and/or chlorine, having from 1 to 20 carbon atoms, wherein one or more, preferably non-adjacent, —C—, —CH—, —CH$_2$— groups may independently be replaced by a linking group and or an aromatic or an alicyclic group, preferably the linking group is selected from —O—, —CO—, —CO—O—, —O—CO—.

Most preferably A is substituted or unsubstituted naphthylene, biphenylene or phenylene, wherein the preferred substituent(s) is (are) halogen atom, trifluoromethyl, hydroxy group and/or by acryloyloxy, alkylacryl, alkylmethacryl, acrylenacryl, methacrylenalkyl, methacryloyloxy, straight-chain or branched alkyl, alkoxy, alkylcarbonyloxy, and/or alkyloxycarbonyl groups, wherein the alkyl residue has from 1 to 20 carbon atoms.

Especially most preferably is (Ib), (Ic) and (Id), wherein A is at least once substituted or unsubstituted phenylene, preferably 1,4-phenylen, wherein the preferred substituent(s) is (are) a halogen atom, trifluoromethyl, alkoxy, especially methoxy.

In addition, preferred is (Ib), wherein X, Y are independently from each other hydrogen or nitrile, more preferred X and Y are hydrogen, (Ic), wherein X, Y are independently from each other hydrogen or nitrile, more preferred X and Y are hydrogen, (Id), wherein X and Y are independently from each other are hydrogen or nitrile.

Further preferred is (Ib), wherein $S^2$ is a single bond and B is a —CH$_3$ group or a C$_2$alkyl, wherein —CH$_3$ or the —CH$_2$ group is replaced by at least one heteroatom, preferably the —CH$_3$ group is replaced by fluor or chlor and the —CH$_2$ group is replaced by —O—.

More especially most preferred embodiment of the present invention relates to a compound (I), or (I') referring to the below given formula

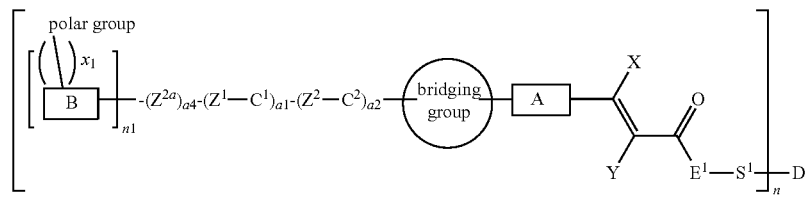

wherein

C$^1$, C$^2$ each independently represents a non-aromatic, aromatic, optionally substituted carbocyclic or heterocyclic group, within the above given meaning and preferences, preferably connected to each other via the bridging groups Z$^1$ and Z$^2$ and/or Z$^{1a}$, preferably C$^1$ and C$^2$ are connected at the opposite positions via the bridging groups Z$^1$ and Z$^2$ and/or Z$^{1a}$, and Z$^1$, Z$^2$, Z$^{2a}$ each independently represents a bridging group, preferably selected from —CH(OH)—, —CH$_2$—, —O—, —CO—, —CH$_2$(CO)—, —SO—, —CH$_2$(SO)—, —SO$_2$—, —CH$_2$(SO$_2$)—, —COO—, —OCO—, —COCF$_2$—, —CF$_2$CO—, —S—CO—, —CO—S—, —SOO—, —OSO—, —SOS—, —CH$_2$—CH$_2$—, —OCH$_2$—, —CH$_2$O—, —CH═CH—, —C≡C—, —CH═CH—COO—, —OCO—CH═CH—, —CH═N—, —C(CH$_3$)═N—, —O—CO—O—, —N═N— and a single bond, a$_1$, a$_2$, a$_4$ each independently represents an integer from 0 to 3, such that a$_1$+a$_2$+a$_4$≤6; preferably a4 and a1 are 0 and a$_2$≤4, preferably 1, or 2, and more preferably preferred is a Z$^2$ a single bond if a2 is 1 and a4 and a1 are 0;

A, B, n1, n, D, E$^1$, S$^1$, x1, polar group, bridging group, X and Y, have the above given meanings and preferences; preferably n1 is 1;

and preferably with the proviso that substituted or unsubstituted phenyl linked by a single bond to A in formula (I) or (I') is excluded.

Further, more especially most preferred embodiment of the present invention relates to diamine, acrylate, methacrylate, siloxane, silane, maleinimide compounds of formulae (VI), (VIa), (VIb), (VIc), (VII), (VIII), (IX), (X), (XI), (XIa), (XIb), (VI'), (VII'), (VIII'), (IX'), (X'), (XI'), (XIa'), (XIb'), (XIc')

(VI)

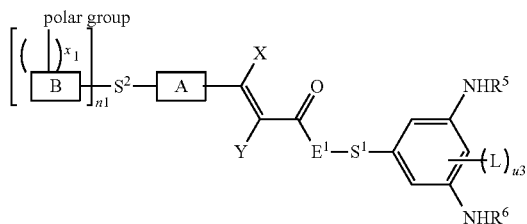

(VIa)

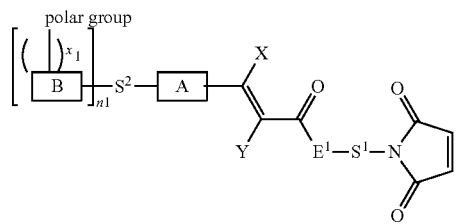

(VIb)

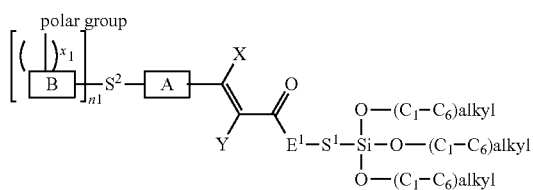

(VIc)

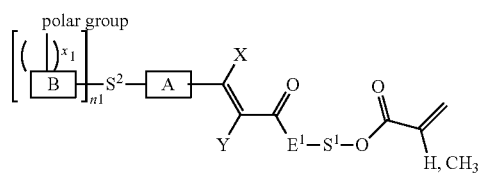

(VII)

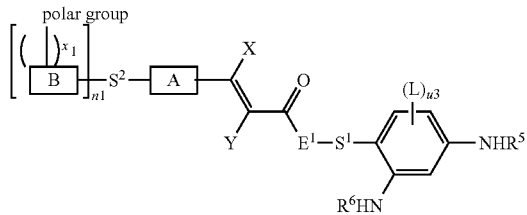

(VIII)

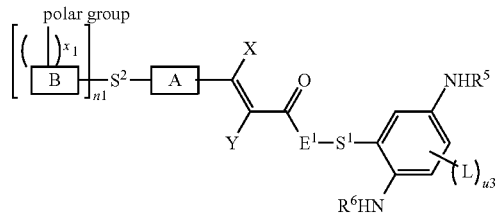

(IX)

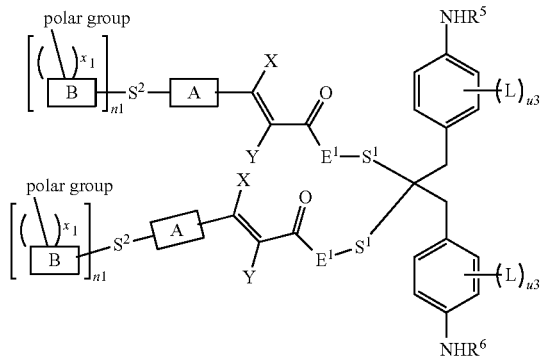

(X)

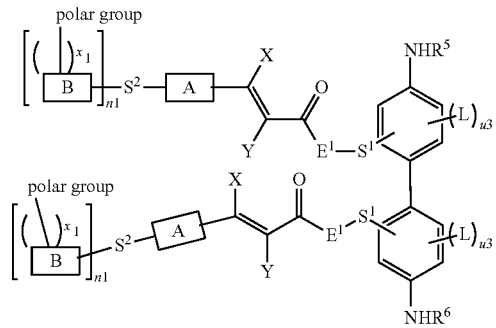

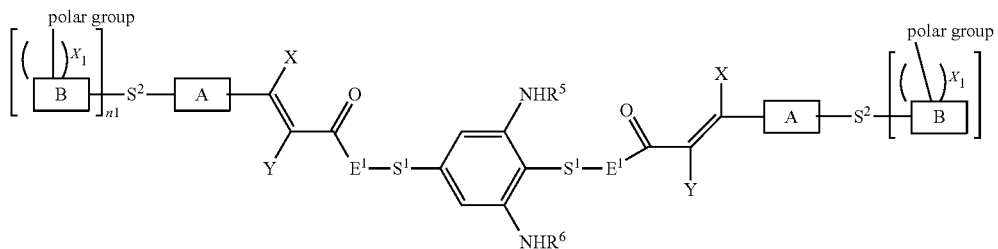
(XI)
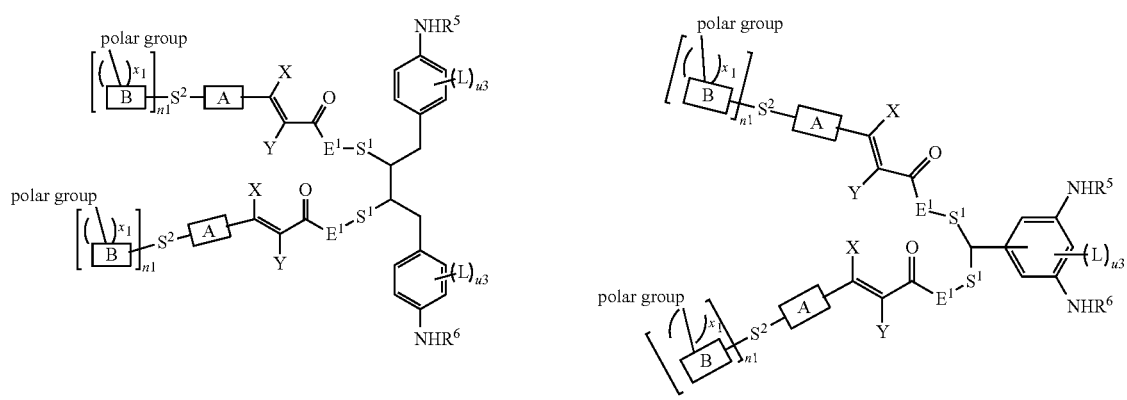
(XIa) (XIb)
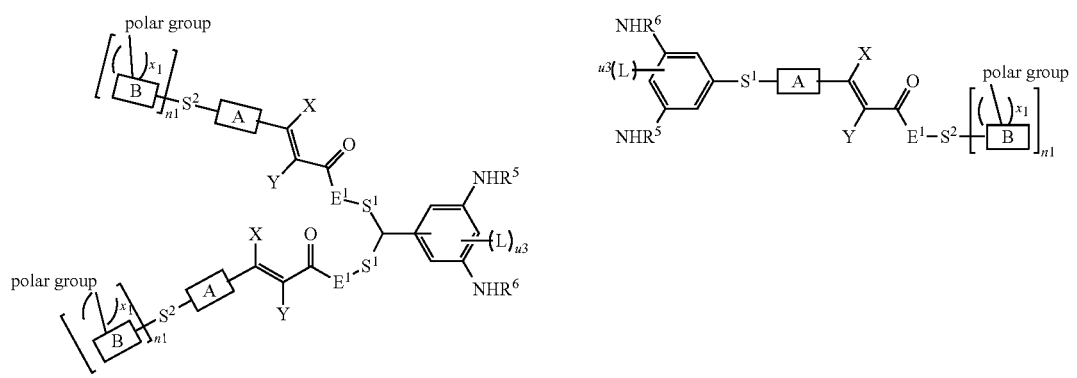
(XIb1) (VI')
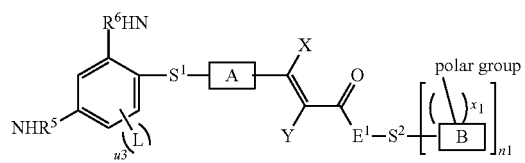
(VII')
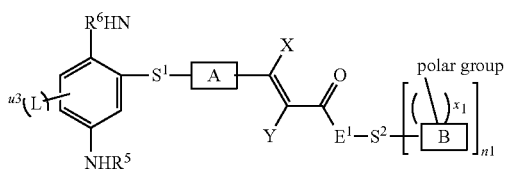
(VIII')

-continued
(IX')
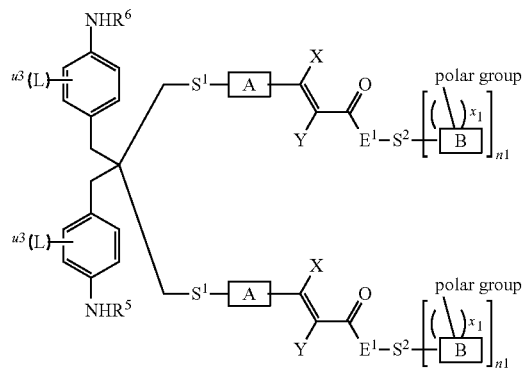
(X')
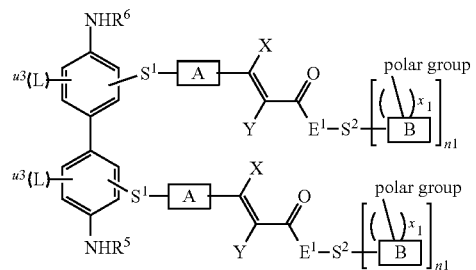
(XI')
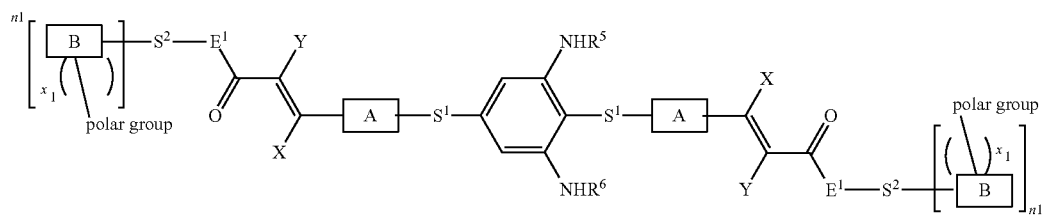
(XIa')
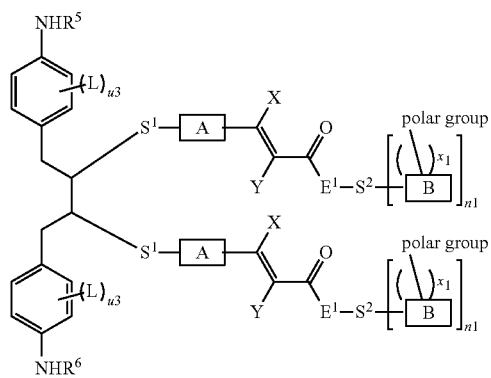
(XIb')
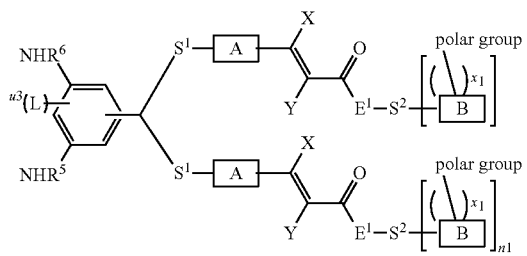
(XIc')
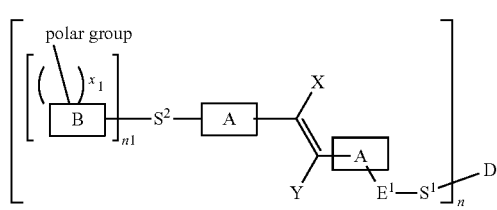

wherein A' and A" have independently from each other the same meanings and preferences as describe for A in the present invention, and wherein A, B, x1, n, n1, D, E, $S^2$, $S^1$, X and Y, $R^5$, $R^6$ and $Z^4$ and polar group have the above given meanings and preferences as given above; preferably n1 is 1;

L is —$CH_3$, —$OCH_3$, —$COCH_3$, nitro, nitrile, halogen, $CH_2$=CH—, $CH_2$=C($CH_3$)—, $CH_2$=CH—(CO)O—, $CH_2$=CH—O—, $CH_2$=C($CH_3$)—(CO)O—, or $CH_2$=C($CH_3$)—O—, u3 is an integer from 0 to 2.

Further, especially most preferred embodiment of the present invention relates to diamine, acrylate, methacrylate, siloxane silane, maleinimide, preferably diamine compounds of formula (XII)

(XII)

wherein $x_1$, n, n1, D, $E^1$, $S^1$, X, Y, $Z^1$, L, $u_1$ and $u_2$ have the above given meanings and preferences.

Preferred compounds of formula (XII) are compounds, wherein $Z^1$ is —COO—, —OCO—, —OCO($C_1$-$C_6$)alkylen or —COO($C_1$-$C_6$)alkylen, or a single bond, or a straight-chain or branched, substituted or unsubstituted $C_1$-$C_8$alkylen, wherein one or more —C—, —CH—, —$CH_2$— group may independently from each other be replaced independently from each other by a linking group, preferably by —O—.

Further, especially most preferred is a compound of formula (XIIa)

(XIIa)

wherein n, n1, D, $E^1$, $S^1$, $Z^1$, L, polar group, $u_1$ and $u_2$ X and Y have the above given meanings and preferences as above, and wherein the following compound residue represents a straight-chain or branched $C_1$-$C_8$alkyl group, having a polar group within the above given meaning and preferences, and $x_1$ is an integer from 1 to 9, B represents a straight-chain or branched $C_1$-$C_8$alkyl group, which is unsubstituted or in addition to its fluorine substituent(s) substituted by di-($C_1$-$C_{16}$alkyl)amino, $C_1$-$C_6$alkyloxy, nitro, nitrile and/or chlorine; and wherein one or more —C—, —CH—, —$CH_2$— group may independently be replaced by a linking group selected from —O—, —CO—, —CO—O—, —O—CO—, —$NR^1$—, —$NR^1$—CO—, —CO—$NR^1$— and —CH=CH—, wherein:

$R^1$ represents a hydrogen atom or $C_1$-$C_6$alkyl;

Another preferred embodiment of the present invention relates to diamine compounds represented by the general formula (I), which may be used in the subsequent manufacturing processes as such or in combination with one or more additional other diamines, preferably those of formula (L) as given below.

The diamine (L) represents an optionally substituted aliphatic, aromatic or alicyclic diamino group having from 1 to 40 carbon atoms and preferably made from or selected from the following group of structures: aniline, p-phenylenediamine, m-phenylenediamine, benzidine, diaminofluorene, or their derivatives, with the proviso that compounds listed which do not carry two amino groups are taken as derivatives with at least one additional amino group, and more preferably made from or selected from the following commercially available amino compounds (example of suppliers: Aldrich, ABCR, ACROS, Fluka) which can also be used as comonomers: 4-amino-2,3,5,6-tetrafluorobenzoic acid 4-amino-3,5-diiodobenzoic acid, 3,4-diaminobenzoic acid 4-amino-3-methylbenzoic acid, 4-amino-2-chlorobenzoic acid 4-aminosalicylic acid 4-aminobenzoic acid 4-aminophthalic acid 1-(4-aminophenyl)ethanol 4-aminobenzyl alcohol 4-amino-3-methoxybenzoic acid 4-aminophenyl ethyl carbinol 4-amino-3-nitrobenzoic acid 4-amino-3,5-dinitrobenzoic acid 4-amino-3,5-dichlorobenzoic acid 4-amino-3-hydroxybenzoic acid 4-aminobenzyl alcohol hydrochloride 4-aminobenzoic acid hydrochloride pararosaniline base 4-amino-5-chloro-2-methoxybenzoic acid 4-(hexafluoro-2-hydroxyisopropyl)aniline piperazine-p-amino benzoate 4-amino-3,5-dibromobenzoic acid isonicotinic acid hydrazide p-aminosalicylate salt 4-amino-3,5-diiodosalicylic acid 4-amino-2-methoxybenzoic acid 2-[2-(4-aminophenyl)-2-hydroxy-1-(hydroxymethyl)ethyl] isoindoline-1,3-dione 4-amino-2-nitrobenzoic acid 2,4-diaminobenzoic acid p-aminobenzoic acid, [3,5-3h]-4-amino-2-methoxybenzoic acid L-(+)-threo-2-amino-1-(4-aminophenyl)-1,3-propanediol L-(+)-threo-2-(N,N-dimethylamino)-1-(4-aminophenyl)-1,3-propanediol ethyl 2-(4-aminophenyl)-3,3,3-trifluoro-2-hydroxypropanoate ethyl 2-(4-amino-3-methylphenyl)-3,3,3-trifluoro-2-hydroxypropanoate ethyl 2-(4-amino-3-methoxyphenyl)-3,3,3-trifluoro-2-hydroxypropanoate 3,4-diaminobenzyl alcohol dihydrochloride 4-aminonaphthalene-1,8-dicarboxylic acid 4-amino-3-chloro-5-methylbenzoic acid 4-amino-2,6-dimethylbenzoic acid 4-amino-3-fluorobenzoic acid 4-amino-5-bromo-2-methoxybenzenecarboxylic acid 2,7-diaminofluorene 4,4'-diaminooctafluorobiphenyl 3,3'-diaminobenzidine 3,3',5,5'-tetramethylbenzidine 3,3'-dimethoxybenzidine o-tolidine 3,3'-dinitrobenzidine 2-nitrobenzidine 3,3'-dihydroxybenzidine o-tolidine sulfone benzidine, 3,3'-dichlorobenzidine 2,2',5,5'-tetrachlorobenzidine, benzidine-3,3'-dicarboxylic acid 4,4'-diamino-1,1'-binaphthyl 4,4'- diaminodiphenyl-3,3'-diglycolic acid dihydroethidium o-dianisidine 2,2'-dichloro-5,5'-dimethoxybenzidine 3-methoxybenzidine 3,3'-dichlorobenzidine (diphenyl-d6), 2,7-diamino-9-fluorenone 3,5,3',5'-tetrabromo-biphenyl-4,4'-diamine 2,2'-bis(trifluoromethyl)benzidine 2,2'-dichloro [1,1'-biphenyl]-4,4'-diamine 3,9-diamino-1,11-dimethyl-5,7-dihydro-dibenzo(a,c)cyclohepten-6-one 3,3'-bis(trifluoromethyl)benzidine dibenzo(1,2)dithiine-3,8-diamine 3,3'-tolidine-5-sulfonic acid 3,3'-dichlorobenzidine-d6 tetramethylbenzidine 3,3'-diaminobenzophenone, 3,3'-diaminodiphenylmethane, 4,4-bis-(3-amino-4-hydroxyphenyl)-valeric acid 2,2-bis(3-amino-4-hydroxyphenyl)hexafluoropropane 2,2-bis(3-amino-4-methylphenyl)hexafluoropropane tetrabromo methylenedianiline 2,7-diamino-9-fluorenone 2,2-bis(3-aminophenyl)hexafluoropropane bis-(3-amino-4-chlorophenyl)-methanone bis-(3-amino-4-dimethylamino-phenyl)-methanone 3-[3-amino-5-(trifluoromethyl)benzyl]-5-(trifluoromethyl)aniline 1,5-diaminonaphthalene or their derivatives, again with the proviso that compounds listed which do not carry two amino groups are taken as derivatives with at least one additional amino group.

Preferred examples of additional other diamines (L) are: ethylenediamine, 1,3-propylenediamine, 1,4-butylenediamine, 1,5-pentylenediamine, 1,6-hexylenediamine, 1,7-heptylenediamine, 1,8-octylenediamine, 1,9-nonylenediamine, 1,10-decylenediamine, 1,11-undecylenediamine, 1,12-dodecylenediamine, α,α'-diamino-m-xylene, α,α'-diamino-p-xylene, (5-amino-2,2,4-trimethylcyclopentyl) methylamine, 1,2-diaminocyclohexane, 4,4'-diaminodicyclohexylmethane, 1,3-bis(methylamino)cyclohexane, 4,9-dioxadodecane-1,12-diamine, 3,5-diaminobenzoic acid methyl ester, 3,5-diaminobenzoic acid hexyl ester, 3,5-diaminobenzoic acid dodecyl ester, 3,5-diaminobenzoic acid isopropyl ester, 4,4'-methylenedianiline, 4,4'-ethylenedianiline, 4,4'-diamino-3,3'-dimethyldiphenylmethane, 3,3',5,5'-tetramethylbenzidine, 4,4'-diaminodiphenyl sulfone, 4,4'-diaminodiphenyl ether, 1,5-diaminonaphthalene, 3,3'-dimethyl-4,4'-diaminobiphenyl, 3,4'-diaminodiphenyl ether, 3,3'-diaminobenzophenone, 4,4'-diaminobenzophenone, 4,4'-diamino-2,2'-dimethylbibenzyl, bis[4-(4-aminophenoxy)phenyl]sulfone, 1,4-bis(4-aminophenoxy)benzene, 1,3-bis(4-aminophenoxy)benzene, 1,3-bis(3-aminophenoxy)benzene, 2,7-diaminofluorene, 9,9-bis(4-aminophenyl)fluorene, 4,4'-methylenebis(2-chloroaniline), 4,4'-bis(4-aminophenoxy)biphenyl, 2,2',5,5'-tetrachloro-4,4'-diaminobiphenyl, 2,2'-dichloro-4,4'-diamino-5,5'-dimethoxybiphenyl, 3,3'-dimethoxy-4,4'-diaminobiphenyl, 4,4'-(1,4-phenyleneisopropylidene)bisaniline, 4,4'-(1,3-phenyleneisopropylidene)bisaniline, 2,2-bis[4-(4-aminophenoxy)phenyl]propane, 2,2-bis[3-(4-aminophenoxy)phenyl] hexafluoropropane, 2,2-bis[3-amino-4-methylphenyl] hexafluoropropane, 2,2-bis(4-aminophenyl) hexafluoropropane, 2,2'-bis[4-(4-amino-2-trifluoromethylphenoxy)phenyl]hexafluoropropane, 4,4'-diamino-2,2'-bis(trifluoromethyl)biphenyl, and 4,4'-bis[(4-amino-2-trifluoromethyl)phenoxy]-2,3,5,6,2',3',5',6'-octafluorobiphenyl; as well as diamines (L) disclosed in U.S. Pat. No. 6,340,506, WO 00/59966 and WO 01/53384, all of which are explicitly incorporated herein by reference;

The diamine compounds (L) according to the present invention may be prepared using methods that are known to a person skilled in the art.

In addition, preferred diamines (L) are the commercially available ones listed below: Polymers Poly(3,3',4,4'-benzophenonetetracarboxylic dianhydride-co-4,4'-oxydianiline/1,3-phenylenediamine), amic acid solution Poly(3,3',4,4'-benzophenonetetracarboxylic dianhydride-co-4,4'-oxydianiline/1,3-phenylenediamine), amic acid solution Poly(pyromellitic dianhydride-co-4,4'-oxydianiline), amic acid solution Aromatic diamine 2,7-diaminofluorene 1,5-diaminoanthraquinone 2,6-diaminoanthraquinone pararosaniline hydrochloride 3,6-acridinediamine 4,4'-diaminooctafluorobiphenyl 2,2'-dithiodianiline 3,3',5,5'-tetramethylbenzidine 3,3'-diaminodiphenyl sulfone 4,4'-diamino-2,2'-dimethylbibenzyl 4,4'-diaminodiphenyl ether 4,4'-dithiodianiline 4,4'-diaminodiphenyl sulfone 4,4'-diaminodiphenylmethane 4,4'-ethylenedianiline 3,3'-dimethoxybenzidine 2,2'-dithiobis(1-naphthylamine) 3,7-diamino-2-methoxyfluorene 3,6-diamino-10-methylacridinium chloride propidium iodide o-dianisidine dihydrochloride 2,7-diaminofluorene dihydrochloride pararosaniline acetate 3,6-diamino-10-methylacridinium chloride hydrochloride proflavine dihydrochloride o-tolidine dihydrochloride 3,3',5,5'-tetramethylbenzidine dihydrochloride 3,3'-diaminobenzidine tetrahydrochloride 4,4'-diaminostilbene dihydrochloride 4,4'-diaminodiphenylamine sulfate proflavine hemisulfate 2,2'-ethylenedianiline diphosphate 1,5-diamino-4,8-dihydroxyanthraquinone o-tolidine 3,3'-diaminobenzophenone 3,3'-diaminodiphenylmethane 3,4'-diaminodiphenylmethane 2,2-bis[4-(4-aminophenoxy)phenyl]hexafluoropropane 4,4'-diamino-1,1'-dianthramide 3,3'-dinitrobenzidine 4,4'-diamino-5,5'-dimethyl-2,2'-biphenyldisulfonic acid 4,4'-diaminostilbene-2,2'-disulfonic acid 3-amino-4-hydroxyphenyl sulfone 4,4-bis-(3-amino-4-hydroxyphenyl)-valeric acid 2,2'-diamino-4,4'-difluorobibenzyl 2-amino-4-chlorophenyl disulfide 3,3'-(decamethylenedioxy)dianiline 3,3'-(pentamethylenedioxy) dianiline 4-(p-aminoanilino)-3-sulfoaniline 4-[3-(4-aminophenoxy)propoxy]aniline 2-nitrobenzidine benzidine-3-sulfonic acid 4,4'-diaminodiphenyl sulfide 4,4'-diaminobenzanilide n,n'-bis(3-aminophenylsulfonyl) ethylenediamine 2,2'-biphenyldiamine 3,4'-diaminodiphenyl ether proflavine hemisulphate phenosafranin 4,4'-diaminobenzophenone 2,2-bis(4-aminophenyl)hexafluoropropane 2,2-bis(3-amino-4-hydroxyphenyl)hexafluoropropane 2,2-bis(3-amino-4-methylphenyl) hexafluoropropane 3,3'-dihydroxybenzidine 3,3'-diamino-4,4'-dihydroxybiphenyl 4,4'-bis(4-aminophenoxy)biphenyl 2,2-bis[4-(4-aminophenoxy)phenyl]propane 1,4-bis(4-aminophenoxy)benzene 1,3-bis(4-aminophenoxy)benzene bis[4-(4-aminophenoxy)phenyl]sulfone 9,9-bis(4-aminophenyl)fluorene o-tolidine sulfone benzidine 3,3'-dichlorobenzidine dihydrochloride benzidine dihydrochloride 3,6-thioxanthenediamine-10,10-dioxide 4,4'-diamino-2,2'-biphenyldisulfonic acid 4,4'-azodianiline 2,5-bis-(4-aminophenyl)-(1,3,4)oxadiazole 3,3'-dimethylnaphthidine benzidine sulfate 1,3-bis(3-aminophenoxy)benzene 3,3'-dichlorobenzidine 2,2',5,5'-tetrachlorobenzidine 4,4'-diamino-1,1'-binaphthyl diamine bordeaux benzoflavin chrysaniline 2,2'-thiobis(5-aminobenzenesulfonic acid) 4,4'-methylenebis(2-chloroaniline) tetrabromo methylenedianiline 4,4'-diamino-3,3'-dinitrodiphenyl ether benzidine pyrophosphate 3,6-diaminothioxanthene-10-dioxide, dihcl 4,4''-diamino-p-terphenyl 1,8-diamino-4,5-dihydroxyanthraquinone bis(p-aminophenoxy)dimethylsilane bis[4-(3-aminophenoxy)phenyl]sulfone 4,4'-methylenedi-2,6-xylidine 2-aminobenzaldehyde-ethylene-diimine 3-methylbenzidine dihydrochloride 3,3'-diethylbenzidine dihydrochloride 3,6-diaminoacridine hydrochloride 4,4'-diamino-5,5'-dimethyl-2,2'-biphenyl disulfonic acid disodium salt 4,4'-methylenebis(3-chloro-2,6-diethylaniline) 4,4'-methylene-bis-(2,6-diethylaniline) 4,4'-methylenebis-(2,6-diisopropylaniline) toluylenediamine 3,8-diamino-6-phenylphenanthridine thionin perchlorate dihydroethidium thionin 4,4-diamino benzene sulfonyl anilide o-dianisidine hcl 2,2'-dichloro-5,5'-dimethoxybenzidine 3-methoxybenzidine 2,2'-(hexamethylenedioxy)dianiline 2,2'-(pentamethylenedioxy)dianiline 2,2'-(ethylenedioxy)dianiline 4-[4-(4-aminophenoxy)butoxy]aniline 2,2'-diamino-4'-methoxy-4-methylbenzanilide 5,5'-dimethyl-2,2'-dinitrobenzidine n,n'-bis(2-aminophenyl)-1,3-propanediamine 3,4'-diaminochalcone 2,3',4,5',6-pentaphenyl-3,4'-biphenyldiamine 2-([1-(4-(1-[(2-aminophenyl)thio]-2-nitroethyl)phenyl)-2-nitroethyl]thio)anilin 2-((2-[(2-aminophenyl)thio]ethyl)thio)aniline 2-((4-[(2-aminophenyl)thio]but-2-enyl)thio)aniline 4,4'-diamino-3,3'-dimethyldiphenyl methane 2,2'-diamino-bibenzyl trimethylene bis(4-aminobenzoate) fluoresceinamine benzidines mixture 3-nitro-4,4'-methylenedianiline 4,4-diamino-2,2'-dichlorodiphenyl disulfide 1,6-diaminopyrene 1,8-diaminopyrene 3,6-diaminocarbazole 4,4'(5')-diamino-[2,4]-dibenzo-18-crown-6,dihydrochloride 4,4'-diaminostilbene-2,2'-disulfonic acid, disodium salt (r)-(+)-2,2'-diamino-1,1'-binaphthyl proflavine hemisulfate dihydrate 3,6-diaminoacridine hemisulfate hemihydrate dimidium bromide monohydrate o-tolidine dihydrochloride hydrate 3,3',5,5'-tetramethylbenzidine dihydrochloride hydrate 3,3'-diaminobenzidine tetrahydrochloride dihydrate 3,6-[bis(4-amino-3-(sodiumsulphonato)phenlamino)]-2,5-dichloro 4-benzoquinone 2,2'-dimethylbenzidine hydrochloride 2,2'-(phenylmethylenebis)bis(4-methylaniline) 3,4'-diaminobiphenyl 2,7-diamino-9-fluorenone n,n'-bis(2-aminophenyl) oxamide 2-[2-(2-aminophenyl)diaz-1-enyl]aniline 3,5,3',5'-tetrabromo-biphenyl-4,4'-diamine n,n'-bis(4-aminophenyl)-1,3-bis(aminomethyl)benzene dihydrochloride 4',4"(5")-diaminodibenzo-15-crown-5 2,2'-bis(trifluoromethyl)benzidine bis(4-amino-2,3-dichlorophenyl)methane alpha, alpha'-bis(4-aminophenyl)-1,4-diisopropylbenzene 2,2-bis(3-aminophenyl)hexafluoropropane 3,10-diamino-6,13-dichlorobenzo[5,6][1,4]oxazino[2,3-b]phenoxazine-4,11-disulfo n1-(2-amino-4-methylphenyl)-2-aminobenzamide n1-(2-amino-4-chlorophenyl)-2-aminobenzamide 2,2'-dichloro[1,1'-biphenyl]-4,4'-diamine 4,4'(5')-diaminodibenzo-15-crown-5 dihydrochloride rcl s19,413-1 bis-(4-amino-3-nitro-phenyl)-methanone bis-(3-amino-4-chloro-phenyl)-methanone bis-(3-amino-4-dimethylamino-phenyl)-methanone n,n'-bis-(4-amino-2-chloro-phenyl)-isophthalamide n,n'-bis-(4-amino-2-chloro-phenyl)-terephthalamide 3,9-diamino-1,11-dimethyl-5,7-dihydro-dibenzo(a,c)cyclohepten-6-one 2-aminobenzaldehyde n-[(z)-(2-aminophenyl)methylidene]hydrazone 3,3'-bis(trifluoromethyl)benzidine dicarboxidine 2 hcl 4,4'-(1,3-phenylenediisopropylidene)bisaniline 1,4-phenylenebis[[4-(4-aminophenoxy)phenyl]methanone]2-((5-[(2-aminophenyl)thio]-3,4-dinitro-2-thienyl)thio)aniline n'1-(2-aminobenzoyl)-2-aminobenzene-1-carbohydrazide 2-[4-(5-amino-1h-benzimidazol-2-yl)phenyl]-1h-benzimidazol-5-amine 4-[4-(4-aminophenoxy)-2,3,5,6-tetrafluorophenoxy] aniline 3,3'-dinitro-4,4'-diaminodiphenyl sulfone 3,3',4,4'-tetraaminodiphenylsulfone 4-[1-(4-aminophenyl)-1-methylethyl]aniline 3,3-diamino diphenyl urea bis(4-aminophenyl)acetylene dibenzo(1,2)dithiine-3,8-diamine ethidium homodimer-2 4,4'-bis-(2-aminobenzenesulfonyl) bis-phenolester neopentyl glycol bis(4-aminophenyl) ether 2,2'-oxydianiline 4,4'-diaminodiphenylamine-2,2-disulphonic acid 4,4-diamino diphenyl urea 3,3'-tolidine-5-sulfonic acid n1-(3-[(2-aminobenzoyl)amino]propyl)-2-aminobenzamide 2-((6-[(2-aminophenyl)sulfanyl]-5-nitro-2-pyridyl)sulfanyl)aniline 2-((6-amino-1,3-benzothiazol-2-yl) dithio)-1,3-benzothiazol-6-ylamine tetramethylbenzidine 2-([6-[(2-aminophenyl)sulfanyl]-3,5-di(trifluoromethyl)-2-pyridyl]sulfanyl) anil 3,6-diaminothioxanthene-10-dioxide dihydrochloride m-tolidine dihydrochloride hydrate 2-amino-n-[2-amino-4-(trifluoromethyl)phenyl]-5-methyl-benzamide 2-([2-[(2-aminophenyl)thio]-6-nitro-4-(trifluoromethyl)phenyl]thio)aniline 2-[(3-([(2-aminophenyl)thio]methyl)-2,4,6-trimethylbenzyl)thio]aniline 3-[3-amino-5-(trifluoromethyl)benzyl]-5-(trifluoromethyl)aniline 2-((5-[(2-aminophenyl)thio]-4-chloro-2-nitrophenyl)thio)aniline 4-(1-(4-aminophenyl)-2-[4-(dimethylamino)phenyl]vinyl) aniline 1,5-bis(4-aminophenoxy)pentane 2,3'-dichlorobenzidine dihydrochloride 3,3'-diamono-4,4'-dichlorodiphenyl sulfone 3-(bis-(4-amino-phenyl)-methyl)-2,3-dihydro-isoindol-1-one 4,4-diamino diphenyl-2-sulphonic acid 4,4'-diamino-diphenylene-cycylohexane 4,5'-diamino-(1,1')bianthracenyl-9,10,9',10'-tetraone Alicyclic diamines 4,4'-methylenebis(cyclohexylamine) 4,4'-methylenebis(2-methylcyclohexylamine) Aliphatic diamines 1,8-diamino-p-menthane 4,4'-methylenebis(cyclohexylamine) d-cystine l-cystine dimethyl ester dihydrochloride neamine bis(2-aminopropyl)amine (h-cys-beta-na)2 2 hcl l-cystine dibenzyl ester ditosylate 1,4-diaminocyclohexane (h-cys-pna)2 dl-2-aminopropionic anhydride l-cystine(di-b-naphthylamide)hydrochloride l-cystine-bis-p-nitroanilide dihydrobromide l-cystine diethyl ester dihydrochloride trans-1,4-cyclohexanediamine 4,4'-methylenebis(2-methylcyclohexylamine) l-leucinethiol, oxidized dihydrochloride 1,3-diaminoadamantane dihydrochloride l-leucinethiol disulfide 2 hcl l-cystine disodium salt, monohydrate l-homocystine methylester hydrochloride 1,3-adamantanediamine tetracyclo[8.2.1.1(8,11).0(2,7)]tetradeca-2,4,6-triene-10,11-diamine tricyclo[3.3.1.0(3,7)]nonane-3,7-diamine From the class of commercially available diamines (L) preferred are the below listed ones: Alicyclic diamines 4,4'-methylenebis(cyclohexylamine) 4,4'-methylenebis(2-methylcyclohexylamine) Aliphatic diamines 4,4'-methylenebis(cyclohexylamine) 1,4-diaminocyclohexane trans-1,4-cyclohexanediamine 4,4'-methylenebis(2-methylcyclohexylamine) 1,3-adamantanediamine Aromatic diamines 2,7-diaminofluorene 2,6-diaminoanthraquinone 4,4'-diaminooctafluorobiphenyl 4,4'-diaminodiphenyl ether 4,4'-dithiodianiline 4,4'-diaminodiphenylmethane 4,4'-ethylenedianiline 3,3'-dimethoxybenzidine o-tolidine 3,3'-diaminobenzophenone 3,3'-diaminodiphenylmethane 3,4'-diaminodiphenylmethane 2,2-bis[4-(4-aminophenoxy)phenyl]hexafluoropropane 4-[3-(4-aminophenoxy)propoxy]aniline 4,4'-diaminodiphenyl sulfide 4,4'-diaminobenzophenone 2,2-bis(4-aminophenyl)hexafluoropropane 4,4'-bis(4-aminophenoxy)biphenyl 2,2-bis[4-(4-aminophenoxy)phenyl]propane 1,4-bis(4-aminophenoxy)benzene 1,3-bis(4-aminophenoxy)benzene bis[4-(4-aminophenoxy)phenyl] sulfone 9,9-bis(4-aminophenyl)fluorene benzidine 4,4'-azodianiline 1,3-bis(3-aminophenoxy)benzene 4,4'-diamino-1,1'-binaphthyl 4,4"-diamino-p-terphenyl bis(p-aminophenoxy)dimethylsilane 4-[4-(4-aminophenoxy)butoxy]aniline 3,4'-diaminochalcone trimethylene bis(4-aminobenzoate) 3,4'-diaminobiphenyl 2,7-diamino-9-fluorenone 4',4"(5")-diaminodibenzo-15-crown-5 2,2'-bis(trifluoromethyl)benzidine alpha,alpha'-bis(4-aminophenyl)-1,4-diisopropylbenzene 3,3'-bis(trifluoromethyl)benzidine 4,4'-(1,3-phenylenediisopropylidene)bisaniline 1,4-phenylenebis[[4-(4-aminophenoxy)phenyl]methanone]4-[4-(4-aminophenoxy)-2,3,5,6-tetrafluorophenoxy]aniline 4-[1-(4- aminophenyl)-1-methylethyl]aniline neopentyl glycol bis(4-aminophenyl) ether 4,4-diamino diphenyl ur 1,5-bis(4-aminophenoxy)pentane From the class of commercially available diamines (L) more preferred are the below listed ones: Aromatic diamines 2,7-diaminofluorene 4,4'-diaminooctafluorobiphenyl 4,4'-diaminodiphenyl ether 4,4'-diaminodiphenylmethane 4,4'-ethylenedianiline 3,3'-diaminobenzophenone 4-[3-(4-aminophenoxy)propoxy]aniline 4,4'-diaminodiphenyl sulfide 4,4'-diaminobenzophenone 2,2-bis(4-aminophenyl) hexafluoropropane 4,4'-bis(4-aminophenoxy)biphenyl 2,2-bis[4-(4-aminophenoxy)phenyl]propane 1,4-bis(4-aminophenoxy)benzene 1,3-bis(4-aminophenoxy)benzene 9,9-bis(4-aminophenyl)fluorene benzidine bis(p-aminophenoxy) dimethylsilane 4-[4-(4-aminophenoxy)butoxy]aniline 3,4'-diaminochalcone trimethylene bis(4-aminobenzoate) 3,4'-diaminobiphenyl 2,7-diamino-9-fluorenone 4',4"(5")-diaminodibenzo-15-crown-5 4-[4-(4-aminophenoxy)-2,3,5,6-tetrafluorophenoxy]aniline 4-[1-(4-aminophenyl)-1-methylethyl]aniline 1,5-bis(4-aminophenoxy)pentane Aliphatic diamines 4,4'-methylenebis(cyclohexylamine) 1,4-diaminocyclohexane Alicyclic diamines 4,4'-methylenebis(cyclohexylamine)

A further embodiment of the present invention is a composition comprising at least one first compound (I) and optionally at least one second compound (I), which is not identical to formula (I), or/and an additive. Preferred is a second diamine (I), wherein B is substituted by at least one, two, three, four, five, six or seven fluor atoms, preferably by two, three or five fluor atoms and more preferably by three fluor atoms, whereby the fluor substituent is preferably in the terminal position of the alkyl group B.

Preferred is a composition comprising at least one diamine (I) and optionally at least one further diamine, which is different from (I) or/and an additive.

Preferably, the further diamine is of formula (L).

Additives such as silane-containing compounds and epoxy-containing crosslinking agents may be added.

Suitable silane-containing additives are described in Plast. Eng. 36 (1996), (Polyimides, fundamentals and applications), Marcel Dekker, Inc.

Suitable epoxy-containing cross-linking additives include 4,4'-methylene-bis-(N,N-diglycidylaniline), trimethylolpropane triglycidyl ether, benzene-1,2,4,5-tetracarboxylic acid 1,2,4,5-N,N'-diglycidyldiimide, polyethylene glycol diglycidyl ether, N,N-diglycidylcyclohexylamine and the like.

Additional additives are surfactants, photo-sensitizers, photo-radical generators, cationic photo-initiators.

Suitable photo-active additives include 2,2-dimethoxyphenylethanone, a mixture of diphenyl-methanone and N,N-dimethylbenzenamine or ethyl 4-(dimethylamino)benzoate, xanthone, thioxanthone, Irgacure® 184, 369, 500, 651 and 907 (Ciba), Michler's ketone, triaryl sulfonium salt and the like.

The synthesis of the compounds of the present invention can be conducted in many known ways (see J. March, Advanced Organic Chemistry, second edition, pages 363 and 365).

In addition, the present invention relates to polymer, homo- or copolymer and oligomer comprising at least a compound (I), preferably a diamine (I), as one of the basic building blocks.

Preferably, the further polymer, homo- or copolymer or oligomer comprises at least a diamine (I), as one of the basic building block, and a tetracarboxylic acid anhydride, preferably a tetracarboxylic acid anhydride of formula (V).

Preferably, the substituted or unsubstituted, preferably substituted within polar group or unsubstituted, tetracarboxylic acid anhydride is of formula (V)

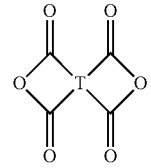

(V)

wherein:
T represents a tetravalent organic radical.

The tetravalent organic radical T is preferably derived from an aliphatic, alicyclic or aromatic tetracarboxylic acid dianhydride.

The tetracarboxylic dianhydride used in the present invention is not particularly limited, and represents for examples a compound of formula (XXIII)

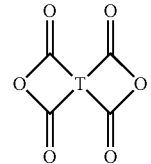

(XXVI)

wherein:
T represents a tetravalent organic radical.

The tetravalent organic radical T is preferably derived from an aliphatic, alicyclic or aromatic tetracarboxylic acid dianhydride.

Preferred examples of aliphatic or alicyclic tetracarboxylic acid dianhydrides are: 1,1,4,4-butanetetracarboxylic acid dianhydride, ethylenemaleic acid dianhydride, 1,2,3,4-cyclobutanetetracarboxylic acid dianhydride, 1,2,3,4-cyclopentanetetracarboxylic acid dianhydride; 2,3,5-tricarboxycyclopentylacetic acid dianhydride (with the term "2,3,5-tricarboxycyclopentylacetic acid dianhydride" all isomers of this compound are incorporated especially the exo and/or endo body), 2,3,5-tricarboxycyclopentylacetic-1,2:3,4-dianhydride is accessible for example by processes as described in JP59-190945, JP60-13740 and JP58-109479, respectively DE 1078120 and JP58-109479, or GB 872,355, and JP04458299, which processes are herewith incorporated by reference; tetrahydro-4,8-methanofuro[3,4-d]oxepine-1,3,5,7-tetrone, 3-(carboxymethyl)-1,2,4-cyclopentanetricarboxylic acid 1,4:2,3-dianhydride, hexahydrofuro[3',4':4,5]cyclopenta[1,2-c]pyran-1,3,4,6-tetrone, 3,5,6-tricarboxynorbornylacetic acid dianhydride, 2,3,4,5-tetrahydrofurantetracarboxylic acid dianhydride,rel-[1S,5R,6R]-3-oxabicyclo[3.2.1]octane-2,4-dione-6-spiro-3'-(tetrahydrofuran2',5'-dione), 4-(2,5-dioxotetrahydrofuran-3-yl)tetrahydronaphthalene-1,2-dicarboxylicacid dianhydride, 5-(2,5-dioxotetrahydrofuran-3-yl)-3-methyl-3-cyclohexene-1,2-dicarboxylic-acid dianhydride, bicyclo[2.2.2]oct-7-ene-2,3,5,6-tetracarboxylic acid dianhydride, bicyclo[2.2.2]octane-2,3,5,6-tetracarboxylic acid dianhydride, 1,8-dimethylbicyclo[2.2.2]oct-7-ene-2,3,5,6-tetracarboxylic acid dianhydride, pyromellitic acid dianhydride, 3,3',4,4'-benzophenonetetracarboxylic acid dianhydride, 4,4'-oxydiphthalic acid dianhydride, 3,3',4,4'-diphenylsulfonetetracarboxylic acid dianhydride, 1,3-dimethyl-1,2,3,4-cyclobutanetetracarboxylicacid dianhydride, 1,3-difluoro-1,2,3,4-cyclobutanetetracarboxylicacid dianhydride, 1,3-dichloro-1,2,3,4-cyclobutanetetracarboxylicacid dianhydride, 1,2,3-trimethyl-1,2,3,4-cyclobutanetetracarboxylicacid dianhydride, 1,2,3,4-tetramethyl-1,2,3,4-cyclobutanetetracarboxylicacid dianhydride, 1-methyl-1,2,3,4-cyclobutanetetracarboxylicacid dianhydride, 1,4,5,8-naphthalenetetracarboxylic acid dianhydride, 2,3,6,7-naphthalenetetracarboxylic acid dianhydride, 3,3',4,4'-dimethyldiphenylsilanetetracarboxylic acid dianhydride, 3,3',4,4'-tetraphenylsilanetetracarboxylic acid dianhydride, 1,2,3,4-furantetracarboxylic acid dianhydride, 4,4'-bis(3,4-dicarboxyphenoxy)diphenyl sulfide dianhydride, 4,4'-bis(3,4-dicarboxyphenoxy)-diphenyl sulfone dianhydride, 4,4'-bis(3,4-dicarboxyphenoxy)-diphenylpropane dianhydride, 3,3',4,4'-biphenyltetracarboxylic acid dianhydride, ethylene glycol bis(trimellitic acid) dianhydride, 4,4'-(1,4-phenylene)bis(phthalic acid) dianhydride, 4,4'-(1,3-phenylene)bis(phthalic acid) dianhydride, 4,4'-(hexafluoroisopropylidene)diphthalic acid dianhydride, 4-tert-butyl-6-(2,5-dioxotetrahydro-3-furanyl)-2-benzofuran-1,3-dione, 5-(2,5-dioxotetrahydro-3-furanyl)-3a, 4,5,9b-tetrahydronaphtho[1,2-c]furan-1,3-dione, 5-(2,5-dioxotetrahydro-3-furanyl)-5-methyl-3a,4,5,9b-tetrahydronaphtho[1,2-c]furan-1,3-dione, 5-(2,5-dioxotetrahydro-3-furanyl)-6-methylhexahydro-2-benzofuran-1,3-dione, 5-(2,5-dioxotetrahydro-3-furanyl)-7-methyl-3a,4,5,7a-tetrahydro-2-benzofuran-1,3-dione, 5-(2,5-dioxotetrahydro-3-furanyl)-4-methylhexahydro-2-benzofuran-1,3-dione, 9-isopropyloctahydro-4,8-ethenofuro[3',4':3,4]cyclobuta[1,2-f][2]benzofuran-1,3,5,7-tetrone, 1,2,5,6-cyclooctanetetracarboxylic acid dianhydride, octahydro-4,8-ethenofuro[3',4':3,4]cyclobuta[1,2-f][2]benzofuran-1,3,5,7-tetrone, octahydrofuro[3',4':3,4]cyclobuta[1,2-t][2]benzofuran-1,3,5,7-tetrone, tetrahydro-3,3'-bifuran-2,2',5,5'-tetrone, 4,4'-oxydi(1,4-phenylene)bis(phthalic acid) dianhydride, and 4,4'-methylenedi(1,4-phenylene)bis(phthalic acid) dianhydride.

Preferred examples of aromatic tetracarboxylic acid dianhydrides are: pyromellitic acid dianhydride, 3,3',4,4'-benzophenonetetracarboxylic acid dianhydride, 4,4'-oxydiphthalic acid dianhydride, 3,3',4,4'-diphenylsulfonetetracarboxylic acid dianhydride, 1,4,5,8-naphthalenetetracarboxylic acid dianhydride, 2,3,6,7-naphthalenetetracarboxylic acid dianhydride, 3,3',4,4'-dimethyldiphenylsilanetetracarboxylic acid dianhydride, 3,3',4,4'-tetraphenylsilanetetracarboxylic acid dianhydride, 1,2,3,4-furantetracarboxylic acid dianhydride, 4,4'-bis(3,4-dicarboxyphenoxy)diphenyl sulfide dianhydride, 4,4'-bis(3,4-dicarboxyphenoxy)diphenyl sulfone dianhydride, 4,4'-bis(3,4-dicarboxyphenoxy)diphenylpropane dianhydride, 3,3',4,4'-biphenyltetracarboxylic acid dianhydride, ethylene glycol bis(trimellitic acid) dianhydride, 4,4'-(1,4-phenylene)bis(phthalic acid) dianhydride, 4,4'-(1,3-phenylene)bis(phthalic acid) dianhydride, 4,4'-(hexafluoroisopropylidene)diphthalic acid dianhydride, 4,4'-oxydi(1,4-phenylene)bis(phthalic acid) dianhydride, 4,4'-methylenedi(1,4-phenylene)bis(phthalic acid) dianhydride, 4-tert-butyl-6-(2,5-dioxotetrahydro-3-furanyl)-2-benzofuran-1,3-dione, and the like.

More preferably the tetracarboxylic acid dianhydrides used to form the tetravalent organic radical T are selected from: 1,2,3,4-cyclobutanetetracarboxylic acid dianhydride, 1,2,3,4-cyclopentanetetracarboxylic acid dianhydride, 2,3,5-tricarboxycyclopentylacetic acid dianhydride, tetrahydro-4,8-methanofuro[3,4-d]oxepine-1,3,5,7-tetrone, 3-(carboxymethyl)-1,2,4-cyclopentanetricarboxylic acid 1,4:2,3-dianhydride, hexahydrofuro[3',4':4,5]cyclopenta[1,2-c] pyran-1,3,4,6-tetrone, 5-(2,5-dioxotetrahydrofuran-3-yl)-3-methyl-3-cyclohexene-1,2-dicarboxylic acid dianhydride, pyromellitic acid dianhydride, 4-(2,5-dioxotetrahydrofuran-3-yl)tetrahydronaphthalene-1,2-dicarboxylic acid dianhydride, 5-(2,5-dioxotetrahydro-3-furanyl)-5-methyl-3a,4,5,9b-tetrahydronaphtho[1,2-c]furan-1,3-dione, 5-(2,5-dioxotetrahydro-3-furanyl)-3a,4,5,9b-tetrahydronaphtho[1,2-c]furan-1,3-dione, 5-(2,5-dioxotetrahydro-3-furanyl)-7-methyl-3a,4,5,7a-tetrahydro-2-benzofuran-1,3-dione, 4-tert-butyl-6-(2,5-dioxotetrahydro-3-furanyl)-2-benzofuran-1,3-dione, 4,4'-(hexafluorneoisopropylidene)diphthalic acid dianhydride and bicyclo[2.2.2]oct-7-ene-2,3,5,6-tetracarboxylic acid dianhydride.

In the context of the present invention the term "polymer" denotes homo- or copolymer or oligomer.

Preferably, the polymer, copolymer or oligomer comprising diamine (I) as one basic building block are in the context of the invention a polyamic acid, polyamic ester, polyimide or a mixture thereof, preferably a mixture of polyamic acid and polyamic ester and/or polyimide. More preferred is a mixture of polyamic acid and polyimide.

In the context of the present invention the term "polyimide" has the meaning of partially or complete imidisated polyamic acid or polyamic ester. In analogy, the term "imidisation" has in the context of the present invention the meaning of partially or complete imidisation.

In a further preferred embodiment the present invention relates to polymer, homo- or copolymer and oligomer which is 100% imidised, or has an imidisation degree in the range of 1 to 99%, preferably 5 to 50%, more preferably 10 to 40% by weight.

Preferred copolymer comprises at least a compound (I), preferably diamine (I) and a tetracarboxylic acid anhydride, preferably tetracarboxcylic anhydride (V), as basic building blocks.

Further preferred copolymer comprises
a further diamine, which is different from that of formula (I), preferably in the presence of at least one diamine (L), with the meaning and preferences as described above, and/or
a further diamine (I), wherein preferably B is substituted by at least one, two, three, four, five, six or seven fluor atoms, preferably by two, three or five fluor atoms and more preferably by three fluor atoms, whereby the fluor substituent is preferably in the terminal position of the alkyl group B, whereby preferably the ratio of with fluor in B substituted diamine (I) to diamine (I) not substituted with fluor, and preferably substituted with an polar group, especially nitril, is from 0.1:99.9 to 50:50, especially to 30:70, preferably to 20:80 and more preferably to 10:90, and most preferably 5:95, and/or
a further polymer, homo- or copolymer or oligomer comprising as one basic building block a diamine (L), or a further polymer, copolymer or oligomer, which is different from a polyamic acid, polyamic ester or a polyimide, more preferably a further polymer, copolymer or oligomer, which is selected from the group of which is selected from the group of polymers include polyacrylates, polymethacrylates, polyacrylamides, polymethacrylamides, polyvinylether and polyvinylester, polyallylether and ester, polystyrenes, polysiloxanes, polyimides, polyamic acids and their esters, polyamidimides, polymaleic acids, polyfumaric acids polyurethanes and derivatives thereof; and/or
a second diamine (I) without polar group, wherein preferably B is substituted by at least one, two, three, four, five, six or seven fluor atoms, preferably by two, three or five fluor atoms and more preferably by three fluor atoms, whereby the fluor substituent is preferably in the terminal position of the alkyl group B, whereby preferably the ratio of with fluor in B substituted diamine (I) to diamine (I) not substituted with fluor, and preferably substituted with an polar group, especially nitril, is from 0.1:99.9 to 30:70, preferably to 20:80 and more preferably to 10:90, and most preferably 5:95, and/or.

Preferably, the further polymer, homo- or copolymer or oligomer comprises as basic building block a diamine (L) and a tetracarboxylic acid anhydride, preferably a tetracarboxylic acid anhydride of formula (V), a polymerizable photosensitizer, such as a diamine derivative of benzophenone or acetophenone; polymerizable photo-radical generators or polymerizable UV absorber, polymerizable quencher.

This polymer, copolymer or oligomer is prepared in analogy to the polymer, copolymer or oligomer of the invention comprising compound (I), preferably a diamine (I).

A further embodiment of the present invention relates to a composition, especially a blend, comprising
- a polymer, homo- or copolymer, or oligomer comprising at least a compound (I), preferably a diamine (I), as described above and within the above given preferences, as basic building block, or
- a polymer, homo- or copolymer or oligomer obtainable as described below.

In addition, preferably, the present invention concerns a composition, especially a blend, comprising
- a polymer, copolymer or oligomer according to definition and preferences of the invention, comprising at least a diamine (I) as basic building block, or
- a polymer, copolymer or oligomer according to definition and preferences of the invention, obtainable by the processes of the invention,
- a polymer, homo- or copolymer or oligomer comprising at least one first monomer (I), preferably a diamine (I), and optionally at least one second monomer (I), preferably a diamine (I), which is not identical to formula (I), or/and an additive. Preferred is a second diamine (I), wherein B is substituted by at least one, two, three, four, five, six or seven fluor atoms, preferably by two, three or five fluor atoms and more preferably by three fluor atoms, whereby the fluor substituent is preferably in the terminal position of the alkyl group B, whereby preferably the ratio of with fluor in B substituted diamine (I) to diamine (I) not substituted with fluor, and preferably substituted with an polar group, especially nitiril, is from 0.1:99.9 to 30:70, preferably to 20:80 and more preferably to 10:90, and most preferably 5:95,
  and/or a further polymer, copolymer or oligomer comprising as one basic building block a further diamine, which is different from diamine (I), preferably a diamine (L), or a further polymer, copolymer or oligomer, which is different from a polyamic acid, polyamic ester or a polyimide, more preferably a further polymer, copolymer or oligomer, which is selected from the group of polyacrylate, polystyrol, polyester, polyurethane, polyethylene, poylpopylen, polyvinylchloride, polytetrafluoroethylen, polycabonate, polyterephthalate and dendrimere, and/or
- a polymer, homo- or copolymer or oligomer comprising at least one first monomer (I), preferably a diamine (I), and a polymerizable liquid crystal (LCP), or polymerized liquid crystal, preferably a liquid crystal having a polar group.

The compositions, preferably blends comprising a polymer, copolymer or oligomer according to definition and preferences of the invention, comprising, optionally further an organic solvent. Organic solvent includes, however, is not limited to chlorobenzene, pyrrolidone solvents such as preferably, N-methyl-2-pyrrolidone, N-ethyl-2-pyrrolidone, N-cyclohexyl-2-pyrrolidone; imidazolidinone, dimethylsulfoxide, dimethylformamide, toluene, chloroform, organic ester, such as acetyl acetic ester or butyl acetic ester, pentyl acetic ester, hexyl acetic ester; further Y-butyrolactone, methyl cellosolve, butyl cellosolve, butyl carbitol, tetrahydrofuran, diethylene glycol diethylether, dipentylether dipropylene glycol dimethylether, diisobutyl ketone monoethylene glycol dimethyl ether, etc. These solvents can be used alone or in mixtures thereof.

Further preferably, the present invention relates to a composition, especially a blend, comprising
- a polymer, copolymer or oligomer according to definition and preferences of the invention, comprising at least a diamine (I) as basic building block, or
- a polymer, copolymer or oligomer according to definition and preferences of the invention, obtainable by the processes of the invention,
- and optionally a further diamine, which is different from diamine (I), preferably a diamine (L),
- and an additive, preferably silane-containing compounds,
- and/or a further polymer, copolymer or oligomer comprising as one basic building block a further diamine, which is different from diamine (I),
- preferably at least one diamine (L),
- and/or a further polymer, copolymer or oligomer, which is different from a polyamic acid, polyamic ester or a polyimide, more preferably a further polymer, copolymer or oligomer, which is selected from the group of polymers include polyacrylates, polymethacrylates, polyacrylamides, polymethacrylamides, polyvinylether and polyvinylester, polyallylether and ester, polystyrenes, polysiloxanes, polyimides, polyamic acids and their esters, polyamidimides, polymaleic acids, polyfumaric acids polyurethanes and derivatives thereof,
- and/or photo-active polymers, photo-active oligomers and/or photo-active monomers,
- and/or cross-linking agents, preferably epoxy-containing cross-linking agents, most preferably selected from the group: 4,4'-methylene-bis-(N,N-diglycidylaniline), trimethylolpropane triglycidyl ether, benzene-1,2,4,5-tetracarboxylic acid 1,2,4,5-N,N'-diglycidyldiimide, polyethylene glycol diglycidyl ether, N,N-diglycidylcyclohexylamine.

A further embodiment of the present invention relates to a polymer, homo- or copolymer or oligomer, or to a composition, preferably a blend, comprising
- a polymer, homo- or copolymer, or oligomer comprising at least a diamine (I) as basic building block, or
- obtainable according to the processes and preferred processes of the invention, preferably by reaction of at least one diamine (I), or two different diamine (I), or by bringing into contact of at least one diamine (I) with a polymer, copolymer or oligomer comprising as basic building block at least one diamine (L).

The polymer, homo- or copolymer or oligomer, especially the polyamic acid, polyamic acid ester and polyimide and mixtures thereof may be prepared in line with known methods, such as those described in Plast. Eng. 36 (1996), (Polyimides, fundamentals and applications), Marcel Dekker, Inc.

The present invention relates also to a process for the preparation of a polymer, homo- or copolymer or oligomer comprising polymerisation of a diamine (I).

Preferably the polymerisation of a diamine (I) comprises
a) amidisation of at least one diamine (I) to polyamic acid or a polyamic ester, and
b) imidisation of the obtained polyamic acid or ester, to a polyimide, or
c) imidisation of the diamine (I) to polyimide.

For example, the amidisation, poly-condensation reaction for the preparation of the polyamic acids is carried out in solution in a polar aprotic organic solvent, such as γ-butyrolactone, N,N-dimethylacetamide, N-methylpyrrolidone or N,N-dimethylformamide. In most cases equimolar amounts of the anhydride and the diamine are used, i.e. one amino group per anhydride group. If it is desired to stabilize the molecular weight of the polymer, copolymer or oligomer, it is possible for that purpose to either add an excess or a less-than-stoichiometric amount of one of the two components or to add a mono-functional compound in the form of a dicarboxylic acid monoan-hydride or in the form of a monoamine. Examples of such mono-functional compounds are maleic acid anhydride, phthalic acid anhydride, aniline and the like. Preferably the reaction is carried out at temperatures of less than 100° C.

In a preferred embodiment of the process of the invention the amidisation step a diamine (I) is reacted with one or more tetracarboxylic acid anhydrides of the general formula (V), optionally in the presence of one or more additional other diamines.

Further, the present invention preferably relates to a process, wherein a poly-condensation reaction for the preparation of the polyamic acids is carried out in solution in a polar aprotic organic solvent, preferably selected from γ-butyrolactone, N,N-dimethylacetamide, N-methylpyrrolidone or N,N-dimethylformamide.

In addition, preferably, the present invention relates to a process, wherein subsequent to the poly-condensation cyclisation with removal of water is carried out thermally under formation of a polyimide.

The imidisation, cyclisation of the polyamic acids to form the polyimides can be carried out by heating, i.e. by condensation with removal of water or by other imidisation reactions using appropriate reagents.

Partially imidisation is achieved for example, if the imidisation is carried out purely thermally, the imidisation of the polyamic acids may not always be complete, i.e. the resulting polyimides may still contain proportions of polyamic acid.

Complete imidisation reactions are carried out at temperatures between 60 and 250° C., preferably at temperatures of less than 200° C.

In order to achieve imidisation at lower temperatures additional reagents that facilitate the removal of water are added to the reaction mixture. Such reagents are, for example, mixtures consisting of acid anhydrides, such as acetic acid anhydride, propionic acid anhydride, phthalic acid anhydride, trifluoroacetic acid anhydride or tertiary amines, such as triethylamine, trimethylamine, tributylamine, pyridine, N,N-dimethylaniline, lutidine, collidine etc. The amount of aforementioned additional reagents that facilitate the removal of water is preferably at least four equivalents of acid anhydride and two equivalents of amine per equivalent of polyamic acid to be condensed.

The imidization degree of each polymer used in the liquid crystal alignment agent of the invention can be arbitrarily adjusted by controlling the catalyst amount, reaction time and reaction temperature employed in production of the polymer. In the present description, "imidization degree" of polymer refers to a proportion (expressed in %) of the number of recurring units of polymer forming an imide ring or an isoimide ring to the number of total recurring units of polymer. In the present description, the imidization degree of a polyamic acid not subjected to dehydration and ring closure is 0%. The imidization degree of each polymer is determined by dissolving the polymer in deuterated dimethyl sulfoxide, subjecting the resulting solution to $^1$H-NMR measurement at a room temperature using tetramethylsilane as a standard substance, and calculating from the following formula:

$$\text{Imidization degree (\%)} = 1 - (A^1/A2 \times B) \times 100$$

$A^1$: Peak area based on protons of NH groups (in the vicinity of 10 ppm)
$A^2$: Peak area based of one proton of acrylate double bond (in the vicinity of 6.5 ppm).
B: Proportion of the number of acrylate protons to one proton of NH group in the polymer precursor The imidization degree is usually in the range of 1 to 99%, preferably 5 to 50%, more preferably 10 to 40%.

More preferably, the present invention relates to a process, wherein imidisation is carried out prior or after the application of the polymer, homo- or copolymer or oligomer to a support.

In a further more preferred embodiment of the invention, the polymerisation of the diamine comprises the amidisation of at least one diamine of compound (I) with tetracarboxylic acid anhydride, preferably tetracarboxylic acid anhydride (V), and/or the imidisation, preferably by elevated temperature.

In a further more preferred embodiment of the invention, the polymerisation of the diamine comprises the amidisation of a diamine (I) with tetracarboxylic acid anhydride, preferably tetracarboxylic acid anhydride (V), and/or the imidisation, preferably by elevated temperature, and wherein the amidisation and/or imidisation is optionally conducted
  in the presence of additives as given above, and/or
  in the presence of a further diamine, which is different from that of formula (I), preferably in the presence of at least one diamine (L) and/or
  in the presence of a further polymer, homo- or copolymer or oligomer comprising as one basic building block a diamine (L), or a further polymer, copolymer or oligomer, which is different from a polyamic acid, polyamic ester or a polyimide, more preferably a further polymer, copolymer or oligomer, which is selected from the group of which is selected from the group of polymers include polyacrylates, polymethacrylates, polyacrylamides, polymethacrylamides, polyvinylether and polyvinylester, polyallylether and ester, polystyrenes, polysiloxanes, polyimides, polyamic acids and their esters, polyamidimides, polymaleic acids, polyfumaric acids polyurethanes and derivatives thereof.

Preferably, the present invention relates to a process for the preparation of a polymer, homo- or copolymer or oligomer comprising polymerisation of a diamine (I) and tetracarboxylic acid anhydride, preferably tetracarboxylic acid anhydride (V).

The imidisation is conducted after or during amidisation. In general, the imidisation is conducted after amidisation.

Preferred is the partially imidisation of polyamic acid or polyamic ester.

If the polymer is prepared only by imidisation, diamine (I) will be contacted with an imidisation compound, with at least two polymerisable functional groups, such as for example, carbonyl groups or halogen groups.

The polymer, copolymer or oligomer, comprise in their polymer-, homo- or copolymer- or oligomer-side-chains at least one photo-reactive group. Preferably, the photo-reactive group of the side chains reacts by exposure to aligning light.

In the context of the present invention the term photoreactive groups have the meaning of groups, which are able to react by interaction with light, preferably aligning light.

The treatment with aligning light may be conducted in a single step or in several separate steps. In a preferred embodiment of the invention the treatment with aligning light is conducted in a single step.

In the context of the present invention photo-reactive group has preferably the meaning of a dimerizable, isomerizable, polymerizable and/or cross-linkable group.

In the context of the present invention, aligning light, preferably polarized light, is light of wavelengths, which can initiate photoalignment. Preferably, the wavelengths are in the UV-A, UVB and/or UV/C-range, or in the visible range. It depends on the photoalignment compound, which wavelengths are appropriate. Preferably, the photo-reactive groups are sensitive to visible and/or UV light. A further embodiment of the invention concerns the generating of aligning light by laser light.

The instant direction of the aligning light may be normal to the substrate or at any oblique angle. More preferably, aligning light is at least partially linearly polarized, elliptically polarized, such as for example circularly polarized, or non-polarized; most preferably at least circularly or partially linearly polarized light, or non-polarized light exposed obliquely. Especially, most preferred aligning light denotes substantially polarised light, especially linearly polarised light; or aligning light denotes non-polarised light, which is applied by an oblique irradiation.

A more preferred embodiment of the invention relates to a process for the preparation the polymer, homo- or copolymer or oligomer is treated with polarised light, especially linearly polarised light, or by oblique radiation with non-polarised light.

Further preferred are polymers, homo- or copolymers or oligomers of the present invention,
  wherein at least 1%, preferably at least 5%, more preferably at least 8, most preferably 10 or more %, especially most preferably at least, 15%, more especially most preferably at least, 30%, preferably at least 75% of the repeating units include a side chain with a photo-reactive group; and/or
  wherein, the photo-reactive groups are able to dimerize, isomerize, polymerize; and/or
  wherein the polymer, homo- or copolymer or oligomer is a polymer gel or a polymer network, or an oligomer gel or an oligomer network, respectively; and/or
  wherein the polymer, homo- or copolymer or oligomer has an intrinsic viscosity in the range of 0.05 to 10 dL/g, preferably in the range of 0.05 to 5 dL/g; and/or
  wherein the polymer, homo- or copolymer or oligomer contains from 2 to 2000 repeating units, especially from 3 to 200 repeating units; and/or
  wherein the polymer, homo- or copolymer or oligomer is in the form of a homopolymer or of a copolymer, preferably of a statistical copolymer.

A further preferred embodiment of the present invention relates to polymers, homo- or copolymers or oligomers, having an intrinsic viscosity preferably in the range of 0.05 to 10 dL/g, more preferably in the range of 0.05 to 5 dL/g. Herein, the intrinsic viscosity ($\eta_{inh}$=ln $\eta_{rel}$/C) is determined by measuring a solution containing a polymer homo- or copolymers or an oligomer in a concentration of 0.5 g/100 ml solution for the evaluation of its viscosity at 30° C. using N-methyl-2-pyrrolidone as solvent.

In addition, a preferred embodiment of the present invention relates to polymers, homo- or copolymers or oligomers, containing from 2 to 2000 repeating units, especially from 3 to 200 repeating units.

The present invention also relates to the use of the polymer, homo- or copolymer, or oligomer according to the invention for the preparation of polymer or oligomer layers.

In the context of the present invention the wording "polymer or oligomer layer" has the meaning of "polymer layer, copolymer layer, homopolymer layer or oligomer layer".

In the context of the present invention polymer or oligomer layers are preferably orientation layers. The polymers, homo- or copolymers or oligomers according to the invention may be used in form of polymer layers or oligomer layers alone or in combination with other polymers, oligomers, monomers, photo-active polymers, photo-active oligomers and/or photo-active monomers, depending upon the application to which the polymer or oligomer layer is to be added. Therefore it is understood that by varying the composition of the polymer or oligomer layer it is possible to control specific and desired properties, such as an induced pre-tilt angle, good surface wetting, a high voltage holding ratio, a specific anchoring energy, etc.

Polymer or oligomer layers may readily be prepared from the polymers or oligomers of the present invention and a further embodiment of the invention relates to a polymer or oligomer layer comprising a polymer or oligomer according to the present invention, which is preferably prepared by treatment with aligning light.

Preferably, the invention relates to a polymer-, homo- or copolymer-, or oligomer layer comprising a polymer, homo- or copolymer, or oligomer according to the present invention or as prepared according to the present invention.

Further the present invention relates to a process for the preparation of a polymer or oligomer layer by irradiation the polymer, homo- or copolymer, or oligomer of the present invention with aligning light.

The polymer or oligomer layer is preferably prepared by applying one or more polymers or oligomers according to the invention to a support and, after imidisation or without imidisation, irradiating the polymer or oligomer or polymer mixture or oligomer mixture with aligning light. Aligning light has the above given meaning and preferences.

In a more preferred embodiment of the invention the polymer, homo- or copolymer or oligomer is treated with polarised light, especially linearly polarised light, or by oblique radiation with non-polarised light.

The irradiation time is dependent upon the output of the individual lamps and can vary from a few seconds to several hours. The photo-reaction can also be carried out, however, by irradiation of the homogeneous layer using filters that, for example, allow only the radiation suitable for the reaction to pass through.

The term "support" as used in the context of the present invention is preferably transparent or not-transparent, preferably glass or plastic substrates, polymer films, such as polyethyleneterephthalate (PET), tri-acetyl cellulose (TAC), polypropylene, optionally coated with indium tin oxide (ITO), however not limited to them.

In general a composition comprising the polymers or oligomers of the invention is applied by general coating and printing methods known in the art, such as spin-coating, meniscus-coating, wire-coating, slot-coating, offset-printing, flexo-printing, gravure-printing, ink jet printing may be used. Coating methods are for example spin coating, air doctor coating, blade coating, knife coating, reverse-roll coating, transfer roll coating, gravure roll coating, kiss roll coating, cast coating, spray coating, slot-orifice coating, calendar coating, electrodepositing coating, dip coating or die coating.

Printing methods are for example relief printing such as flexographic printing, ink jet printing, intaglio printing such as direct gravure printing or offset gravure printing, lithographic printing such as offset printing, or stencil printing such as screen printing.

A further preferred embodiment of the present invention relates to polymer layers or oligomer layers which are unstructured or structured.

In addition the present invention relates to a process for the preparation of structured polymer layers or oligomer layers comprising varying the direction of orientation and/or the tilt angle within the polymer or oligomer layer.

This varying of the direction of orientation and/or the tilt angle can for example be conducted by controlling the direction of the irradiation of the aligning light. It is understood that by selectively irradiating specific regions of the polymer or oligomer layer very specific regions of the layer can be aligned. In this way, layers with a defined tilt angle can be provided.

Further preferred is a process for the preparation of a polymer layer or oligomer layer;
for the preparation of planar multi-domain planar alignment of a polymer layer or oligomer layer; and/or
for the preparation of a polymer layer or oligomer layer having a tilt angle within the given meaning and preferences of the invention.

A further preferred embodiment of the invention relates to an orientation layer comprising one or more polymers or oligomers according to the invention.

In the context of the present invention orientation layer has the same meaning and preferences as alignment layer, polymer, homo- or copolymer or oligomer layer and is preferably a photo alignment layer.

In a more preferred embodiment the invention relates to an orientation layer according to the invention for the planar alignment of liquid crystals.

In the context of the present invention the wording "planar alignment of liquid crystals" means that the liquid crystals have tilt angle.

A further preferred embodiment of the invention relates to an orientation layer comprising one or more polymers or oligomers according to the invention.

In a more preferred embodiment the invention relates to an orientation layer according to the invention for the planar alignment of liquid crystals.

In the context of the present invention the wording "planar alignment of liquid crystals" means that the liquid crystals have tilt angle.

The term tilt angle as used in the context of the present invention is the angle between the liquid crystal director and the surface of the alignment layer. The liquid crystal director shall mean the average direction of the long axes of the liquid crystal molecules. In the context of the present invention, planar alignment shall mean that the tilt angle is less than 30°, preferably 0 to 30°.

In preferred embodiments the tilt angle, which the photo-alignment layer induces in liquid crystal materials is less than 10°, preferably 0 to 10°. In more preferred embodiments the tilt angle is less than 5°, preferably 0 to 5°, and in most preferred embodiments the tilt angle is less than 1°, preferably 0 to 1°.

The present invention also relates to the use of such orientation layers for the alignment, preferably planar alignment, of liquid crystals, preferably in the manufacture of unstructured or structured optical- or electro-optical elements, preferably in the production of hybrid layer elements. Preferably these optical or electro-optical devices. have at least one orientation layer as well as unstructured and structured optical elements and multi-layer systems. The layer, or each of the layers may contain one or more regions of different spatial orientation.

Further, the present invention relates preferably to the use of an orientation layer according to the invention for the induction of planar alignment of adjacent liquid crystalline layers, in particular for operating a cell wherein planar orientation is provided, such in IPS, such as IPS modes like S-IPS (Super IPS), AS-IPS (Advanced super IPS), E-IPS (Enhanced IPS), H-IPS (Horizontal IPS), UH-IPS, S-IPS II, e-IPS, p-IPS (performance IPS), PLS technology (plane to line switching), PS-IPS (polymer stabilized IPS), Field induced photoreactive alignment IPS FFS (fringe field switching), TN (twisted nematic), STN (supertwisted nematic).

Further, the present invention relates to an orientation layer, comprising at least one polymer I, homo- or copolymer or oligomer according to the present invention.

The present invention relates further to a polymer, homo- or copolymer or oligomer layer according to the invention for the planar alignment of liquid crystals.

A preferred embodiment of the present invention is the use of a polymer, homo- or copolymer or oligomer layer, especially orientation layer, according to the invention for the alignment, especially the planar alignment, of
  a) a liquid crystal composition comprising a polymerizable monomer, preferably a mono- or/and multi-polymerizable monomer, or a polymer or oligomer, which is the polymerized form of said polymerizable monomer, or/and
  b) liquid crystals, which are sandwiched between a pair of polymer films made from b1) at least one polymerizable monomer in said liquid crystal material or/and
    b2) at least a single polymerizable liquid crystal, LCP, such as for example those described in US2012/0114907A1 and which is herewith incorporated by reference; and which polymer films are formed on said polymer, homo- or copolymer or oligomer layers.

Liquid crystal compositions of the present invention comprise a polymerizable monomer, or a polymer or oligomer, which is the polymerized form of said polymerizable monomer. The polymerizable monomer or the polymer or oligomer, is bifunctional and/or has a rigid core (e.g. benzene). Further preferred is a polymerizable monomer, or a polymer or oligomer, which have one or more ring or condensed ring structures and functional groups bonded directly to the ring or condensed ring structure.

More preferred is a monomer of formula (IXXX)

$$P_1—S_1-A_1-(Z_1-A_2)_n-S_2—P_2 \quad (IXXX)$$

wherein
$P_1$ and $P_2$ are functional groups and are independently selected from acrylate, methacrylate, halogenacrylate, such as fluoroacrylate, chloroacrylate; oxetanyl, maleinimidyl, allyl, allyloxy, vinyl, vinyloxy and epoxy groups,
$S_1$ and $S_2$ are independently from each other a single bond or spacer units,
$A_1$ and $A_2$ are ring structures and independently selected from unsubstituted or substituted carbocyclic or heterocyclic aromatic or alicyclic group with the meaning and preferences given in the present invention, especially preferred are 1,4-phenylene naphthalene-2,6-diyl, terphenyl, quaterphenyl, phenanthrene groups,
$Z_1$ is selected from —O—, —CO—, —CH(OH)—, —CH$_2$ (CO)—, —OCH$_2$—, —CH$_2$O—, —O—CH$_2$—O—, —COO—, —OCO—, —(CO)—(CO)—, —OCF$_2$—, —CF$_2$O—, —CF$_2$—, —CON(C$_1$-C$_{16}$alkyl)-, —(C$_1$-C$_{16}$alkyl)NCO—, —CONH—, —NHCO—, —HNOCO—, —OCONH—, —NHCONH—, —OCOO—, —CO—S—, —S—CO—, —CSS, —SOO—, —OSO—, —SOS—, —SO—, —CH$_2$(SO)—, —SO$_2$—, —CH═CH—, —C≡C—, —CH═CH—COO—, —OCO—CH═CH—, —CH═N—, —C(CH$_3$)═N—, —N═N—, or a single bond; or a cyclic, straight-chain or branched, substituted or unsubstituted C$_1$-C$_{24}$alkylen, wherein one or more C-atom, CH— or CH$_2$— group may independently from each other be replaced by a linking group;
preferably, $Z_1$ is —O—, —CO—, —COO—, —OCO—, —OCOO—, —OCF$_2$—, —CF$_2$O—, —CON(CH$_3$)—, —(CH$_3$)NCO—, —CONH—, —NHCO—, —CO—S—, —S—CO—, —CSS, —SOO—, —OSO—, —CSS—, —SOO—, —OSO—, —CH$_2$(SO$_2$)—, —CH$_2$—CH$_2$—, —OCH$_2$—, —CH$_2$O—, —CH═CH—, —C≡C—, —CH═CH—COO—, —OCO—CH═CH—, or a single bond;
more preferably $Z_1$ is —COO—, —OCO—, —OCOO—, —OCF$_2$—, —CF$_2$O—, —CON(CH$_3$)—, —(CH$_3$)NCO—, —CONH—, —NHCO—, —CO—S—, —S—CO—, —CS—S—, —SOO—, —OSO, especially —COO—, —OCO—, —OCF$_2$—, —CF$_2$O—, —CON(CH$_3$)—, —(CH$_3$)NCO—, —CONH—, —NHCO— or a single bond, most preferred $Z_1$ is a single bond, —COO— or —OCO—; and
n is an integer of 1, 2, or 3.

The term "linking group", as used in the context of the present invention is preferably be selected from a single bond, —S—, —S(CS)—, —(CS)S—, —CO—S—, —S—CO—, —O—, —CO, —CO—O—, —O—CO—,

NR$^{2'}$—, —NR$^{2'}$—CO—, —CO—NR$^{2'}$—, —NR$^{2'}$—CO—O—, —O—CO—NR$^{2'}$, —NR$^{2'}$—CO—NR$^{2'}$—, —CH═CH—, —C≡C—, —C══C—, —O—CO—O—, —Si(CH$_3$)$_2$—O—Si(CH$_3$)$_2$—, a cyclic, straight-chain or branched, substituted or unsubstituted C$_1$-C$_{24}$alkylen, wherein one or more C-atom, CH— or CH$_2$— group may independently from each other be replaced by —O—; and unsubstituted or substituted cyclohexylen and unsubstituted or substituted phenylene and wherein:

$R^{2'}$ represents a hydrogen atom or C$_1$-C$_6$alkyl; especially hydrogen or methyl; with the proviso that oxygen atoms of linking groups are not directly linked to each other; preferred is a single bond, —O—, —O(CO), —S—, —(CO)O— or

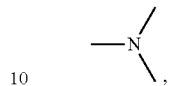

—NR$^{2'}$—.

In formula (IXXX), $P_1$ and $P_2$ are preferably acrylate or methacrylate groups, $S_1$ and $S_2$ are a single bond $Z_1$ is preferably a single bond, and n is preferably 0 or 1.

Most preferred is a compound represented by any one of the formulae (XXX), (XXXI) or (XXXII)

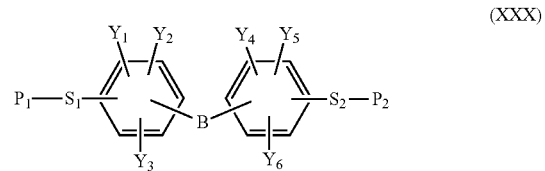

(XXX)

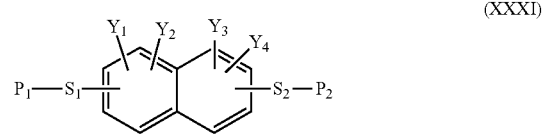

(XXXI)

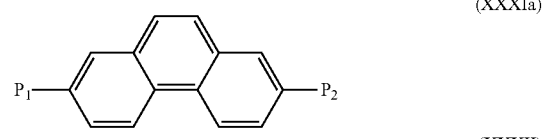

(XXXIa)

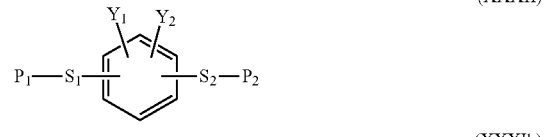

(XXXII)

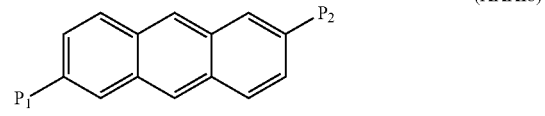

(XXXIb)

wherein $P_1$ and $P_2$ are independently from each other an acrylate, methacrylate, oxetane, maleinimide, allyl, allyloxy, vinyl, vinylamide, vinyloxy and epoxy group, epoxy derivatives, butoxy and butoxy derivatives,
B is a single bond, —CO—C(C$_1$-C$_6$alkoxy)$_2$-, —COO—, —OCO—,
$Y_1$, $Y_2$, $Y_3$, $Y_4$, $Y_5$, $Y_6$ are independently from each other hydrogen, a straight-chain or branched C$_1$-C$_{16}$alkyl group, which is unsubstituted or substituted by fluorine, di-(C$_1$-C$_{16}$alkyl)amino, C$_1$-C$_{15}$alkyloxy, nitro, nitrile and/or chlorine; and wherein one or more C-atom, CH— or CH$_2$— group may independently from each other be replaced by a linking group; halogen or nitrile; preferred substituents are C$_1$-C$_6$alkyl group, especially methyl or ethyl, C$_1$-C$_6$alkoxy group, especially methoxy or ethoxy, chlorine, fluorine, or nitrile, more preferably methoxy, chlorine, fluorine, or CN and most preferably methoxy, chlorine or fluorine; further, if the aromatic group is substituted, then it is preferably substituted once or twice;

$S_1$, $S_2$, are independently from each other a single bond or a spacer unit, which is preferably a straight-chain or branched, substituted or unsubstituted $C_1$-$C_{24}$alkylen, in which one or more, preferably non-adjacent, C-atom, CH— or $CH_2$—, group may be replaced by a linking group within the above given meaning and preferences, and, preferably replaced by is a single bond, —O—, —O(CO), —S—, —(CO)O— or

—$NR^2$—, and wherein the substituent is preferably at least one $C_1$-$C_6$alkyl, preferably methyl.

In formulae (XXX) and (XXXII) a substituent group for the benzene ring is present at the o-position, m-position, or p-position. In formula (XXXI), a substituent group for the naphthalene ring is present at the o-position, m-position, p-position, ana-position, E (epi)-position, kata-position, pen-position, pros-position, amphi-position, or 2,7-position. The substituent group for the benzene ring is preferably present at the p-position among the above positions. The substituent group for the naphthalene ring is preferably present at the amphi-position among the above positions. Preferred are:

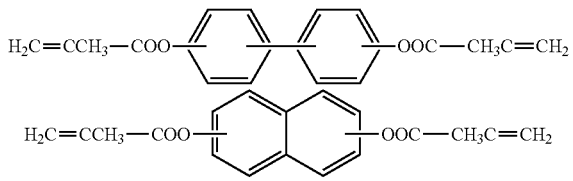

In general the liquid crystals compositions or liquid crystal layers are not particularly limited, provided that they contain the mono- or/and multi-polymerizable monomer described above. The liquid crystals compositions or liquid crystal layers can thus be made of any of various liquid crystal materials that have been known publicly. The liquid crystals compositions or liquid crystal layers may be made of a liquid crystal material identical to or different from that for display use.

The oligomer, which is the polymerized form of the polymerizable monomer, is in general not limited to any molecular weight. Preferably the molecular weight is in the range of 200 to 5000 Dalton, more preferably in the range of 500 to 2000 Dalton and most preferred in the range of 500 to 1000 Dalton.

The method for producing the liquid crystal display panel may involve using a polymerization initiator, such as methyl ethyl ketone peroxide and a benzoyl ether-based compound.

Preferably, the present invention relates to a method for manufacturing a liquid crystal display comprising applying at least a single LCP onto a polymer, homo- or copolymer or oligomer layer, preferably the orientation film, and polymerizing said LCP.

In general the polymerization is conducted by irradiation or at elevated temperature.

The LCP may be supplied (applied) onto the orientation films in any amount, so the amount is not particularly limited. The amount may be set as appropriate in accordance with, for example, respective thicknesses of the LCP polymer films formed by polymerization of the monomeric LCP. Further, preferably, the present invention relates to a method for manufacturing a liquid crystal display comprising bringing into contact a liquid crystal composition comprising a polymerizable monomer according to the present invention, or a polymer or oligomer, which is the polymerized form of said polymerizable monomer; with
at least a single orientation layer according to the present invention, preferably two orientation layers facing each other; and polymerising said polymerizable monomer.

Generally the polymerization methods are not limited so far as they have no adverse effects on the manufactured device. Preferably the polymerization is conducted by irradiation, especially UV radiation, or by heat.

The present invention further very especially preferably relates to an optical or electrooptical device unstructured or structured elements, especially a LCD, comprising a pair of substrates facing each other; wherein the substrates being provided with a pair of orientation layers according to the present invention and
a) optionally, a LCP polymer film, wherein said polymer film is formed on that orientation layer, or
b) a liquid crystal composition, preferably comprising a polymer made from at least a polymerizable monomer as described above, which liquid crystal composition is sandwiched between the pair of orientation layers.

The present invention further relates preferably to optical and electro-optical unstructured or structured constructional elements, preferably liquid crystal display cells, multi-layer and hybrid layer elements, comprising at least one polymer layer, copolymer or oligomer layer according to the present invention.

The present invention the wording optical or electro-optical elements has preferably the meaning of multilayer systems, or devices for the preparation of
a display waveguide, a security or brand protection element, a bar code, an optical grating, a filter, a retarder, a compensation film, a reflectively polarizing film, an absorptive polarizing film, an anisotropically scattering film compensator and retardation film, a twisted retarder film, a cholesteric liquid crystal film, a guest-host liquid crystal film, a monomer corrugated film, a smectic liquid crystal film, a polarizer, a piezoelectric cell, a thin film exhibiting non linear optical properties, a decorative optical element, a brightness enhancement film, a component for wavelength-band-selective compensation, a component for multi-domain compensation, a component of multiview liquid crystal displays, an achromatic retarder, a polarization state correction/adjustment film, a component of optical or electro-optical sensors, a component of brightness enhancement film, a component for light-based telecommunication devices, a G/H-polarizer with an anisotropic absorber, a reflective circular polarizer, a reflective linear polarizer, a MC (monomer corrugated film), twisted nematic (TN) liquid crystal displays, hybrid aligned nematic (HAN) liquid crystal displays, electrically controlled birefringence (ECB) liquid crystal displays, supertwisted nematic (STN) liquid crystal displays, optically compensated birefringence (OCB) liquid crystal displays, pi-cell liquid crystal displays, PLS technology (plane to line switching), PS-IPS (polymer stabilized IPS), in-plane switching (IPS) liquid crystal displays, such as IPS modes: like S-IPS (Super IPS), AS-IPS (Advanced super IPS), E-IPS (Enhanced IPS), H-IPS (Horizontal IPS), UH-IPS, S-IPS II, e-IPS, p-IPS (performance IPS); CH-IPS mode (Chiral hybrid in plane switching); Field induced photoreactive alignment IPS, fringe field switching (FFS) liquid crystal displays; (FPA) field-induced photo-reactive alignment; hybrid FPA; VA-IPS mode liquid crystal displays, or displays using blue phase liquid crystals; all above display types are applied in either transmissive or reflective or transflective mode.

More preferred optical or electro-optical elements are PLS technology (plane to line switching), PS-IPS (polymer stabilized IPS), in-plane switching (IPS) liquid crystal displays, such as IPS modes like S-IPS (Super IPS), AS-IPS (Advanced super IPS), E-IPS (Enhanced IPS), H-IPS (Horizontal IPS), UH-IPS, S-IPS II, e-IPS, p-IPS (performance IPS); Field induced photoreactive alignment IPS, fringe field switching (FFS) liquid crystal displays; (FPA) field-induced photo-reactive alignment; hybrid FPA; VA-IPS mode liquid crystal displays, or displays using blue phase liquid crystals; all above display types are applied in either transmissive or reflective or transflective mode.

The advantages of the present invention could not be foreseen by a skilled person.

It has surprisingly been found, that in addition to the polymer backbone, the introduction of a polar group into the polymer side groups having specific molecular architecture plays a predominant role in obtaining materials for the planar orientation of liquid crystals, having optimised properties, such as good or medium aligning quality.

EXAMPLES

Definitions Used in the Examples $^1$H NMR: $^1$H nuclear magnetic resonance spectroscopy
DMSO-$d_6$: dimethylsulfoxide deuterated
300 MHz: 300 Megahertz
M: multiplett
D: doublet
Dd: doublet doublet
t: triplet
s: singlet
q: quadruplet
qi: quintet
br: broad
HCl: hydrogen chloride
HCl solution (25%): volume percent
NaOH: sodium hydroxide
NaOH (30%): weight percent
MeOH: methanol
EtOAc: ethyl acetate
NMP: N-methyl-2-pyrrolidone
THF: tetrahydrofuran
TBME: tert. butyl methyl ether
DMF: N,N-dimethylformamide
DBU: 1,8-Diazabicyclo[5.4.0]undec-7-ene
NaHCO$_3$: sodium bicarbonate H$_2$SO$_4$: sulphuric acid
RT: room temperature, usually in the range of 18° C. to 28° C.
[η]: viscosity
v.t. %: volume percent
MLC3005: is a mixture of liquid crystal available from Merck KGA with a Dielectric anisotropy of 5.1, an optical anisotropy of 0.0995 and a rotational viscosity of 56 m·Pa·s.

Example 1

Preparation of 6-{2-methoxy-4[(1E)-3-methoxy-3-oxoprop-1-enyl]phenoxy}hexyl 3,5-diaminobenzoate 1.1-Preparation of methyl(2E)-3-(4-hydroxy-3-methoxyphenyl)prop-2-enoate

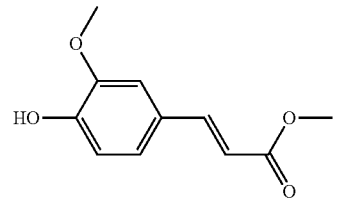

20 g (103 mmol) of (2E)-3-(4-hydroxy-3-methoxyphenyl)prop-2-enoic acid is dissolved in 206 mL of MeOH. 2.8 mL (52 mmol) of concentrated H$_2$SO$_4$ is added in one portion. The solution is allowed to react at 90° C. for 2 hours. The reaction mixture is then cooled down and poured to icy water. The aqueous layer is extracted three times with 100 mL of TBME. Combined organic layers are washed with 200 mL of a NaHCO$_3$ saturated solution. The organic phase is then dried over sodium sulfate, filtrated and concentrated under reduced pressure. The product is dried under vacuum to give 21.4 g (100%) of (2E)-3-(4-hydroxy-3-methoxyphenyl)prop-2-enoate as a white powder used without further purification.

1.2-Preparation of methyl(2E)-3-{4-[(6-hydroxyhexyl)oxy]-3-methoxyphenyl}prop-2-enoate

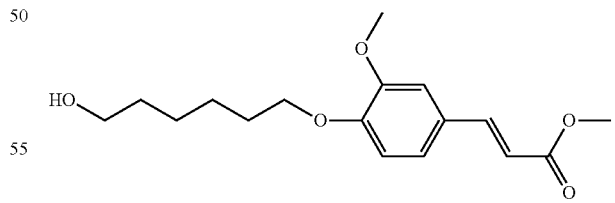

22 g (106 mmol) of (2E)-3-(4-hydroxy-3-methoxyphenyl)prop-2-enoate and 15.5 g (114 mmol) of 6-chlorohexan-1-ol are dissolved in 70 mL of DMF. 18.5 g (134 mmol) of potassium carbonate and 1.7 g (10 mmol) of potassium iodide are added and the suspension is heated up to 100° C. for 24 hours. The reaction mixture is cooled down to room temperature and is poured to icy water. A 25% HCl solution is added and the precipitate is filtered off. The residue is purified on column chromatography using toluene: ethylacetate 2:1 as eluant to yield 24.1 g (74%) of (2E)-3-{4-[(6-hydroxyhexyl)oxy]-3-methoxyphenyl}prop-2-enoate as a white powder.

1.3-Preparation of 6-{2-methoxy-4-[(1E)-3-methoxy-3-oxoprop-1-enyl]phenoxy}hexyl 3,5-dinitrobenzoate

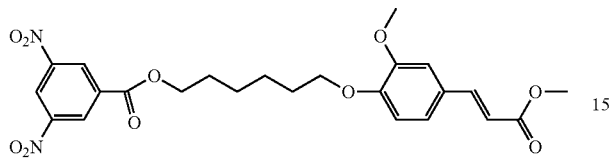

17.9 g (78 mmol) of 3,5-dinitrobenzoyl chloride is dissolved in 147 mL toluene and 20 drops DMF are incorporated. 24 g (78 mmol) of (2E)-3-{4-[(6-hydroxyhexyl)oxy]-3-methoxyphenyl}prop-2-enoate, 0.475 g (4 mmol) of 4-dimethylaminopyridine and 9.23 g (117 mmol) of pyridine are added. The mixture is stirred at room temperature for 96 hours. The solution is then heated up to 60° C. and 58 ml of MeOH are added. The suspension is stirred at room temperature for 1 hour and at 0° C. for 1 hour. The precipitate is filtered off. Chromatography of the residue using toluene:ethyl acetate 19:1 following by toluene: ethyl acetate 9:1; yield 25 g (64%) of pure 6-{2-methoxy-4-[(1E)-3-methoxy-3-oxoprop-1-enyl]phenoxy}hexyl 3,5-dinitrobenzoate as an orange powder.

1.4-Preparation of 6-{2-methoxy-4-[(1E)-3-methoxy-3-oxoprop-1-enyl]phenoxy}hexyl 3,5-diaminobenzoate

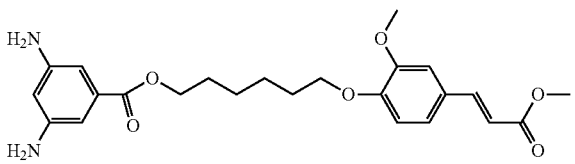 [SMILES: COC(=O)/C=C/c1ccc(OCCCCCCOC(=O)c2cc(N)cc(N)c2)c(OC)c1]

5 g (9.7 mmol) of 6-{2-methoxy-4-[(1E)-3-methoxy-3-oxoprop-1-enyl]phenoxy}hexyl 3,5-dinitrobenzoate are dissolved in a mixture of 84 ml of DMF and 9 ml of water. 15.7 g (58 mmol) of ferric chloride hexahydrate are added. 6.31 g (97 mmol) of zinc powder are added portionwise within 30 min. The mixture is allowed to react for 2 hours. The reaction mixture is then partitioned between ethyl acetate and water and filtered. The organic phase is washed repeatedly with water, dried over sodium sulfate, filtered and concentrated by rotary evaporation. Filtration of the residue on silica gel using toluene:ethyl acetate (1:3) as eluant and yields 2.7 g (61%) of 6-{2-methoxy-4-[(1E)-3-methoxy-3-oxoprop-1-enyl]phenoxy}hexyl 3,5-diaminobenzoate as a white powder.

$^1$H NMR (300 MHz) in DMSO-$d_6$: 7.57 (d, 1H), 7.35 (d, 1H), 7.22 (dd, 1H), 6.97 (d, 1H), 6.54 (d, 1H), 6.43 (d, 2H), 6.02 (t, 1H), 4.99 (s, 4H), 4.18 (t, 2H), 3.97 (t, 2H), 3.80 (s, 3H), 3.65 (s, 3H), 1.70 (m, 4H), 1.45 (m, 4H)

Example 2

Preparation of 4-{(1E)-3-[2-(2,4-diaminophenyl)ethoxy]-3-oxoprop-1-enyl}phenyl 4-(3-nitrilepropoxy)benzoate

2.1-Preparation of 4-(3-nitrilepropoxy)benzoic acid

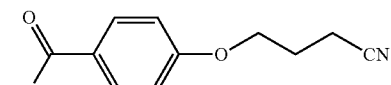

46.8 g (307 mmol) of methyl-4-hydroxybenzoate, 50 g (338 mmol) of 4-bromobutanenitrile are dissolved in 535 mL of NMP. 5.1 g (31 mmol) of potassium iodide and 128 g (93 mmol) of potassium carbonate are added and the suspension is heated up to 80° C. After 48 h, a mixture of 15 g of sodium hydroxide and 49 ml of water is added. The reaction mixture is heated up to 100° C. for 5 hours. Then the solution is cooled down and 480 mL of water is added. The aqueous layer is removed and the organic layer is poured to 1.5 L of icy water. 81 mL of a 25% HCl solution is added. The precipitate is filtered off and washed with 250 mL of water. The resulting product is incorporated in 600 mL of MeOH. The suspension is then stirred for 1 hour and filtered off to give 50.1 g (80%) of 4-(3-nitrilepropoxy)benzoic acid as a white powder used without further purification.

2.2-Preparation of (2E)-3-(4-{[4-(3-nitrilepropoxy)benzoyl]oxy}phenyl)prop-2-enoic acid

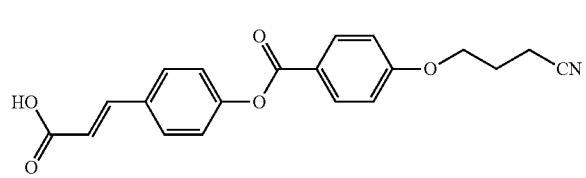 [SMILES: N#CCCCOc1ccc(C(=O)Oc2ccc(/C=C/C(=O)O)cc2)cc1]

16.8 g (82 mmol) of 4-(3-nitrilepropoxy)benzoic acid is suspended in 56 mL of toluene and few drops of DMF are added. The suspension is heated up to 75° C. and 10.7 g (90 mmol) of thionylchloride are added. After 2 hours, the excess of thionyl chloride is removed under pressure. The solution is cooled down to room temperature. 10.2 g (83 mmol) of 4-hydroxybenzaldehyde 0.5 g (4 mmol) of 4-diaminopyridine and 28 g (355 mmol) of pyridine are added. After 3 hours, 14.5 g (140 mmol) of malonic acid and 3 g (42 mmol) of pyrrolidine are added. The reaction mixture is allowed to react at 80° C. for 30 min. 16.8 mL of MeOH are then incorporated and the suspension is cooled down and kept at 0° C. for 1 hour. The product is filtered off and suspended for 2 hours in a solution of 57 mL of MeOH, 11 mL of water and 7.5 g of a 25% HCL solution. The solid is filtered off and washed with MeOH and heptane. The product is crystallized in acetonitrile to give 23 g (80%) of (2E)-3-(4-{[4-(3-nitrilepropoxy)benzoyl]oxy}phenyl)prop-2-enoic acid as a white powder.

2.3-Preparation of 2-(2,4-dinitrophenyl)ethanol

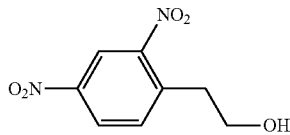 [SMILES: O=[N+]([O-])c1ccc(CCO)c([N+](=O)[O-])c1]

22.6 g (100 mmol) of 2,4-dinitrophenylacetic acid is dissolved in 150 mL of THF and added dropwise in 2 hours to 300 mL of a borane (BH$_3$)-THF complex 1.0 M solution in THF. After 3 hours at 25° C., 200 ml of water are added. The reaction mixture is then poured to ethyl acetate and water. The organic phase is washed repeatedly with water and dried over sodium sulphate, filtered and concentrated under pressure. Chromatography of the residue using toluene:ethyl acetate 1:1 as eluant and crystallization in ethylacetate/hexane yields 20.7 g (98%) of 2-(2,4-dinitrophenyl)ethanol as yellowish crystal.

2.4-Preparation of 4-{(1E)-3-[2-(2,4-dinitrophenyl)ethoxy]-3-oxoprop-1-enyl}phenyl 4-(3-nitrilepropoxy)benzoate

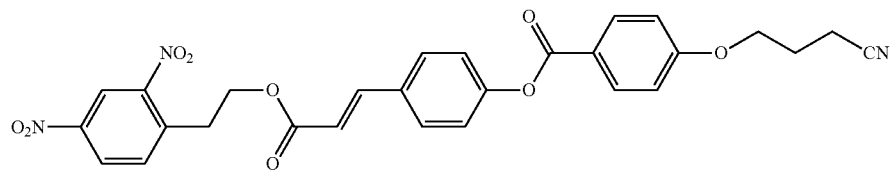 [SMILES: N#CCCCOc1ccc(C(=O)Oc2ccc(/C=C/C(=O)OCCc3ccc(N)cc3N)cc2)cc1]

21.1 g (60 mmol) of (2E)-3-(4-{[4-(3-nitrilepropoxy)benzoyl]oxy}phenyl)prop-2-enoic acid, 12.7 g (60 mmol) of 2-(2,4-dinitrophenyl)ethanol, 0.366 g of 4-dimethylaminopyridine are dissolved in 120 mL of dichloromethane. 12.6 g (66 mmol) of N-(3-Dimethylaminopropyl)-N'-ethylcarbodiimide hydrochloride (EDC hydrochloride) are added at 0° C. The solution is stirred for 1 h at 0° C. and allowed to stir at room temperature overnight. After 22 hours at room temperature, the reaction mixture is partitioned between dichloromethane and water. The organic phase is washed repeatedly with water, dried over sodium sulphate, filtered and concentrated by rotary evaporation. The product is dried at 40° C. under vacuum to yield 29.2 g (89%) of 4-{(1E)-3-[2-(2,4-dinitrophenyl)ethoxy]-3-oxoprop-1-enyl}phenyl 4-(3-nitrilepropoxy)benzoate as a yellowish powder.

2.5-Preparation of 4-{(1E)-3-[2-(2,4-diaminophenyl)ethoxy]-3-oxoprop-1-enyl}phenyl 4-(3-nitrilepropoxy)benzoate

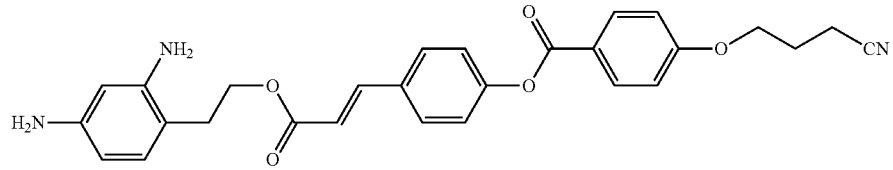

4-{(1E)-3-[2-(2,4-diaminophenyl)ethoxy]-3-oxoprop-1-enyl}phenyl 4-(3-nitrilepropoxy)benzoate is prepared in analogy to 6-{2-methoxy-4-[(1E)-3-methoxy-3-oxoprop-1-enyl]phenoxy}hexyl 3,5-diaminobenzoate (as described in Example 1) with the proviso that 6-{2-methoxy-4-[(1E)-3-methoxy-3-oxoprop-1-enyl]phenoxy}hexyl 3,5-dinitrobenzoate is replaced by 4-{(1E)-3-[2-(2,4-dinitrophenyl)ethoxy]-3-oxoprop-1-enyl}phenyl 4-(3-nitrilepropoxy)benzoate $^1$H NMR (300 MHz) in DMSO-$d_6$: 8.10 (d, 2H), 7.83 (d, 2H), 7.69 (d, 1H), 7.33 (d, 2H), 7.15 (d, 2H), 6.65 (d, 1H), 6.61 (d, 1H), 5.91 (d, 1H), 5.81 (dd, 1H), 4.65 (s, 4H), 4.18 (m, 4H), 2.69 (t, 4H), 2.08 (qi, 2H).

Example 3

4-{(1E)-3-[(4,4'-diamino-2'-{[(3E)-4-(4-{[4-(3-nitrilepropoxy)benzoyl]oxy}phenyl)-2-oxobut-3-enyl]oxy}-1,1'-biphenyl-2-yl) methoxy]-3-oxoprop-1-enyl}phenyl 4-(3-nitrilepropoxy)benzoate

3.1-Preparation of 4,4'-Dinitro-1,1'-biphenyl-2,2'-dicarboxylic acid

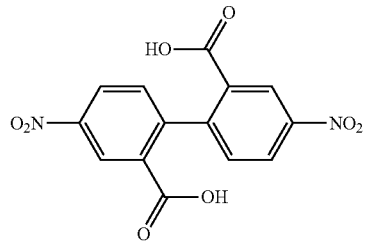 [SMILES: O=C(O)c1cc([N+](=O)[O-])ccc1-c1ccc([N+](=O)[O-])cc1C(=O)O]

30.0 g (124 mmol) diphenic acid are dissolved at room temperature in 469 g (4.59 mol) concentrated sulfuric acid (96%). The solution is cooled to −15° C. and a mixture of 92.4 g (1000 mmol) of concentrated nitric acid (69%) and 12.0 g (117 mmol) of concentrated sulfuric acid (96%) is added slowly so that the mixture temperature is maintained below 0° C. After the addition the solution is allowed to react at room temperature for 24 hours. The mixture is then poured onto crushed ice. The precipitate is collected by filtration, washed with water and dried at room temperature under vacuum for 10 hours to yield 39.1 g (95%) of 4,4'-Dinitro-1,1'-biphenyl-2,2'-dicarboxylic acid as a white powder.

3.2-Preparation of 4,4'-Dinitro-1,1'-biphenyl-2,2'-dimethanol

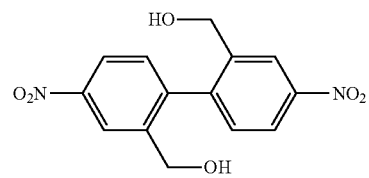 [SMILES: O=[N+]([O-])c1ccc(-c2ccc([N+](=O)[O-])cc2CO)c(CO)c1]

80 g (241 mmol) 4,4'-Dinitro-1,1'-biphenyl-2,2'-dicarboxylic acid is dissolved in 225 ml THF and added dropwise in the course of 1 hour to 1.4 L (1440 mmol) of a borane(BH$_3$)-tetrahydrofuran complex 1.0 M solution in THF. After 19 hours at 25° C., 500 ml of water are carefully added. After 1 hour, the solution is acidified to pH=1-2 with 30 ml of 1N HCl solution and allowed to stir for 30 min. The reaction mixture is then partitioned between ethyl acetate and water. The organic phase is washed repeatedly with water, dried over sodium sulfate, filtered and concentrated by rotary evaporation. The residue, 48 g (66%) of 2,2'-bis(hydroxymethyl)-4,4'-dinitro-1,1'-biphenyl as white powder is used without further purification.

3.3-Preparation of 4-{(1E)-3-[(2'-{[(3E)-4-(4-{[4-(3-nitrilepropoxy)benzoyl]oxy}phenyl)-2-oxobut-3-enyl]oxy}-4,4'-dinitro-1,1'-biphenyl-2-yl)methoxy]-3-oxoprop-1-enyl}phenyl 4-(3-nitrilepropoxy)benzoate

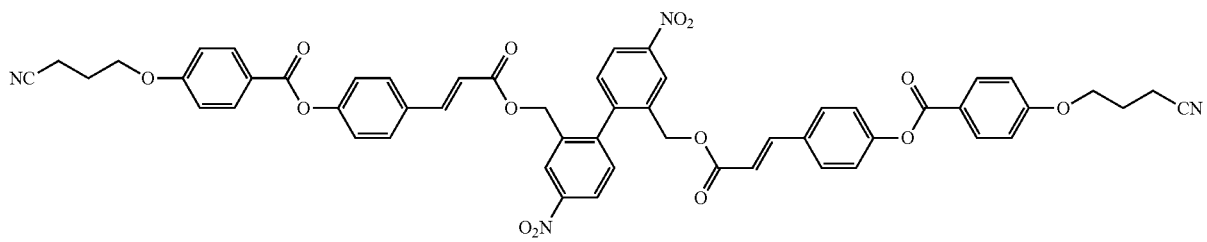

4-{(1E)-3-[(2'-{[(3E)-4-(4-{[4-(3-nitrilepropoxy)benzoyl]oxy}phenyl)-2-oxobut-3-enyl]oxy}-4,4'-dinitro-1,1'-biphenyl-2-yl)methoxy]-3-oxoprop-1-enyl}phenyl 4-(3-nitrilepropoxy)benzoate is prepared in analogy to 4-{(1E)-3-[2-(2,4-dinitrophenyl)ethoxy]-3-oxoprop-1-enyl}phenyl 4-(3-nitrilepropoxy)benzoate (as described in Section 2-4 of Example 2) with the proviso that 2-(2,4-dinitrophenyl)ethanol is replaced by 4,4'-dinitro-1,1'-biphenyl-2,2'-dimethanol as described in Section 3.2 of Example 3.

3.4-Preparation of 4-{(1E)-3-[(4,4'-diamino-2'-{[(3E)-4-(4-{[4-(3-nitrilepropoxy)benzoyl]oxy}phenyl)-2-oxobut-3-enyl]oxy}-1,1'-biphenyl-2-yl)methoxy]-3-oxoprop-1-enyl}phenyl 4-(3-nitrilepropoxy)benzoate

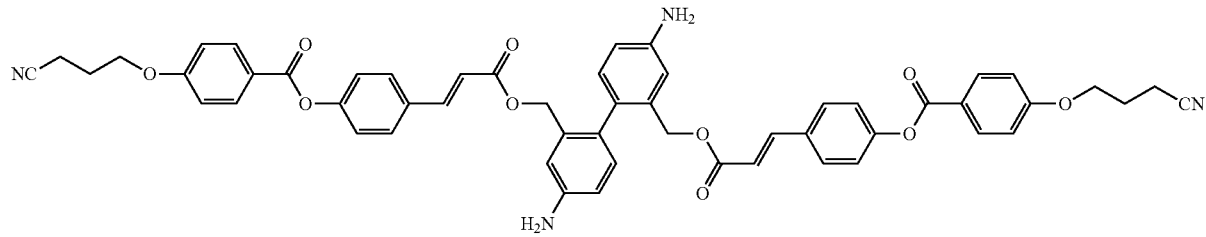 [SMILES: N#CCCCOc1ccc(C(=O)Oc2ccc(/C=C/C(=O)OCc3cc(N)ccc3-c3ccc(N)cc3COC(=O)/C=C/c3ccc(OC(=O)c4ccc(OCCCC#N)cc4)cc3)cc2)cc1]

4-{(1E)-3-[(4,4'-diamino-2'-{[(3E)-4-(4-{[4-(3-nitrilepropoxy)benzoyl]oxy}phenyl)-2-oxobut-3-enyl]oxy}-1,1'-biphenyl-2-yl)methoxy]-3-oxoprop-1-enyl}phenyl 4-(3-nitrilepropoxy)benzoate is prepared from 4-{(1E)-3-[(2'-{[(3E)-4-(4-{[4-(3-nitrilepropoxy)benzoyl]oxy}phenyl)-2-oxobut-3-enyl]oxy}-4,4'-dinitro-1,1'-biphenyl-2-yl)methoxy]-3-oxoprop-1-enyl}phenyl 4-(3-nitrilepropoxy)benzoate in analogy to 6-{2-methoxy-4-[(1E)-3-methoxy-3-oxoprop-1-enyl]phenoxy}hexyl 3,5-diaminobenzoate (Example 1)

$^1$H NMR (300 MHz) in DMSO-d$_6$: 8.06 (d, 4H), 7.77 (d, 4H), 7.62 (d, 2H), 7.29 (d, 4H), 7.13 (d, 4H), 6.84 (d, 2H), 6.71 (d, 2H), 6.57 (d, 2H), 6.56 (dd, 2H), 5.18 (s, 4H), 4.84 (s, 4H), 4.15 (t, 4H), 2.68 (t, 4H), 2.07 (qi, 4H).

Example 4

6-{[(2E)-3-(4-{[4-(2-methoxyethoxy)benzoyl]oxy}phenyl)prop-2-enoyl]oxy}hexyl 3,5-diaminobenzoate 4.1-Preparation of methyl 4-(2-methoxyethoxy)benzoate

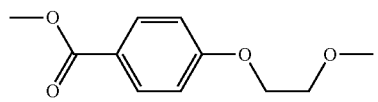

4.3 mL (37.5 mmol) of methoxyethanol and 10.1 g (37.5 mmol) of triphenylphosphine are added to a solution of 61 g (30 mmol) of methyl 4-hydroxybenzoate in 120 ml of THF at room temperature. 7.7 mL (37.5 mmol) of diisopropyl azodicarboxylate (DIAD) in 110 mL of THF are incorporated slowly so that the temperature is maintained to 10° C. After 18 hours at room temperature, the reaction mixture is poured onto icy water and acidified with a 1N HCl solution. The aqueous phase is extracted with ethyl acetate and the organic phase is then washed repeatedly with water, dried over sodium sulfate, filtered and concentrated by rotary evaporation. Chromatography of the residue using cyclohexane:ethyl acetate 4:1 yielded 6.6 g (98%) of pure methyl 4-(2-methoxyethoxy)benzoate as a white powder.

4.2-Preparation of 4-(2-methoxyethoxy)benzoic acid

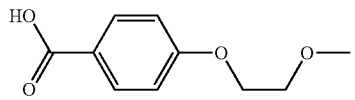

4.3 g (64.95 mmol) of potassium hydroxide is added to a solution of 6.1 g (29 mmol) of methyl 4-(2-methoxyethoxy)benzoate in 100 mL of EtOH. The solution is heated up to reflux for one hour and poured onto icy water and acidified with a 25% HCl solution. The mixture is filtered off and washed 2 times with 100 mL of water. The solid is suspended in 100 ml of acetonitrile for 1 hour and the precipitate is filtered off and dried under pressure to yield 3.9 g (70%) of pure 4-(2-methoxyethoxy)benzoic acid as a white powder.

4.3-Preparation of (2E)-3-{4-[(ethoxycarbonyl)oxy]phenyl}prop-2-enoic acid

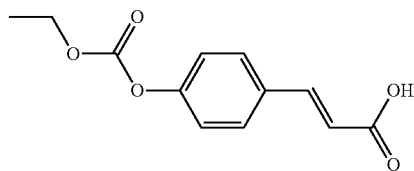 [SMILES: CCOC(=O)Oc1ccc(/C=C/C(=O)O)cc1]

67 g (400 mmol) of (2E)-3-(4-hydroxyphenyl)prop-2-enoic acid is added to a mixture of 57.4 g (880 mmol) of potassium hydroxide in 600 ml at 0° C. 46.6 mL (480 mmol) of ethyl chloridocarbonate are added dropwise so that the temperature is maintained to 10° C. The reaction mixture is subsequently allowed to react for 2 hours at 25° C. and then acidified to pH=1 with 200 mL of a 25% HCl solution—The precipitate is filtered off and washed with 500 mL of water. The residue is crystallized in 2 L of toluene and dried under vacuum to yield 79 g (74%) of pure (2E)-3-{4-[(ethoxycarbonyl)oxy]phenyl}prop-2-enoic acid as a white powder.

4.4-Preparation of 6-chlorohexyl(2E)-3-{4-[(ethoxy-carbonyl)oxy]phenyl}prop-2-enoate

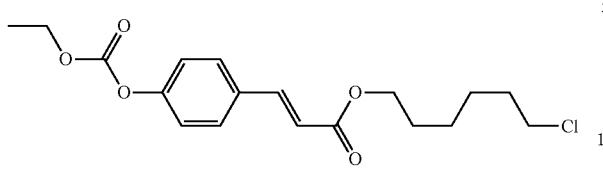

69.2 g (343 mmol) of N-(3-Dimethylaminopropyl)-N'-ethylcarbodiimide hydrochloride (EDC hydrochloride) is added to a solution of 95.4 g (343 mmol) of (2E)-3-{4-[(ethoxycarbonyl)-oxy]phenyl}prop-2-enoic acid, 4.27 g (34.3 mmol) of 4-dimethylaminopyridine in 1.5 L of dichloromethane at 0° C. To this mixture, 46.7 mL (343 mmol) of chlorohexanol in 100 mL of dichloromethane are incorporated at 10° C. The solution is allowed to stir at room temperature for 22 hours. The reaction mixture is then partitioned between dichloromethane and water. The organic phase is washed repeatedly with water, dried over sodium sulphate, filtered and concentrated by rotary evaporation. Chromatography of the residue using toluene yields 89.3 g (72%) of pure 6-chlorohexyl(2E)-3-{4-[(ethoxycarbonyl)oxy]phenyl}prop-2-enoate as a white powder.

4.5-Preparation of 6-Chlorohexyl(2E)-3-(4-hydroxyphenyl)prop-2-enoate

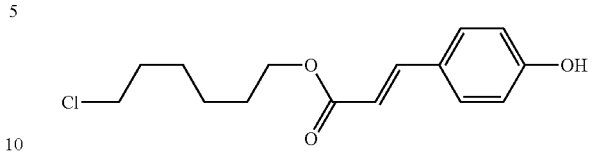

A NH$_3$ 25 v.t. % solution diluted in 780 mL of acetone is added dropwise to a solution of 89.3 g (247 mmol) of 6-chlorohexyl(2E)-3-{4-[(ethoxycarbonyl)oxy] phenyl}prop-2-enoate in 752 mL of pyridine. The mixture is allowed to stir for 20 hours at room temperature. The reaction mixture is then partitioned between ethyl acetate and water. The organic phase is then washed repeatedly with water, dried over sodium sulfate, filtered off and concentrated by rotary evaporation. The solid is dried under vacuum to yield 70 g (100%) of pure 6-chlorohexyl(2E)-3-(4-hydroxyphenyl)prop-2-enoate as a white powder.

4.6-Preparation of 4-{(1E)-3-[(6-chlorohexyl)oxy]-3-oxoprop-1-enyl}phenyl 4-(2-methoxyethoxy)benzoate

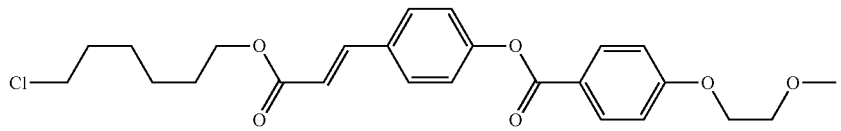

4.7-Preparation of 6-{[(2E)-3-(4-{[4-(2-methoxyethoxy)benzoyl]oxy}phenyl)prop-2-enoyl]oxy}hexyl 3,5-dinitrobenzoate 3 g (15 mmol) of N-(3-Dimethylaminopropyl)-N'-ethyl-carbodiimide hydrochloride (EDC hydrochloride) is added to a solution of 3.1 g (15 mmol) of 6-chlorohexyl(2E)-3-(4-hydroxyphenyl)prop-2-enoate, 0.186 g (1.5 mmol) of 4-dimethylaminopyridine in 70 mL of dichloromethane at 0° C. To this mixture, 5.1 g (15 mmol) of 4-(2-methoxyethoxy) benzoic acid in 40 mL of dichloromethane is added at 10° C. The solution is allowed to stir at room temperature for 22 hours. The reaction mixture is then partitioned between dichloromethane and water. The organic phase is washed repeatedly with water, dried over sodium sulphate, filtered and concentrated by rotary evaporation. Chromatography of the residue using cyclohexane:ethylacetate 4:1 yielded 5.3 g (73%) of pure 4-{(1E)-3-[(6-chlorohexyl)oxy]-3-oxoprop-1-enyl}phenyl 4-(2-methoxyethoxy)benzoate as a white powder.

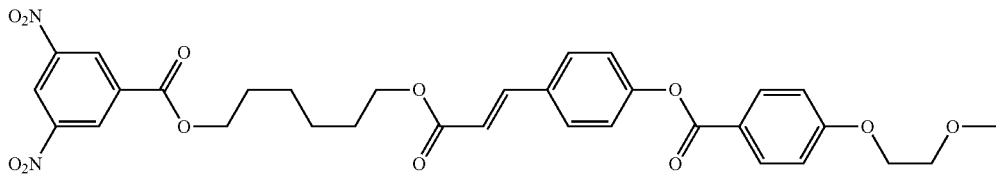

5.3 g (11 mmol) of 4-{(1E)-3-[(6-chlorohexyl)oxy]-3-oxoprop-1-enyl}phenyl 4-(2-methoxyethoxy)benzoate in 20 mL DMF is added dropwise to a solution of 2 g (13.1 mmol) of 3,5 diaminobenzoic acid and 2.1 mL (14.2 mmol) of DBU in 20 ml of DMF. The mixture is allowed to stir at 80° C. for 24 hours and partitioned between icy water and ethyl acetate. The organic phase is dried over sodium sulphate, filtered off and concentrated by rotary evaporation. Chromatography of the residue using cyclohexane:ethyl acetate 1:2 as eluant yields 2.6 g (44%) of pure 6-{[(2E)-3-(4-{[4-(2-methoxyethoxy)benzoyl]oxy}phenyl)prop-2-enoyl]oxy}hexyl 3,5-dinitrobenzoate as a white powder.

4.8-Preparation of 6-{[(2E)-3-(4-{[4-(2-methoxy-ethoxy)benzoyl]oxy}phenyl)prop-2-enoyl]oxy}hexyl 3,5-diaminobenzoate

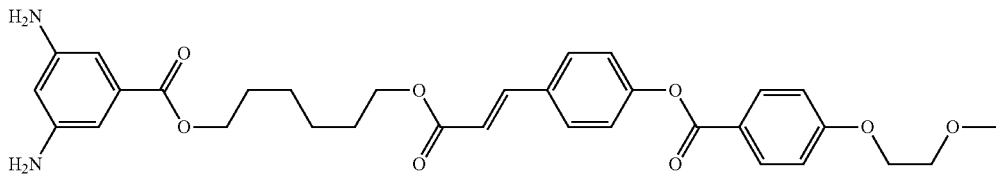 [SMILES: COCCOc1ccc(C(=O)Oc2ccc(/C=C/C(=O)OCCCCCCOC(=O)c3cc(N)cc(N)c3)cc2)cc1]

6-{[(2E)-3-(4-{[4-(2-methoxyethoxy)benzoyl]oxy}phenyl)prop-2-enoyl]oxy}hexyl 3,5-diamino benzoate is prepared from 6-{[(2E)-3-(4-{[4-(2-methoxyethoxy)benzoyl]oxy}phenyl)prop-2-enoyl]oxy}hexyl 3,5-dinitrobenzoate in analogy to 6-{2-methoxy-4-[(1E)-3-methoxy-3-oxoprop-1-enyl]phenoxy}hexyl 3,5-diaminobenzoate (as described in Example 1)

$^1$H NMR (300 MHz) in CDCl$_3$: 8.13 (d, 2H), 7.69 (d, 1H), 7.58 (d, 2H), 7.22 (d, 2H), 7.01 (d, 2H), 6.77 (d, 2H), 6.41 (d, 1H), 6.17 (t, 1H), 4.28 (t, 2H), 4.22 (m, 4H), 3.80 (t, 2H), 3.67 (s, 4H), 3.47 (s, 3H), 1.77 (m, 4H), 1.50 (m, 4H).

Example 5

Polymerisation Step: Formation of Polyamic Acid (PAA)

Preparation of PAA-1 from Diamine of Example 1

0.666 g (3.4 mmol) of 1,2,3,4-cyclobutanetetracarboxylic acid is added to a solution of 1.5 g (3.4 mmol) of 6-{2-methoxy-4-[(1E)-3-methoxy-3-oxoprop-1-enyl] phenoxy}hexyl 3,5-diaminobenzoate in 8.6 g of NMP. Stirring is then carried out at 0° C. for 2 hours. The mixture is subsequently allowed to react for 21 hours at room temperature. The polymer mixture is diluted with 50 mL of NMP, precipitated into 300 mL of water to yield, after drying at 40° C. under vacuum, 2.1 g of polyamic acid PAA-1 in the form of a white powder.

[η]=0.40 dL/g $^1$H NMR (300 MHz) in DMSO-d$_6$: 12.47 (s, 2H), 10.4 (m, 2H), 8.34 (m, 1H), 8.01 (m, 2H), 7.55 (d, 1H), 7.32 (m, 1H), 7.19 (d, 1H), 6.96 (m, 1H), 6.52 (d, 1H), 4.28 (m, 2H), 3.98 (m, 2H), 3.89 (m, 1H), 3.79 (m, 6H), 3.75-3.55 (br., 3H), 1.73 (m, 4H), 1.46 (m, 4H).

Preparation of PAA-2 from Diamine of Example 2

PAA-2 is prepared from 4-{(1E)-3-[2-(2,4-diaminophenyl)ethoxy]-3-oxoprop-1-enyl}phenyl 4-(3-nitrilepropoxy)benzoate in analogy to PAA-1 to yield 2.1 g of polyamic acid PAA-2 in the form of a white powder.

[η]=0.20 dL/g $^1$H NMR (300 MHz) in DMSO-d6: 12.50 (s, 1.5H), 10.22 (m, 0.8H), 9.58 (m, 0.7H), 8.10 (m, 2H), 7.80 (m, 3H), 7.68 (m, 1H), 7.43 (m, 1H), 7.30 (m, 2H), 7.23 (m, 1H), 7.14 (m, 2H), 6.63 (m, 1H), 4.30 (m, 2H), 4.15 (m, 2H), 3.94-3.50 (br., 4H), 2.94 (m, 2H), 2.67 (m, 2H), 2.1 (m, 2H).

Preparation of PAA-3 from Diamine of Example 2

0.69 g (3.1 mmol) of 2,3,5-tricarboxycyclopentylacetic-1,2:3,4-dianhydride is added to a solution of 1.5 g (3.1 mmol) of 4-{(1E)-3-[2-(2,4-diaminophenyl)ethoxy]-3-oxoprop-1-enyl}phenyl 4-(3-nitrilepropoxy)benzoate in 5.1 g of NMP. Stirring is then carried out at 0° C. for 2 hours. The mixture is subsequently allowed to react for 48 hours at room temperature. The polymer mixture is diluted with 30 g of NMP, precipitated into 300 mL of water to yield, after drying at 40° C. under vacuum, 1.9 g of polyamic acid PAA-3 in the form of a white powder.

[η]=0.40 dL/g $^1$H NMR (300 MHz) in DMSO-d$_6$: 12.35 (s, 2H), 10.03 (m, 1H), 9.50 (m, 1H), 8.07 (m, 2H), 7.91-7.40 (br., 5H), 7.29 (m, 2H), 7.12 (m, 3H), 6.59 (m, 1H), 4.26 (m, 2H), 4.14 (m, 2H), 3.24-2.30 (m, 12H), 2.01 (m, 2H).

Preparation of PAA-4 from Diamine of Example 3

PAA-4 is prepared from 4-{(1E)-3-[(4,4'-diamino-2'-{[(3E)-4-(4-{[4-(3-nitrilepropoxy)benzoyl]oxy}phenyl)-2-oxobut-3-enyl]oxy}-1,1'-biphenyl-2-yl)methoxy]-3-oxoprop-1-enyl}phenyl 4-(3-nitrile propoxy)benzoate in analogy to PAA-3 to yield, in 24 hours, 0.950 g of PAA-4 as a white powder.

[η]=0.25 dL/g $^1$H NMR (300 MHz) in DMSO-d$_6$: 12.40 (s, 2H), 10.25 (m, 2H), 8.04 (m, 5H), 7.74 (m, 10H), 7.28 (m, 4H), 7.10 (m, 5H), 6.56 (m, 2H), 4.90 (m, 4H), 4.14 (m, 4H), 3.27-2.25 (m, 12H), 2.05 (m, 4H).

Preparation of PAA-5 from 4,4'-Ethylenedianiline 3.2 g (14.1 mmol) of 2,3,5-tricarboxycyclopentylacetic-1,2:3,4-dianhydride is added to a solution of 3 g (14.1 mmol)

of 4,4'-ethylenedianiline in 35 g of NMP. Stirring is then carried out at 0° C. for 2 hours. The polymer mixture is then diluted with 47 g of acetone, precipitated into 500 mL of water to yield, after drying at 40° C. under vacuum, 6.5 g of polyamic acid PAA-5 in the form of a white powder. [η]=0.52 dL/g $^1$H NMR (300 MHz) in DMSO-d$_6$: 12.31 (s, 1.5H), 9.97 (m, 2H), 7.45 (m, 4H), 7.11 (m, 4H), 3.26-2.24 (m, 12H).

Preparation of PAA-6 from 4,4'-Methylenedianiline 5.6 g (25.2 mmol) of 2,3,5-tricarboxycyclopentylacetic-1,2:3,4-dianhydride is added to a solution of 5 g (25.2 mmol) of 4,4'-methylenedianiline in 60 g of NMP. Stirring is then carried out at 0° C. for 2 hours. The mixture is subsequently allowed to react for 1 hour at room temperature. The polymer mixture is then diluted with 100 g of NMP and 78 g of acetone, precipitated into 3500 mL of water to yield, after drying at 40° C. under vacuum, 14 g of polyamic acid PAA-6 in the form of a white powder. [η]=0.52 dL/g $^1$H NMR (300 MHz) in DMSO-d6: 12.26 (m, 2H), 9.90 (m, 2H), 7.48 (m, 4H), 7.10 (m, 4H), 3.81 (m, 2H), 3.22-2.38 (m, 8H).

Preparation of PAA-7 from Example 4

PAA-7 is prepared from 0.950 g (1.5 mmol) 6-{[(2E)-3-(4-{[4-(2-methoxyethoxy)benzoyl]oxy}phenyl)prop-2-enoyl]oxy}hexyl 3,5-diaminobenzoate in analogy to PAA-1 to yield 1.1 g of polyamic acid PAA-7 in the form of a white powder. [η]=0.20 dL/g $^1$H NMR (300 MHz) in DMSO-d6: 12.40 (s, 2H), 10.20 (m, 2H), 8.33 (d, 1H), 8.05 (d, 2H), 7.97 (m, 2H), 7.79 (m, 2H), 7.67 (d, 1H), 7.30 (d, 2H), 7.11 (d, 2H), 6.63 (d, 1H), 4.20 (m, 6H), 3.88 (m, 1H), 3.65-3.55 (m, 6H), 1.70 (m, 4H), 1.43 (m, 4H).

Preparation of PAA-8

0.329 g (1.68 mmol) of 1,2,3,4-cyclobutanetetracarboxylic acid is added to a solution of 18 mg (0.034 mmol) 4-{(1E)-3-[2-(2,4-diaminophenyl)ethoxy]-3-oxoprop-1-enyl}phenyl 4-(4,4,4-trifluorobutoxy)benzoate (prepared according to 2-(2,4-Diaminophenyl)ethyl(2E) 3-{4-[(4-(4,4,4-trifluorobutoxy)benzoyl)oxy]phenyl}acrylate as described in WO2007/071091 in example 4) and 800 mg (1.647 mmol) 4-{(1E)-3-[2-(2,4-diaminophenyl)ethoxy]-3-oxoprop-1-enyl}phenyl 4-(3-nitrilepropoxy)benzoate (as described in example 2) in 4.59 g of NMP. Stirring is then carried out at 0° C. for 2 hours. The mixture is subsequently allowed to react for 4 hours at room temperature. The polymer mixture is diluted with 40 g of NMP, precipitated into 300 mL of water to yield, after drying at room temperature under vacuum, 1.04 g of PAA-8 in the form of a white powder. [η]=0.44 dL/g $^1$H NMR (300 MHz) in DMSO-d6: 12.48 (s, 2H), 10.22 (s, 1H), 9.61 (s, 1H), 8.08 (d, 2H), 7.92-7.58 (m, 4H), 7.49-7.25 (m, 3H), 7.24-7.05 (m, 3H), 6.61 (m, 1H), 4.31 (m, 2H), 4.15 (m, 2H), 4.04-3.50 (m, 4H), 2.95 (3, 2H), 2.67 (m, 2H), 2.04 (m, 1.96).

Imidisation Step: Formation of Polyimide (PI)

Preparation of PI-3 from PAA-3

1.45 g of polyamic acid PAA-3 obtained in example 5 above, is dissolved in 3.5 ml of NMP. Thereto are added 0.165 mL of pyridine and 0.195 mL of acetic acid anhydride. The dehydration and ring closure is carried out at 80° C. for 2 h. The polymer mixture is diluted with 10 ml of NMP, precipitated into 100 ml diethyl ether and collected by filtration. The polymer is reprecipitated from THF (10 ml) into 200 ml water to yield, after drying at room temperature under vacuum, 1.10 g polyimide, PI-3, as an off-white powder. [η]=0.40 dL/g; Imidization degree 42%

$^1$H NMR (400 MHz) in DMSO-d$_6$: 12.52 (m, 1.1H), 10.51-9.09 (m, 1.1H), 8.07 (s, 2H), 7.93-7.20 (m, 8H), 7.11 (m, 2H), 6.59 (m, 1H), 4.26 (m, 2H), 4.14 (s, 2H), 3.60-2.40 (m, 12H), 2.05 (s, 2H).

Application Examples A

Example 6

A liquid crystal cell is prepared, wherein the liquid crystal is aligned by photo reactive polyamic acid PAA-3 and the electric field is applied between two plan electrodes on each side of the cell gap.

A 4.0% solution of polyamic acid PAA-3 is prepared by mixing the solid polyamic acid PAA-3 in NMP and stirred thoroughly till the solid polyamic acid PAA-3 is dissolved and a second solvent butyl cellulose (BC) is added and the whole composition is stirred thoroughly to obtain final solution. The solvent ratio between NMP and butyl cellulose is 1:1. The above polymer solution was spin-coated onto the two ITO coated glass substrates at a spin speed of 1700 rpm for 30 seconds. After spin coating the substrates are subjected to baking procedure consisting of pre-baking for 1.5 minutes at 130° C. and post-baking for 40 minutes at a temperature of 200° C. The resulting layer thickness is around 70 nm. The substrates with the coated polymer layer on top are exposed to linearly polarized UV light (LPUV) at an incidence angle of 40° relative to the normal of the substrate surface. The plane of polarization was within the plane spanned by the substrate normal and the propagation direction of the light. The applied exposure dose is 100 mJ/cm$^2$. After LPUV exposure a cell is assembled with the 2 substrates, the exposed polymer layers facing to the inside of the cell. The substrates are adjusted relative to each other such that the induced alignment directions are parallel to each other (corresponds to the anti-parallel, i.e 180°, rubbed configuration in case of alignment by rubbing procedure). The cell is capillary filled with liquid crystal MLC3005 (Merck KGA), which had a positive dielectric anisotropy. After that, the cell is optionally annealed at about 92° for 10 minutes and slowly cooled down to room temperature. The liquid crystal in the cell showed well defined and homogeneous planar orientation before and after thermal annealing of the cell. A tilt angle of about 0.03° is measured using the rotating analyzer method from Shintech.

Example 7

A cell is prepared as described in Example 6, with the single difference that an exposure dose of 20 mJ/cm$^2$ is used. The liquid crystal in the cell showed well defined and homogeneous planar orientation before and after thermal annealing of the cell. A tilt angle of about 0.03° is measured using the rotating analyzer method.

Example 8

A cell is prepared as described in Example 7, with the single difference that one substrate is a patterned ITO with in-plane patterned ITO electrodes having 10 microns wide stripes separated by 10 microns wide gap. The liquid crystal in the cell showed well defined and homogeneous planar orientation before and after thermal annealing of the cell. A tilt angle of about 0.04° is measured using the rotating analyzer method from Shintech.

Example 9

A cell is prepared as described in Example 8, with the single difference that an exposure dose of 300 mJ/cm$^2$ is used. The liquid crystal in the cell showed well defined and homogeneous planar orientation before and after thermal annealing of the cell. A tilt angle of about 0.1° is measured using the rotating analyzer method.

Example 10

A cell is prepared as described in Example 6, with the difference that an incidence angle of 0° and an exposure dose of 20 mJ/cm$^2$ are used. The substrates were adjusted relative to each other such that the induced alignment directions were parallel to each other (corresponds to 0° configuration). The liquid crystal in the cell showed well defined and homogeneous planar orientation before and after thermal annealing of the cell. A tilt angle of about 0.1° is measured using the rotating analyzer method.

Example 11

A cell is prepared as described in Example 8, with the difference that an incidence angle of 10° and an exposure dose of 100 mJ/cm$^2$ are used. The liquid crystal in the cell showed well defined and homogeneous planar orientation before and after thermal annealing of the cell. A tilt angle of about 0.17° is measured using the rotating analyzer method.

Example 12

A cell is prepared as described in Example 11, with the single difference that an incidence angle of 5° is used. The liquid crystal in the cell showed well defined and homogeneous planar orientation before and after thermal annealing of the cell. A tilt angle of about 0.23° is measured using the rotating analyzer method.

Example 13

A cell is prepared as described in Example 4, with the single difference that an incidence angle of 0° is used. The substrates were adjusted relative to each other such that the induced alignment directions were parallel to each other (corresponds to 0° configuration). The liquid crystal in the cell showed well defined and homogeneous planar orientation before and after thermal annealing of the cell. A tilt angle of about 0.04° is measured using the rotating analyzer method.

Example 14

A cell is prepared as in Example 6, except that the solution to be coated comprised polyamic acid PAA-4 as described in example 6. The liquid crystal in the cell showed well defined and homogeneous planar orientation before and after thermal annealing of the cell. A tilt angle of about 0° is measured using the rotating analyzer method.

Example 15

A cell is prepared as in Example 14, with the single difference that an exposure dose of 20 mJ/cm$^2$ is used. The liquid crystal in the cell showed well defined and homogeneous planar orientation before and after thermal annealing of the cell. A tilt angle of about 0° is measured using the rotating analyzer method.

Example 16

A cell is prepared as in Example 15, except that the solution to be coated comprised polyamic acid PAA-4 prepared as described in example 6. The liquid crystal in the cell showed well defined and homogeneous planar orientation before and after thermal annealing of the cell. A tilt angle of about 0.21° is measured using the rotating analyzer method.

Example 17

A cell is prepared as in Example 8, with the single difference that an exposure dose of 100 mJ/cm$^2$ is used. The liquid crystal in the cell showed well defined and homogeneous planar orientation before and after thermal annealing of the cell. A tilt angle of about 0.18° is measured using the rotating analyzer method.

Example 18

A cell is prepared as in Example 6, except that the solution to be coated comprised polyamic acid PAA-2 prepared as described in example 6. The liquid crystal in the cell showed well defined and homogeneous planar orientation before and after thermal annealing of the cell. A tilt angle of about 0° is measured using the rotating analyzer method.

Example 19

A cell is prepared as in Example 18, with the single difference that an exposure dose of 20 mJ/cm$^2$ is used. The liquid crystal in the cell showed well defined and homogeneous planar orientation before and after thermal annealing of the cell. A tilt angle of about 0.08° is measured using the rotating analyzer method.

Example 20

A cell is prepared as in Example 8, except that the solution to be coated comprised polyamic acid PAA-2 prepared as described in example 6 and that an incidence angle of 0° is used. The liquid crystal in the cell showed well defined and homogeneous planar orientation before and after thermal annealing of the cell. A tilt angle of about 0° is measured using the rotating analyzer method.

Example 21

A cell is prepared as in Example 6, except that an exposure dose of 20 mJ and incidence angle of 0° are used, and the solution to be coated comprised of polyamic acid PAA-3 and polyamic acid PAA-6 mixed in ratio of 20:80 per weight % to form a blend composition. A 4.0% solution is prepared as per the procedure explained in Example 5 except that the two polymers were mixed in the solvent at the same time and the spin speed used is 2100 rpm for 30 seconds. The substrates were adjusted relative to each other such that the induced alignment directions were parallel to each other (corresponds to 0° configuration). The liquid crystal in the cell showed well defined and homogeneous planar orientation before and after thermal annealing of the cell. A tilt angle of about 0.02° is measured using the rotating analyzer method.

Example 22

A cell is prepared as in Example 21, except that the solution to be coated comprised of polyamic acid PAA-3 and polyamic acid PAA-5 mixed in ratio of 20:80 per weight % to form a blend composition. The liquid crystal in the cell showed well defined and homogeneous planar orientation before and after thermal annealing of the cell. A tilt angle of about 0.09° is measured using the rotating analyzer method.

Example 23

A cell is prepared as in Example 6, except that an exposure dose of 250 mJ is used and the solution to be coated comprised of polyamic acid PAA-1. A 4.0% solution is prepared as per the procedure explained in Example 6 and the spin speed used is 1300 rpm. The liquid crystal in the cell shows planar orientation with alignment defects before thermal annealing of the cell. After thermal annealing of the cells, the liquid crystal shows homogeneous planar orientation without any defects. A tilt angle of about 0.02° is measured using the rotating analyzer method.

Example 24

A cell is prepared as in Example 23, except that an exposure dose of 40 mJ is used. The liquid crystal in the cell shows planar orientation with alignment defects before thermal annealing of the cell. After thermal annealing of the cells, the liquid crystal shows homogeneous planar orientation without any defects. A tilt angle of about 0.19° is measured using the rotating analyzer method.

Example 25

A cell is prepared as in Example 8, except that the solution to be coated comprised polyamic acid PAA-1 prepared as described in example 6 and an exposure dose of 300 mJ is used. The liquid crystal in the cell shows planar orientation with alignment defects before thermal annealing of the cell. After thermal annealing of the cells, the liquid crystal shows homogeneous planar orientation without any defects. A tilt angle of about 0.06° is measured using the rotating analyzer method.

Example 26

A cell is prepared as in Example 25, except that an exposure dose of 20 mJ is used. The liquid crystal in the cell shows planar orientation with alignment defects before thermal annealing of the cell. After thermal annealing of the cells, the liquid crystal shows homogeneous planar orientation without any defects. A tilt angle of about 0.01° is measured using the rotating analyzer method.

Example 27

Cells are prepared as described in Examples 6, 10, 14, 15, 18, 19, 21, 22, 23, 24. Voltage holding ratio (VHR) of the cells was measured at room temperature using LCM-1 instrument from Toyo, Japan. The VHR was measured using a short and a long frame period (T). In the short one, the voltage decay V (at T=20 ms) of a voltage surge of 64 µs with $V_0$ (V at t=0)=5V is then measured over a period of T=20 ms. In the long one, the voltage decay V (at T=1667 ms) of a voltage surge of 64 µs with $V_0$ (V at t=0)=1V is then measured over a period of 1=1667 ms. The voltage holding ratio is then determined, at room temperature, given by integration of the measurement curve between $V_0$ and V weighted by the area in the case of 100% VHR. The results show a VHR≥99.4 for all tested cells.

Example 28

Cells are prepared as described in Examples 8, 9, 10, 11, 12, 16, 17, 20, 25 and 26. The contrast of these cells was measured in the NB mode (crossed polarizers) using a white light source. The polarisers are rotated until a minimum transmission for the short-circuited cell is measured, then the cell switched on and the maximum transmission is determined.

Example 29

Switching or the rise time ($t_{on}$) was measured, for typical materials, in the NW mode (parallel polarisers), by switching from 0 to $2.5 \times V_{10}$, where $V_{10}$ is the voltage at 10% of the maximum transmission.

The obtained results show $t_{on}$ of about 3.6 ms, 4.7 ms and 6.9 ms, respectively for cells made with PAA-4, PAA-3 and PAA-1.

Example 30

3 TN (Twisted Nematic) cells are prepared as described in Example 10 using PAA-3, PAA-2 photopolymers, respectively, except that angle between the exposure directions of the two substrates was 75° (Twisted Nematic cells) instead of 0° or 180° (planar cells). Azimuthal anchoring energy (AAE) was measured using the torque balance method. The LC used was again MLC3005. The twist of the resulting TN-cells was measured and the azimuthal anchoring energy (AAE) was calculated by using the formula:

$$AAE = \frac{2K_2 \varphi_{twist} \Delta n}{R \sin(2\Delta\varphi)}$$

where $K_2=(6.2\pm0.6)$ pN is the twist elastic constant, $\Delta n=0.0995$ the birefringence of MLC3005, R the measured retardation (R=d*$\Delta n$) and $2\Delta\phi=\phi_{exp}-\phi_{twist}$. ($\phi_{twist}$ is the angle between the exposure directions).

The obtained results show that AAE the azimuthal anchoring energies of photo-alignment materials with polar (Nitril) is much higher. Indeed, AAE using photo-alignment material PAA-3 and PAA-4, of about $2.4 \times 10^{-4}$ J/m².

Example 31

Cells are prepared as described in Examples 9 and 25. Image sticking (AC-memory) of these cells was measured (at room temperature) by applying an AC stress of 7.3 V (60 Hz) to cells for 24 hours and measuring change in transmission, $\Delta T$, at the voltage corresponding to 1% transmission of V-T curve before AC stress. The obtained results show that image sticking of photo-alignment materials is low; PAA-3, $\Delta T$ of about 0.039%.

Example 32

A cell is prepared as in Example 6, except that an exposure dose of 20 mJ and incidence angle of 40° are used, and the solution to be coated comprised of polyamic acid PAA-2 and polyamic acid from the diamine 4-{(1E)-3-[2-(2,4-diaminophenyl)ethoxy]-3-oxoprop-1-enyl}phenyl 4-(4,4,4-trifluorobutoxy)benzoate (prepared according to WO2007/071091, =0.40 dL/g) in ratio of 98:2 per weight % to form a blend composition. A 4.0% solution is prepared as per the procedure explained in Example 6 except that the two polymers were mixed in the solvent at the same time and the spin speed used is 1400 rpm for 30 seconds. The liquid crystal in the cell showed well defined and homogeneous planar orientation before and after thermal annealing of the cell. A tilt angle of about 0.04° is measured using the rotating analyzer method.

Example 33

A cell is prepared as in Example 6, except that an exposure dose of 20 mJ is used and the solution to be coated comprised of polyamic acid PAA-7. A 4.0% solution is prepared as per the procedure explained in Example 6 and the spin speed used is 1500 rpm. The liquid crystal in the cell showed well defined and homogeneous planar orientation before and after thermal annealing of the cell. A tilt angle of about 0.02° is measured using the rotating analyzer method.

Example 34

A cell is prepared as in Example 6, except that an exposure dose of 20 mJ is used and the solution to be coated comprised of polyamic acid PAA-8. A 4.0% solution is prepared as per the procedure explained in Example 6 and the spin speed used is 1900 rpm. The liquid crystal in the cell showed well defined and homogeneous planar orientation before and after thermal annealing of the cell. A tilt angle of about 0.05° is measured using the rotating analyzer method.

Example 35

A liquid crystal cell is prepared wherein the liquid crystals are aligned by polyamic acid PAA-3. A 4.5 wt % solution of polyamic acid PAA-3 is prepared by mixing the solid polyamic acid PAA-3 in the solvent n-methyl-2-pyrrolidone (NMP) and stirred thoroughly till the solid polyamic acid PAA-3 is dissolved and a second solvent butyl cellosolve (BC) is added and the whole composition is stirred thoroughly to obtain the final solution. The solvent ratio between n-methyl-2-pyrrolidone and butyl cellosolve is 1:1.

The above polymer solution is spin-coated onto a first and a second glass substrate at a spin speed of 1100 rpm for 30 seconds. On top of the first substrate is an ITO electrode with an interdigital pattern, with an electrode width and spacing of 10 μm. The second substrate is without any ITO coating.

After spin coating, the substrates are subjected to pre-baking for 90 seconds at 80° C. and post-baking for 40 minutes at a temperature of 200° C. The resulting layer thickness is around 100 nm. The substrates with the coated polymer layer on top are exposed to linearly polarized UV-B light (LPUV) with the incidence angle normal to the substrate surface. The applied exposure dose is 22 mJ/cm².

After LPUV exposure a cell is assembled with the 2 substrates, the exposed polymer layers facing to the inside of the cell. The substrates are adjusted relative to each other such that the induced alignment directions are parallel to each other. The cell is then capillary filled with liquid crystal, Licristal®MLC-3019 (Merck Ltd.), which exhibits a positive dielectric anisotropy. The cell is then subjected to a thermal annealing at 130° C. for 30 minutes to complete the cell process.

The liquid crystal in the cell shows well defined planar orientation. A tilt angle of 0.012° is measured using the rotating analyzer method.

The cell is then arranged between two crossed polarizers such as to obtain a dark state. Upon applying a voltage of 5V to the interdigital electrodes of the cell, the liquid crystal cell switches uniformly to a bright state.

Measurement of the Voltage Holding Ratio:

The voltage decay V (at T=16.67 ms) of a voltage surge of 64 μs with $V_0$(V at t=0)=5V is then measured over a period of T=16.67 ms in order to determine the voltage holding ratio (VHR) of the cell. The voltage holding ratio, given by VHR=$V_{rms}$(t=T)/$V_o$, is then determined as 99.6%, at room temperature.

Evaluation of Image Sticking:

The voltages V1 and V100 at which the cell exhibits light transmission of 1% and 100%, respectively are determined. The cell is then subjected to an electrical stress test with an AC voltage of V100=5.5V applied to the cell for 20 hours. In order to evaluate image sticking the transmission at V1 is measured again and gives a value of 1.29%, which means that the transmission is 29% higher than the initial value.

Example 36

A liquid crystal mixture LC1 is prepared by adding 0.026 g of Monomer 1, which is 2-Propenoic acid, 2-methyl-, 1,1'-[1,1'-biphenyl]-4,4'-diyl ester, (commercially available from Shanghai Chemhere)

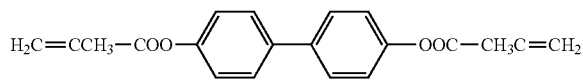

to 10.0 g of MLC-3019. The mixture is heated to 50° C. and stirred for 2 min.

A liquid crystal cell is prepared in similar manner as in example 35 except that liquid crystal mixture LC1 is used instead of Licristal®MLC 3019. In addition to the process of example 1, the cell is exposed to non-polarized UV-A light at a dose of 1320 mJ/cm² after the thermal annealing step for liquid crystal alignment.

The liquid crystal in the cell shows well defined planar orientation. A tilt angle of 0.011° is measured using the rotating analyzer method.

As in example 1, the cell is arranged between two crossed polarizers such as to obtain a dark state. Upon applying a voltage of 5V to the electrodes of the cell, the cell is uniformly switched to a bright state.

The voltage holding ratio, measured as in example 1, gives a value of VHR=99.6%.

Image sticking properties are evaluated according to the same procedure as in example 1. After applying the electrical stress test, the transmission at V1 is 1.036%, which means that the transmission is 3.6% higher than the initial value.

Example 37

A cell is prepared in a similar manner as in Example 35 except that the liquid crystal mixture used is Licristal®MLC-7067. The liquid crystal in the cell shows well defined planar orientation. A tilt angle of 0.013° is measured using the rotating analyzer method.

As in example 1, the cell when arranged between crossed polarizers switches uniformly from a dark state to a bright state upon applying a voltage of 5V.

The voltage holding ratio is determined as VHR=99.5% at room temperature.

Image sticking properties are evaluated according to the same procedure as in example 1. After applying the electrical stress test, transmission at V1 is 1.29%, which means that the transmission is 29% higher than the initial value.

Example 38

Preparation of Liquid Crystal Mixture LC2

0.3916 g of compound XIII as listed in page 11 of preparation example 35 of patent US2012/0114907A1 is mixed in a solvent of anisole, together with 0.008 g of 2-Benzyl-2-(dimethylamino)-4'-morpholino butyrophenone (commercially available from BASF) and 0.0004 g of 3,5-Di-tert-4butyl hydroxy toluene (commercially available from Fluka) and stirred to obtain a 2 wt % liquid crystal mixture LC2.

A cell is prepared in a similar manner as in example 37, except that after the linearly polarized UV-B exposure of the coated polymer substrates and before cell assembly, liquid crystal mixture LC2 is spin-coated on top of the UV-B exposed polymer substrates at 4000 rpm for 30 sec. The substrates are then heated in an oven for 2 minutes at 55° C., and after cooling down to room temperature the coated substrates are exposed to non-polarized UV-A light at a dose of 1000 mJ/cm² in nitrogen atmosphere. A 18 nm thin film comprising cross-linked liquid crystals is obtained. The further cell process is completed as in example 37.

The liquid crystal in the cell shows well defined planar orientation. A tilt angle of 0.015° is measured using the rotating analyzer method.

As in example 35, the cell when arranged between crossed polarizers switches uniformly from a dark state to a bright state upon applying a voltage of 5V.

The voltage holding ratio is determined as VHR=99.4% at room temperature.

Image sticking properties are evaluated according to the same procedure as in example 35. After applying the electrical stress test, transmission at V1 is 1.098%, which means that the transmission is 9.8% higher than the initial value.

Example 35a

Preparation of 4-(4-cyanobutoxy)benzoic acid compound 35A

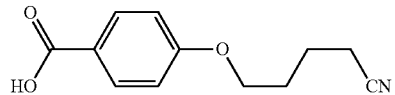 [SMILES: N#CCCCCOc1ccc(C(=O)O)cc1]

21.0 g (130 mmol) of 5-bromopentanenitrile, 15.2 g (100 mmol) of methyl 4-hydroxybenzoate and 28 g (200 mmol) of potassium carbonate are dissolved in 100 mL of DMF. The mixture is heated to 80° C. overnight. 100 mL (100 mmol) of a 1N NaOH solution is added to the above mixture. The suspension is heated at reflux for 30 min until the reaction is completed. The reaction mixture is allowed to cool down to room temperature and thrown onto cold water. The solution is carefully acidified with a 25% HCl solution and is stirred for 15 min. The product is filtrated off, washed with water and dried overnight under vacuum to give 19.3 g of 4-(4-cyanobutoxy)benzoic acid as a white solid.

The benzoic acid compounds 35B, 35C, 35D, 35E, 35F, 35H are prepared according to the process described in example 35a for compound 35A with the proviso that 5-bromopentanenitrile is replaced by 7-bromoheptanitrile, respectively 4-bromobut-1-yne, respectively 1,4-dichlorobutane, respectively 4-benzoylbenzoic acid, respectively 4-(diethylamino)benzoic acid, respectively 1-bromobut-2-yne.

The benzoic acid compounds 35I, 35J, 35K, 35L are prepared according to the process described in example 35a for compound 35A with the proviso that 5-bromopentanenitrile is replaced by 4-bromobutanenitrile and methyl 4-hydroxybenzoate is replaced by methyl 3-fluoro-4-hydroxybenzoate, respectively methyl 2,3,5,6-tetrafluoro-4-hydroxybenzoate, respectively 4'-hydroxybiphenyl-4-carboxylic acid methyl ester, respectively methyl 4-hydroxy-3-(trifluoromethyl)benzoate. respectively methyl 4-cyanocyclohexanecarboxylate.

Example 36a

Preparation of (2E)-3-(4-{[4-(4-cyanobutoxy)benzoyl]oxy}phenyl)prop-2-enoic acid compound 36A

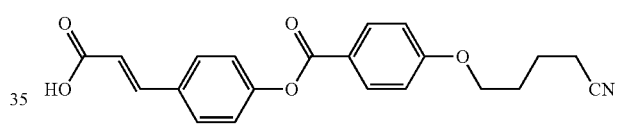

17.9 g (82 mmol) of compound 35A is suspended in 56 mL of toluene and few drops of DMF are added. The suspension is heated up to 75° C. and 10.7 g (90 mmol) of thionylchloride are added. After 2 hours, the excess of thionylchloride is removed under pressure. The solution is cooled down to room temperature. 10.2 g (83 mmol) of 4-hydroxybenzaldehyde, 0.5 g (4 mmol) of 4-diaminopyridine and 28 g (355 mmol) of pyridine are added. After 3 hours, 14.5 g (140 mmol) of malonic acid and 3 g (42 mmol) of pyrrolidine are added. The reaction mixture is allowed to react at 80° C. for 30 min. Then, 16.8 mL of MeOH are incorporated and the suspension is cooled down and kept at 0° C. for 1 hour. The product is filtered off and suspended for 2 hours in a solution of 57 mL of MeOH, 11 mL of H₂O and 7.5 g of a 25% HCl solution. The solid is filtered off and washed with MeOH and heptane. The product is crystallized in acetonitrile to give 23 g of (2E)-3-(4-{[4-(4-cyanobutoxy)benzoyl]oxy}phenyl)prop-2-enoic acid as a white powder.

The compounds 36B, 36C, 36D, 36E, 36F, 36H, 36I, 36J, 36K, 36L, 36M, 36N, 36O are prepared according to the process described in example 36a for compound 36A with the proviso that compound 35A is replaced by compound 35B, respectively 35C, respectively 35D, respectively 35E, respectively 35F, respectively 35H, respectively 35I, respectively 35J, respectively 35K, respectively 35L, respectively 4-cyanocyclohexanecarboxylic acid, respectively 4-cyanobenzoic acid, respectively compound 4-(2-methoxyethoxy)benzoic acid prepared in Example 4.2. The compounds 36P, 36Q are prepared according to the process described in example 2.1 for compound 2E)-3-(4-{[4-(3- cyanopropoxy)benzoyl]oxy}phenyl)prop-2-enoic acid with the proviso that 4-hydroxybenzaldehyde is replaced by vaniline, respectively 3-fluoro-4-hydroxybenzaldehyde. The compound 36R is prepared according to the process described in example 36 for compound 36B with the proviso that 4-hydroxybenzaldehyde is replaced by 2,6-Difluoro-4-hydroxybenzaldehyde.

Example 37a

Preparation of methyl(2E)-3-[4-(3-hydroxypropoxy)phenyl]prop-2-enoate compound 37

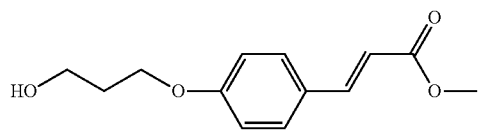 [SMILES: COC(=O)/C=C/c1ccc(OCCCO)cc1]

15 g (84.2 mmol) of 4-hydroxycinnamic acid methyl ester, 14 g (101 mmol) of 3-bromo-1-propanol, 23.4 g of $K_2CO_3$ are dissolved in 90 mL of NMP. The solution is heated up to 80° C. and stirred for 20 hours. Then, the reaction mixture is cooled down to room temperature and carefully acidified with 1N HCl solution. The solution is extracted with ethylacetate. The organic phase is dried over sodium sulfate, filtrated and concentrated under reduced pressure. Chromatography of the residue on silica gel using hexane:ethyl acetate 7:3 as eluent yielded 5.8 g of methyl (2E)-3-[4-(3-hydroxypropoxy)phenyl]prop-2-enoate as a white solid.

Example 37b

Preparation of methyl(E)-2-cyano-3-[4-(6-hydroxyhexoxy)phenyl]prop-2-enoate 37B

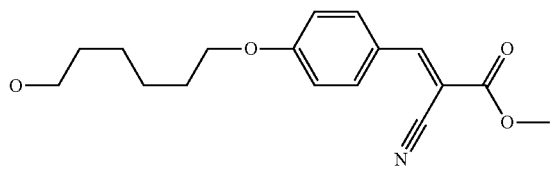 [SMILES: COC(=O)/C(C#N)=C/c1ccc(OCCCCCCO)cc1]

The compound 37B is prepared according to the process described in example 37a with the proviso that 4-hydroxycinnamic acid methyl ester is replaced by methyl(E)-2-cyano-3-(4-hydroxyphenyl)prop-2-enoate and 3-bromo-1-propanol is replaced by 6-chloro-1-hexanol.

Example 37c

Preparation of 6-[4-[(E)-2-cyano-3-methoxy-3-oxo-prop-1-enyl]phenoxy]hexyl 3,5-dinitrobenzoate 37C

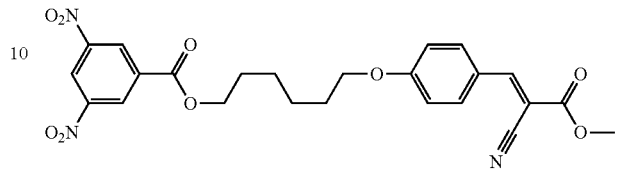

The compound 37C is prepared according to the process described in Example 1-3 with the proviso that (2E)-3-{4-[(6-hydroxyhexyl)oxy]-3-methoxyphenyl}prop-2-enoate is replaced by compound 37B.

Preparation Examples

Example 38a

Preparation of 4-(4-hydroxyphenoxy)butanenitrile compound 38

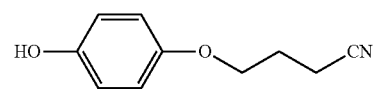

To a solution of 1.7 g of NaOH in 80 ml of $H_2O$:dioxane 1:1, 2.2 g (20 mmol) of hydroquinone are added. The solution is stirred for 15 min. Then, 3.5 g (24 mmol) of 3-bromopropanitrile is dropwise added. After complete addition, the mixture is heated up to reflux and stirred for 24 hours. 45 mL of a 1N HCl solution is added to the above mixture. The solution is extracted with ethylacetate and concentrated under reduced pressure to give 2.8 g of 4-(4-hydroxyphenoxy)butanenitrile which is used without further purification.

Example 39

Preparation of (2E)-3-(4-{3-[4-(3-cyanopropoxy)phenoxy]propoxy}phenyl)prop-2-enoic acid compound 39

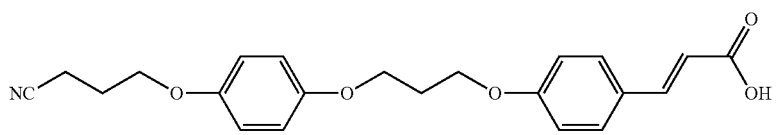 [SMILES: N#CCCCOc1ccc(OCCCOc2ccc(/C=C/C(=O)O)cc2)cc1]

To a solution of 5.6 g (23.7 mmol) of compound 37, 7.5 g (42.2 mmol) of compound 38, 7.8 g (29.6 mmol) of triphenylphosphine in 100 mL of THF are added 6 g (29.6 mmol) of diisopropylazodicarboxylate under inert atmosphere. The solution is heated up to reflux and allowed to stir overnight. After 20 hours, the reaction mixture is partitioned between ethylacetate and water. The organic phase is washed repeatedly with water, dried over sodium sulphate, filtered and concentrated by rotary evaporation to give 6.1 g of a solid which is added to a solution of 1.5 g NaOH in 100 mL of H$_2$O:MeOH 1:1. The reaction mixture is heated up to 70° C. After 5 hours, the mixture is cooled down to 0° C. and neutralised with a 1N HCl solution. The product is filtered off, washed with H$_2$O and dried under vacuum to yield 6.2 g of (2E)-3-(4-{3-[4-(3-cyanopropoxy)phenoxy]propoxy}phenyl)prop-2-enoic acid Example 40

Preparation of 4-[4-(cyanomethyl)phenoxy]butanenitrile compound 40

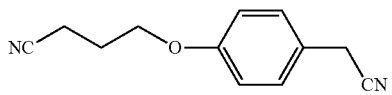

12.2 g (82.6 mmol) of 4-bromobutyronitrile, 10 g (95.1 mmol) of (4-hydroxyphenyl)acetonitrile and 31.1 g (225 mmol) of potassium carbonate are dissolved in 100 mL of DMF. The mixture is heated to 80° C. overnight. After 20 hours, the reaction mixture is partitioned between EtOAc and water. The organic phase is washed repeatedly with brine, dried over sodium sulphate, filtered and concentrated by rotary evaporation. Purification by column chromatography on silica gel using ethylacetate:hexane 1:1 as eluent yields to 4.4 g of 4-[4-(cyanomethyl)phenoxy]butanenitrile as a thick yellow oil.

Example 41

Preparation of 4-{(Z)-2-cyano-2-[4-(3-cyanopropoxy)phenyl]ethenyl}benzoic acid compound 41

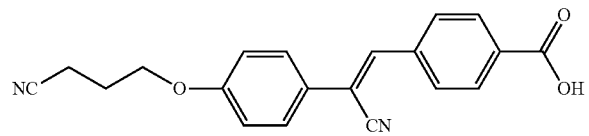 [SMILES: N#CCCCOc1ccc(/C(C#N)=C/c2ccc(C(=O)O)cc2)cc1]

1.55 g (7.7 mmol) of compound 40, 1.27 g (7.7 mmol) of methyl 4-formylbenzoate are dissolved in 50 mL of propan-2-ol. The solution is heated up to 60° C. and 0.72 mL of a 1M solution of tetrabuthylamoniumhydroxyde in methanol is added dropwise. After 2 h at 60° C., the reaction mixture is cooled down to 0° C. The precipitate is filtered off, washed with cold methanol. The solid is dissolved in THF and 10 ml of 1N NaOH is added. The mixture is heated up to 60° C. and allowed to stir for 20 hours at 60° C. Then, it is partitioned between EtOAc and water. The combined organic phase are washed repeatedly with water, dried over sodium sulphate, filtered and concentrated by rotary evaporation. Recristalization in ethylacetate yields to 0.620 g of 4-{(Z)-2-cyano-2-[4-(3-cyanopropoxy)phenyl]ethenyl}benzoic acid as a yellowish solid.

Example 42

Preparation of methyl(2E)-3-[4-(3-bromopropoxy)phenyl]prop-2-enoate compound 42

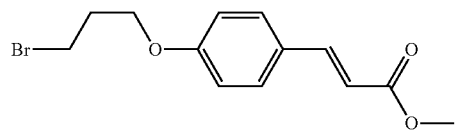 [SMILES: COC(=O)/C=C/c1ccc(OCCCBr)cc1]

To a solution 5 g (28.1 mmol) of 4-Hydroxycinnamic acid methyl ester, 4.9 g (35.1 mmol) of 4 bromopropanol, 9.2 g (35.1 mmol) of triphenylphosphine in 100 mL of THF are added 7.1 g (35.1 mmol) of diisopropylazodicarboxylate under inert atmosphere. The solution is heated up to reflux and allowed to stir overnight. After 20 hours, the reaction mixture is partitioned between EtOAc and water. The organic phase is washed repeatedly with water, dried over sodium sulphate, filtered and concentrated by rotary evaporation to give 7.5 g of (methyl(2E)-3-[4-(3-bromopropoxy)phenyl]prop-2-enoate.

Example 43

Preparation of (2E)-3-{4-[3-(4-cyanophenoxy)propoxy]phenyl}prop-2-enoic acid compound 43

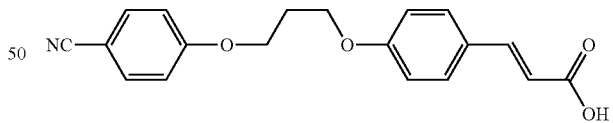

2 g (6.7 mmol) of compound 42, 0.790 g (6.7 mmol) of 4-Hydroxybenzonitrile, 1.8 g (13.4 mmol) of potassium carbonate are dissolved in 25 ml of NMP. The solution is heated up to 80° C. and allowed to stir overnight at this temperature. Then, a solution of 0.670 g of NaOH in 10 mL of H$_2$O/MeOH (1/1) is added to the above mixture. The reaction is heated up to 60° C. for 5 hours. Then, the mixture is partitioned between ethyl acetate and water. The combined organic phase are washed repeatedly with water, dried over sodium sulphate, filtered and concentrated by rotary evaporation. Purification by a slurry in MeOH yields to 1.7 g of (2E)-3-(4-[3-(4-cyanophenoxy)propoxy]phenyl)prop-2-enoic acid as a yellowish solid.

Example 44

Preparation of 3-cyanopropyl(2E)-3-(4-hydroxy-3-methoxyphenyl)prop-2-enoate compound 44

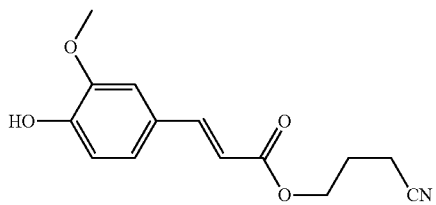 [SMILES: COc1cc(/C=C/C(=O)OCCCC#N)ccc1O]

To a solution of 5 g (25.7 mmol) of 3-(4-hydroxy-3-methoxy-phenyl)prop-2-enoic acid in 20 mL of DMF, 3.92 g (25.74 mmol) of 1,8-diazabicycloundec-7-ene (DBU) in 5 mL of DMF are added dropwise. Then, 4.2 g (28.32 mmol) of 4-bromobutanenitrile are slowly incorporated in the above mixture. The solution is stirred at room temperature for 18 hours. The mixture is poured onto cooled HCl solution. Then, the mixture is extracted with ethylacetate. The combined organic phase are washed repeatedly with water, dried over sodium sulphate, filtered and concentrated under reduced pressure. Purification by chromatography column on silica gel using toluene:ethyl acetate 4:1 as eluent yields to 5.68 g of 3-cyanopropyl(2E)-3-(4-hydroxy-3-methoxyphenyl)prop-2-enoate as a white solid.

Example 45

Preparation of 3-cyanopropyl(2E)-3-{4-[(6-hydroxyhexyl)oxy]-3-methoxyphenyl}prop-2-enoate compound 45

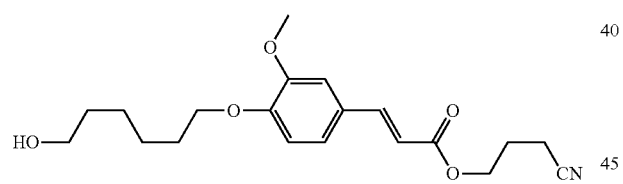

The compound 45 is prepared according to the process described in example 1-2 for compound methyl(2E)-3-{4-[(6-hydroxyhexyl)oxy]-3-methoxyphenyl}prop-2-enoate with the proviso that (2E)-3-(4-hydroxy-3-methoxyphenyl)prop-2-enoate is replaced by compound 44.

Example 46

Preparation of 5-(2,4-dinitrophenyl)pentan-1-ol compound 46

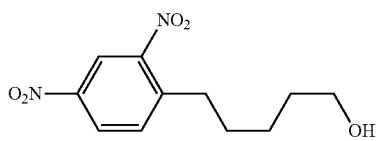 [SMILES: O=[N+]([O-])c1ccc(CCCCCO)c([N+](=O)[O-])c1]

50 g (304 mmol) of 5-phenylpentan-1-ol, 127 mL of (triethyl amine) NEt₃ are dissolved in 50 mL of THF at 0° C. 46.5 g (456 mmol) of acetic anhydride is added to the mixture. The solution is stirred for 2 h at 0° C. and allowed to stir at room temperature overnight. After 22 hours at room temperature, the reaction mixture is partitioned between ethyl acetate and water. The organic phase is washed repeatedly with water, dried over sodium sulfate, filtrated and concentrated under reduced pressure. The crude product is added carefully to a mixture of 250 g sulphuric acid and 160 g nitric acid cooled at −5° C. The solution is stirred for 2 h at −5° C. The mixture is quenched with 500 g of ice and the product is extracted with toluene. The organic phase is washed repeatedly with water, dried over sodium sulfate, filtrated and concentrated under reduced pressure. The yellow oil is refluxed in 300 ml of methanol with 60 ml of HCl. After 22 hours under reflux, the reaction mixture is partitioned between ethyl acetate and water. The organic phase is washed repeatedly with water, dried over sodium sulfate, filtrated and concentrated under reduced pressure. Chromatography of the residue on 400 g silica gel using toluene:ethyl acetate 1:1 as eluent yields 61 g of 5-(2,4-dinitrophenyl)pentan-1-ol as yellowish oil.

Example 47

Preparation of 8-(2,4-dinitrophenyl)octan-1-ol compound 47

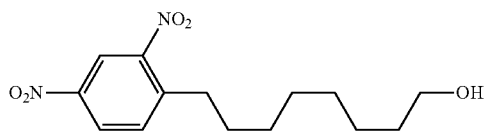 [SMILES: O=[N+]([O-])c1ccc(CCCCCCCCO)c([N+](=O)[O-])c1]

The compound 47 is prepared according to the process described in example 46 for compound 46 with the proviso that 5-phenylpentan-1-ol is replaced by 8-phenyloctan-1-ol.

Example 48

Preparation of 6-hydroxyhexyl 3,5-dinitrobenzoate compound 48

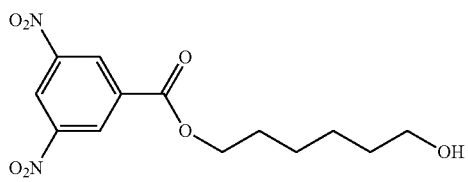

357.7 g (1.68 mol) of 3,5-dinitrobenzoic acid are suspended in 750 ml of 1-methyl-2-pyrrolidone. The suspension is stirred up to 50° C. 386.4 g (4.60 mol) of sodium hydrogen carbonate are added and the mixture was heated up to 90° C. 22.50 g (0.150 mol) of sodium iodide and 204.0 ml (1.53 mol) of 6-chlorohexanol are added to the reaction mixture which is heated to 100° C. for 1 h. After 1 h of reaction, the reaction is complete and the orange suspension is thrown on 2 l of ice and 1 l of water. The product is filtrated, washed water and dried at 50° C. under vacuum for 24 h to give 425.0 g of 6-hydroxyhexyl 3,5-dinitrobenzoate as a rose powder.

Example 49

Preparation of 2-(2,4-dinitrophenyl)propane-1,3-diol compound 49

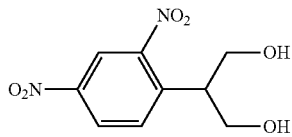

20 g (106.5 mmol) of 2,4-dinitrotoluene is solubilized in 280 ml of NMP. To the brown solution is added 7.6 g (255.6 mmol) of paraformaldehyde. To the suspension is added 597 mg (5.32 mmol) of potassium tetrabutoxyde. The resulting solution is stirred overnight at RT. The mixture was poured onto 200 ml ice, and neutralized with 2 mL of HCl 25%. The reaction mixture is then partitioned between ethyl acetate and water; the organic phase is washed repeatedly with water, dried over sodium sulfate, filtered and concentrated by rotary evaporation. The solution is precipitate at RT by adding 150 ml of heptane. The product is filtrated and dried under vacuum at RT to give 16.1 g of 2-(2,4-dinitrophenyl)propane-1,3-diol as a slightly yellow product.

Example 50

Preparation of 2,2-bis(4-nitrobenzyl)-1,3-propandiol compound 50

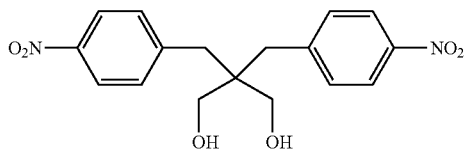 [SMILES: O=[N+]([O-])c1ccc(CC(CO)(CO)Cc2ccc([N+](=O)[O-])cc2)cc1]

4.0 g (10.7 mmol) 2,2-bis(4-nitrobenzyl)malonic acid are dissolved in 40 ml THF and added dropwise at the course of 2 hours to 64.1 ml (64.1 mmol) of a borane-tetrahydrofuran complex 1.0 M solution in THF. which is used without further purification. After 19 hours at 25° C., 50 ml of water are carefully added. The reaction mixture is then partitioned between ethyl acetate and water. The organic phase is washed repeatedly with water, dried over sodium sulfate, filtered and concentrated by rotary evaporation to give 3.8 g of 2,2-bis(4-nitrobenzyl)-1,3-propandiol as a white powder.

Example 51

Preparation of 3-[(2,4-dinitrophenyl)amino]pentan-1,5-diol compound 51

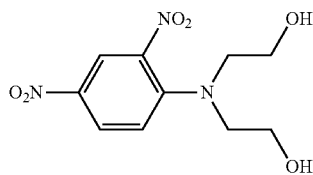 [SMILES: O=[N+]([O-])c1ccc(N(CCO)CCO)c([N+](=O)[O-])c1]

50 g (246.9 mmol) of 1-chloro-2,4-dinitrobenzene are dissolved in 200 mL of ethylacetate. 55 g (523.1 mmol) of diethanolamine are added by portion to the solution. The mixture is heated up to reflux for 2 hours. After cooling to RT, the solution is extracted with H₂O and the organic phase is washed with a brine solution. After filtration on silica gel, the product is recrystallized in ethylacetate to yield 54 g of pure 3-[(2,4-dinitrophenyl)amino]pentan-1,5-diol.

Example 52

Preparation of 4-{(1E)-3-[2-(2,4-dinitrophenyl)ethoxy]-3-oxoprop-1-enyl}phenyl 4-(4-cyanobutoxy)benzoate compound 52A

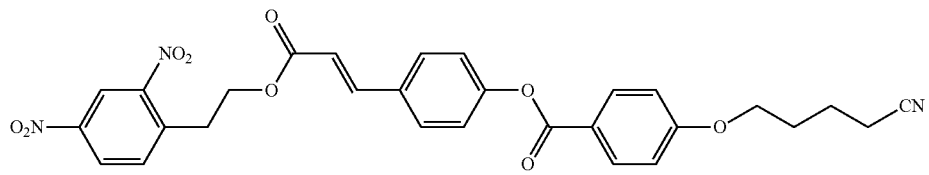 [SMILES: N#CCCCCOc1ccc(C(=O)Oc2ccc(/C=C/C(=O)OCCc3ccc([N+](=O)[O-])cc3[N+](=O)[O-])cc2)cc1]

2.50 g (11.8 mmol) of 2-(2,4-dinitrophenyl)ethanol, 4.31 g (11.8 mmol) of compound 36A, 144 mg (1.2 mmol) of 4-Dimethylaminopyridine are dissolved in 30 ml of dichloromethane. 2.48 g (13.0 mmol) of N-(3-Dimethylaminopropyl)-N'-ethylcarbodiimide hydrochloride (EDC hydrochloride) are added at 0° C. The solution is stirred for 1 h at 0° C. and allowed to stir at room temperature overnight. After 22 hours at room temperature, the reaction mixture is partitioned between dichloromethane and water. The organic phase is washed repeatedly with water, dried over sodium sulphate, filtered and concentrated by rotary evaporation. Chromatography of the residue on 200 g silica gel using toluene:ethyl acetate 95:5 as eluent following by a crystallization in ethylacetate:hexane mixture yield to 4.89 g of 4-{(1E)-3-[2-(2,4-dinitrophenyl)ethoxy]-3-oxoprop-1-enyl}phenyl 4-(4-cyanobutoxy)benzoate as colourless crystals.

The compounds 52B, 52C, 52D, 52E, 52F, 52H, 52I, 52J, 52L, 52M, 52N, 52O, 52P, 52Q, 52R, 52S, 52T, 52U are prepared according to the process described in example 52 for compound 52A with the proviso that compound 36A is replaced by compound 36B, respectively 36C, respectively 36D, respectively 36E, respectively 36F, respectively 36H, respectively 36I, respectively 36J, respectively 36L, respectively 36M, respectively 36N, respectively 36O, respectively 36P, respectively 36Q, respectively 36R, respectively 41, respectively 39, respectively 43.

The compounds 52V, 52W are prepared according to the process described in example 52 for compound 52A with the proviso that compound 36A is replaced by 3,4,5-trifluoro-cinnamic acid, respectively (2E)-2-cyano-3-(4-methoxyphenyl)prop-2-enoic acid.

The compounds 53A, 53B, 53C, 53D, 53E, 53F, 53G are prepared according to the process described in example 52 for compound 52A with the proviso that compound 36A is replaced by the compound (2E)-3-(4-{[4-(3-nitrilepropoxy)benzoyl]oxy}phenyl)prop-2-enoic acid described in example 2.2 and with the proviso that 2-(2,4-dinitrophenyl)ethanol is replaced by respectively 3,5-dinitrobenzyl alcohol, respectively compound 47, respectively compound 46, respectively compound 48, respectively compound 49, respectively compound 50, respectively compound 51. The compounds 54A, 54B are prepared according to the process described in example 52 for compound 53C with the proviso that compound (2E)-3-(4-{[4-(3-nitrilepropoxy)benzoyl]oxy}phenyl)prop-2-enoic acid is replaced by respectively compound 36N, respectively compound 36K.

The compound 55 is prepared according to the process described in example 52 for compound 52A with the proviso that compound 36A is replaced by the compound 36I and the 2-(2,4-dinitrophenyl)ethanol is replaced by 50.

The compound 55B is prepared according to the process described in example 52 for compound 52A with the proviso that compound 36A is replaced by the compound 45 and the 2-(2,4-dinitrophenyl)ethanol is replaced by 3,5-dinitrobenzoic acid.

Example 56

4-{(1E)-3-[2-(2,4-diaminophenyl)ethoxy]-3-oxo-prop-1-enyl}phenyl 4-(4-cyanobutoxy)benzoate compound 56A 4.68 g (8.38 mmol) of compound 52A are dissolved in a mixture of 54 ml of N,N-dimethylformamide and 6 ml water. 13.9 g (51.4 mmol) ferric chloride hexahydrate are added. 5.60 g (85.7 mmol) of zinc powder are added portionwise within 60 min. The mixture is allowed to react for 2 hours. The reaction mixture is then partitioned between ethyl acetate and water and filtered. The organic phase is washed repeatedly with water, dried over sodium sulfate, filtered and concentrated by rotary evaporation. Filtration of the residue on 200 g silica gel using toluene:ethyl acetate (1:3) as eluent and crystallization from ethylacetate:hexane mixture yield 3.30 g 4-{(1E)-3-[2-(2,4-diaminophenyl)ethoxy]-3-oxoprop-1-enyl}phenyl 4-(4-cyanobutoxy)benzoate compound as yellowish crystals.

The compounds 56B, 56C, 56D, 56E, 56F, 56H, 56I, 56J, 56L, 56M, 56N, 56O, 56P, 56Q, 56R, 56S, 56T, 56U, 56V, 56W, 57A, 57B, 57C, 57D, 57E, 57F, 57G, 58A, 58B, 59, 60, 60B are prepared according to the process described in example 56 for compound 56A with the proviso that compound 52A is replaced by compound 52B, respectively 52C, respectively 52D, respectively 52E, respectively 52F, respectively 52H, respectively 52I, respectively 52J, respectively 52L, respectively 52M, respectively 52N, respectively 52O, respectively 52P, respectively 52Q, respectively 52R, respectively 52S, respectively 52T, respectively 52U, respectively 52V, respectively 52W, respectively 53A, respectively 53B, respectively 53C, respectively 53D, respectively 53E, respectively 53F, respectively 53G, respectively 54A, respectively 54B, respectively 55, respectively 55B, respectively 37C.

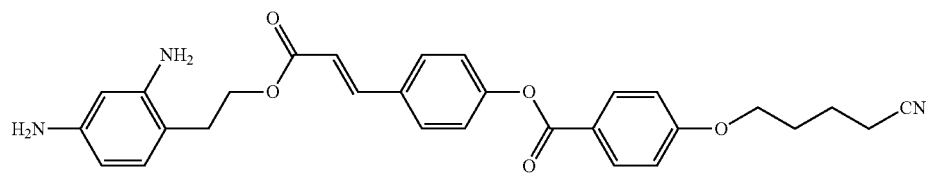

Example 61

Preparation of 4-{(1E)-3-[(8-hydroxyoctyl)oxy]-3-oxoprop-1-enyl}phenyl 4-(3-cyanopropoxy)benzoate, compound 61

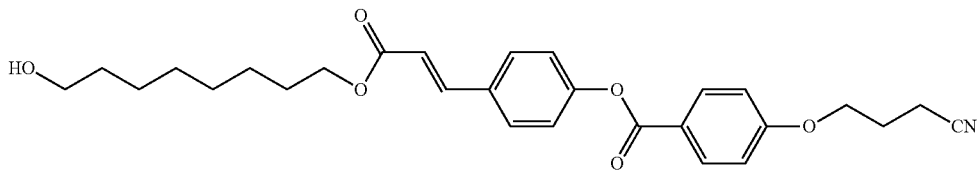 [SMILES: N#CCCCOc1ccc(C(=O)Oc2ccc(/C=C/C(=O)OCCCCCCCCO)cc2)cc1]

5 g (14.2 mmol) of (2E)-3-(4-{[4-(3-nitrilepropoxy)benzoyl]oxy}phenyl)prop-2-enoic acid described in example 2.2, 2.1 g (14.2 mmol) of 8-chlorooctan-1-ol and 0.522 g (4.3 mmol) of DMAP are dissolved in 125 mL of dichloromethane. To the above mixture, 4.1 g (21.3 mmol) of EDC are added. The mixture is allowed to react for 20 hours at room temperature. The reaction mixture is concentrated by rotary evaporation and the residue is purified by column chromatography on silica gel using ethylacetate:hexane 1:1 as eluent to yield 2.8 g of 4-{(1E)-3-[(8-hydroxyoctyl)oxy]-3-oxoprop-1-enyl}phenyl 4-(3-cyanopropoxy)benzoate as a white solid.

Example 62

Preparation of 4-((1E)-3-([8-(methacryloyloxy)octyl]oxyl-3-oxoprop-1-enyl)phenyl 4-(3-cyanopropoxy)benzoate compound 62

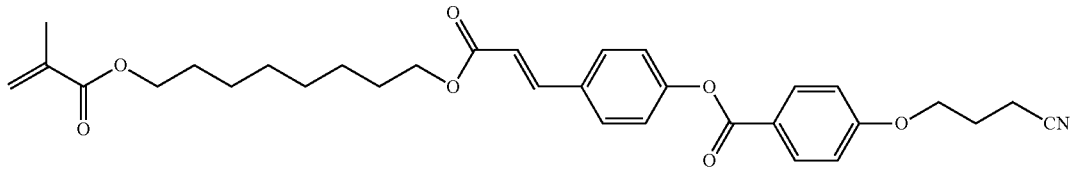

To a solution of 1.5 g (3.2 mmol) of 4-{(1E)-3-[(8-hydroxyoctyl)oxy]-3-oxoprop-1-enyl}phenyl 4-(3-cyanopropoxy)benzoate, 39 mg (0.3 mmol) of DMAP and 1 g (9.7 mmol) of triethylamine in 40 mL of THF, 0.69 g (3.9 mmol) of methacrylic anhydride is added dropwise at 0° C. After 2 h at 0° C., the reaction mixture is allowed to heat up and stir at room temperature. After 15 h, the reaction mixture is poured onto icy water. The precipitate is filtered off and dried under vacuum. Purification by column chromatography on silica gel using hexane:ethylacetate 3:8 as eluent yields to 1.7 g of pure 4-((1E)-3-{[8-(methacryloyloxy)octyl]oxy}-3-oxoprop-1-enyl)phenyl 4-(3-cyanopropoxy)benzoate as a white solid.

Example 63

Preparation of 4-{(1E)-3-[4-(2,5-dioxo-2,5-dihydro-1H-pyrrol-1-yl)phenoxy]-3-oxoprop-1-enyl}phenyl 4-(3-cyanopropoxy)benzoate compound 63

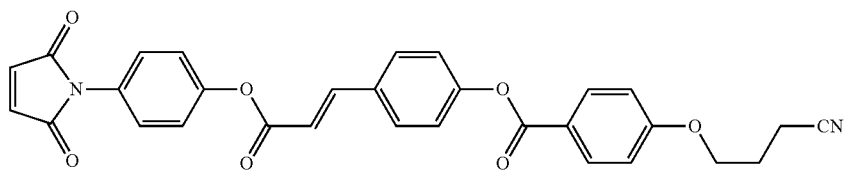 [SMILES: N#CCCCOc1ccc(C(=O)Oc2ccc(/C=C/C(=O)Oc3ccc(N4C(=O)C=CC4=O)cc3)cc2)cc1]

The compound 63 is prepared according to the process described in example 52 for compound 53A with the proviso that the 2-(2,4-dinitrophenyl)ethanol is replaced by 1-(4-hydroxyphenyl)-1H-pyrrole-2,5-dione.

Example 64

Preparation of 4-[(1E)-14,14-diethoxy-3,9-dioxo-4,8,15-trioxa-10-aza-14-silaheptadec-1-en-1-yl]phenyl 4-(3-cyanopropoxy)benzoate compound 64

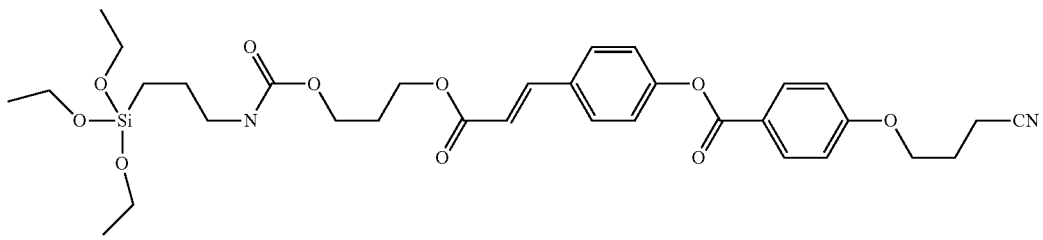 [SMILES: CCO[Si](CCCNC(=O)OCCCOC(=O)/C=C/c1ccc(OC(=O)c2ccc(OCCCC#N)cc2)cc1)(OCC)OCC]

To a solution of 2 g (4.88 mmol) of (2E)-3-(4-{[4-(3-nitrilepropoxy)benzoyl]oxy}phenyl)prop-2-enoic acid described in example 2.2 and 0.712 g (6.35 mmol) of 1,4-Diazabicyclo[2.2.2]octane in 10 mL of THF are added 1.57 ml of triethoxy(3-isocyanatopropyl)silane. The solution is allowed to stir at room temperature for 20 h. Then, the reaction mixture is then partitioned between ethyl acetate and water. The organic phase is washed repeatedly with water, dried over sodium sulfate, filtered and concentrated by rotary evaporation. Recrystallization of the residue from ethylacetate:heptane mixture yields 2.7 g of 4-[(1E)-14,14-diethoxy-3,9-dioxo-4,8,15-trioxa-10-aza-14-silaheptadec-1-en-1-yl]phenyl 4-(3-cyanopropoxy)benzoate as a white solid.

| | Name | Structure | $^1$H NMR (300 MHz) in DMSO d$_6$ |
|---|---|---|---|
| 56A | 4-{(1E)-3-[2-(2,4-diaminophenyl)ethoxy]-3-oxoprop-1-enyl}phenyl 4-(4-cyanobutoxy)benzoate | 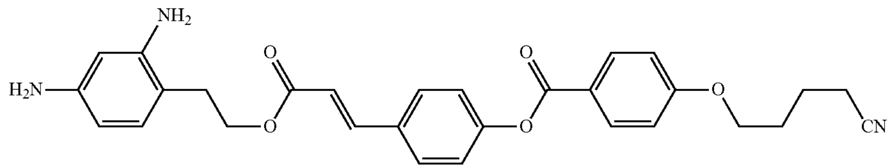 [SMILES: N#CCCCCOc1ccc(C(=O)Oc2ccc(/C=C/C(=O)OCCc3ccc(N)cc3N)cc2)cc1] | 8.10 (d, 2H), 7.84 (d, 2H), 7.69 (d, 1H), 7.33 (d, 2H), 7.13 (d, 2H), 6.66 (d, 1H), 6.61 (d, 1H), 5.91 (d, 1H), 5.81 (dd, 1H), 4.65 (s, 2H), 4.58 (s, 2H), 4.18 (t, 2H), 4.09 (t, 2H), 2.69 (t, 2H), 1.76 (m, 2H), 1.59 (m, 2H), 1.45 (m, 4H) |
| 56B | 4-{(1E)-3-[2-(2,4-diaminophenyl)ethoxy]-3-oxoprop-1-enyl}phenyl 4-[(6-cyanohexyl)oxy]benzoate | 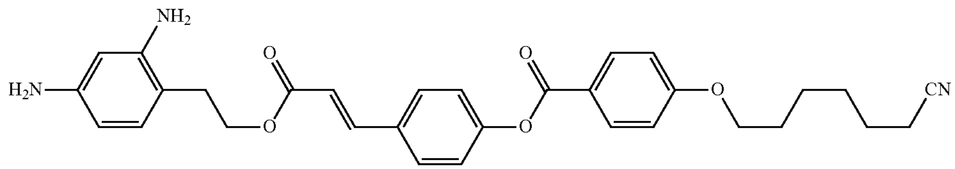 [SMILES: N#CCCCCCCOc1ccc(C(=O)Oc2ccc(/C=C/C(=O)OCCc3ccc(N)cc3N)cc2)cc1] | 8.10 (d, 2H), 7.84 (d, 2H), 7.69 (d, 1H), 7.33 (d, 2H), 7.13 (d, 2H), 6.66 (d, 1H), 6.61 (d, 1H), 5.91 (d, 1H), 5.81 (dd, 1H), 4.65 (s, 2H), 4.58 (s, 2H), 4.18 (t, 2H), 4.09 (t, 2H), 2.69 (t, 2H), 1.76 (m, 2H), 1.59 (m, 2H), 1.45 (m, 4H) |
| 56C | 4-{(1E)-3-[2-(2,4-diaminophenyl)ethoxy]-3-oxoprop-1-enyl}phenyl 4-(but-3-ynyloxy)benzoate | 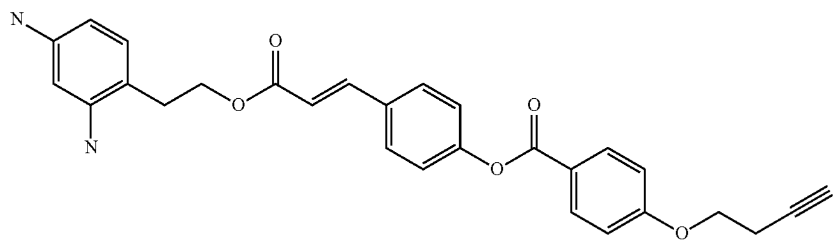 [SMILES: C#CCCOc1ccc(C(=O)Oc2ccc(/C=C/C(=O)OCCc3ccc(N)cc3N)cc2)cc1] | 8.10 (d, 2H), 7.84 (d, 2H), 7.69 (d, 1H), 7.33 (d, 2H), 7.16 (d, 2H), 6.66 (d, 1H), 6.61 (d, 1H), 5.91 (d, 1H), 5.81 (dd, 1H), 4.65 (s, 2H), 4.58 (s, 2H), 4.19 (m, 4H), 2.92 (t, 1H), 2.69 (m, 4H) |
| 56D | 4-{(1E)-3-[2-(2,4-diaminophenyl)ethoxy]-3-oxoprop-1-enyl}phenyl 4-(4-chlorobutoxy)benzoate | 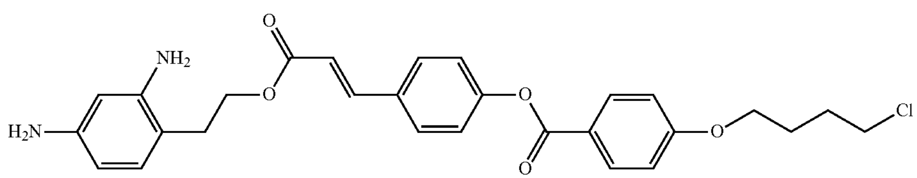 [SMILES: Nc1ccc(CCOC(=O)/C=C/c2ccc(OC(=O)c3ccc(OCCCCCl)cc3)cc2)c(N)c1] | 8.10 (d, 2H), 7.84 (d, 2H), 7.69 (d, 1H), 7.33 (d, 2H), 7.16 (d, 2H), 6.66 (d, 1H), 6.61 (d, 1H), 5.91 (d, 1H), 5.81 (dd, 1H), 4.65 (s, 2H), 4.58 (s, 2H), 4.18 (m, 4H), 3.73 (t, 2H), 2.69 (t, 2H), 1.90 (m, 4H) |

| | Name | Structure | $^1$H NMR (300 MHz) in DMSO $d_6$ |
|---|---|---|---|
| 56E | 4-[(1E)-3-[2-(2,4-diaminophenyl)ethoxy]-3-oxoprop-1-enyl]phenoxy) carbonyl]phenyl 4-benzoylbenzoate | 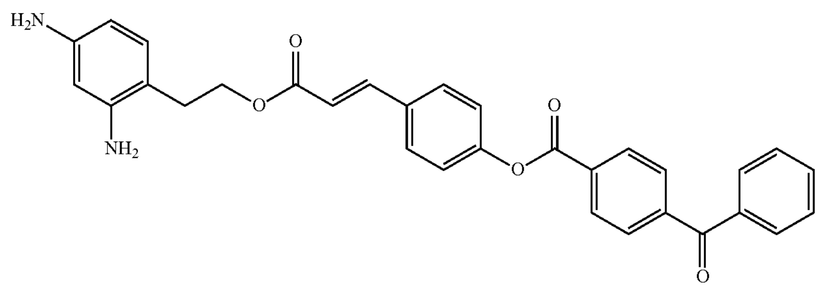 [SMILES: Nc1ccc(CCOC(=O)/C=C/c2ccc(OC(=O)c3ccc(C(=O)c4ccccc4)cc3)cc2)c(N)c1] | 8.32 (d, 2H), 7.94-7.60 (m, 6H), 7.40 (d, 2H), 6.66 (d, 1H), 6.61 (d, 1H), 5.91 (d, 1H), 5.81 (dd, 1H), 4.66 (s, 2H), 4.59 (s, 2H), 4.19 (t, 2H), 2.69 (t, 2H) |
| 56F | 4-{(1E)-3-[2-(2,4-diaminophenyl)ethoxy]-3-oxoprop-1-enyl}phenyl 4-(diethylamino)benzoate | 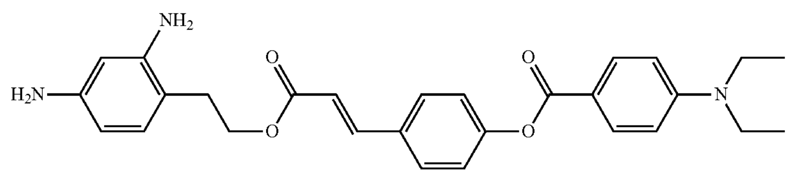 [SMILES: CCN(CC)c1ccc(C(=O)Oc2ccc(/C=C/C(=O)OCCc3ccc(N)cc3N)cc2)cc1] | 7.91 (d, 2H), 7.81 (d, 2H), 7.69 (d, 1H), 7.28 (d, 2H), 6.78 (d, 2H), 6.66 (d, 1H), 6.61 (d, 1H), 5.91 (m, 1H), 5.81 (m, 1H), 4.65 (s, 2H), 4.58 (s, 2H), 4.18 (t, 2H), 3.43 (m, 4H), 2.69 (t, 2H), 1.13 (t, 6H) |
| 56H | 4-{(1E)-3-[2-(2,4-diaminophenyl)ethoxy]-3-oxoprop-1-enyl}phenyl 4-(but-2-ynyloxy)benzoate | 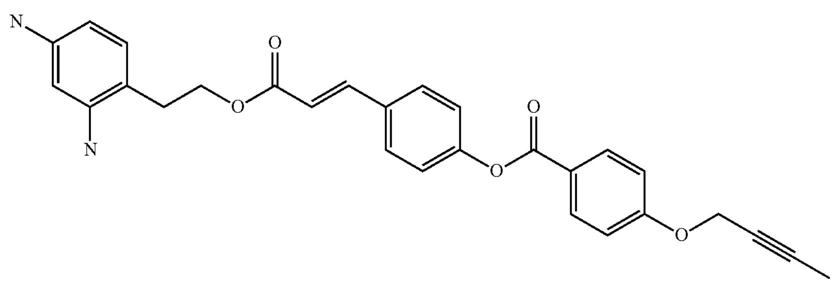 [SMILES: CC#CCOc1ccc(C(=O)Oc2ccc(/C=C/C(=O)OCCc3ccc(N)cc3N)cc2)cc1] | 8.10 (d, 2H), 7.83 (d, 2H), 7.69 (d, 1H), 7.34 (d, 2H), 7.16 (d, 2H), 6.64 (m, 2H), 5.90 (d, 1H), 5.79 (m, 1H), 4.89 (dd, 2H), 4.65 (s, 2H), 4.58 (s, 2H), 4.19 (dd, 2H), 2.70 (dd, 2H), 1.85 (s, 3H) |
| 56I | 4-{(1E)-3-[2-(2,4-diaminophenyl)ethoxy]-3-oxoprop-1-enyl}phenyl 4-(3-cyanopropoxy)-3-fluorobenzoate | 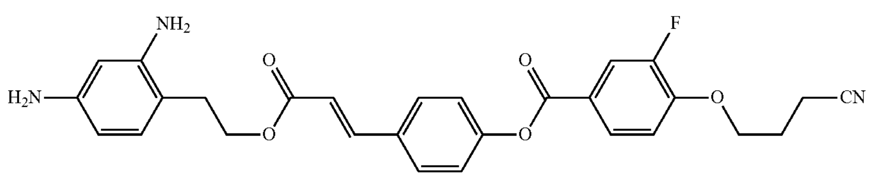 [SMILES: N#CCCCOc1ccc(C(=O)Oc2ccc(/C=C/C(=O)OCCc3ccc(N)cc3N)cc2)cc1F] | 7.94 (m, 2H), 7.83 (d, 2H), 7.69 (d, 1H), 7.41 (m, 1H), 7.35 (d, 2H), 6.64 (d, 1H), 6.62 (d, 1H), 5.90 (d, 1H), 5.81 (dd, 1H), 4.65 (s, 2H), 4.58 (s, 2H), 4.26 (dd, 2H), 4.19 (dd, 2H), 2.69 (m, 2H), 2.12 (m, 2H). |

| | Name | Structure | ¹H NMR (300 MHz) in DMSO d₆ |
|---|---|---|---|
| 56J | 4-{(1E)-3-[2-(2,4-diaminophenyl)ethoxy]-3-oxoprop-1-enyl}phenyl 4-(3-cyanopropoxy)-2,3,5,6-tetrafluorobenzoate | 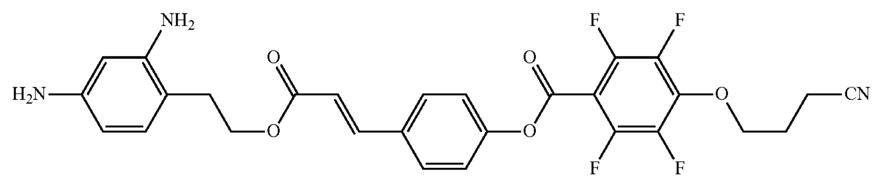 [SMILES: N#CCCCOc1c(F)c(F)c(C(=O)Oc2ccc(/C=C/C(=O)OCCc3ccc(N)cc3N)cc2)c(F)c1F] | 7.87 (d, 2H), 7.70 (d, 1H), 7.37 (d, 2H), 6.66 (d, 1H), 6.62 (m, 1H), 5.90 (d, 1H), 5.80 (dd, 1H), 4.65 (t, 2H), 4.58 (s, 2H), 4.48 (dd, 2H), 4.19 (dd, 2H), 2.69 (dd, 2H), 2.50 (m, 2H). |
| 56L | 4-{(1E)-3-[2-(2,4-diaminophenyl)ethoxy]-3-oxoprop-1-enyl}phenyl 4-(3-cyanopropoxy)-3-(trifluoromethyl)benzoate | 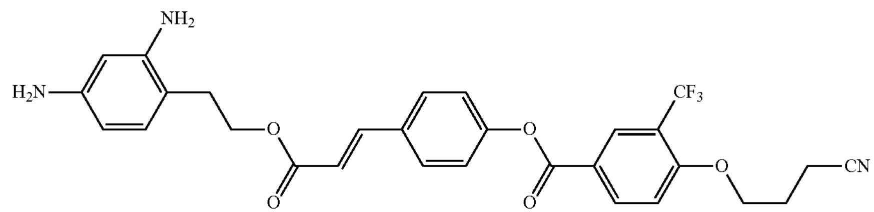 [SMILES: N#CCCCOc1ccc(C(=O)Oc2ccc(/C=C/C(=O)OCCc3ccc(N)cc3N)cc2)cc1C(F)(F)F] | 8.44 (dd, 1H), 8.29 (d, 1H), 7.85 (d, 2H), 7.70 (d, 1H), 7.53 (d, 1H), 7.37 (d, 2H), 6.66 (d, 1H), 6.62 (d, 1H), 5.90 (d, 1H), 5.80 (dd, 1H), 4.59 (m, 4H), 4.34 (dd, 2H), 4.18 (t, 2H), 2.66 (m, 4H), 2.12 (qi, 2H). |
| 56M | 4-{(1E)-3-[2-(2,4-diaminophenyl)ethoxy]-3-oxoprop-1-enyl}phenyl 4-cyanocyclohexanecarboxylate | 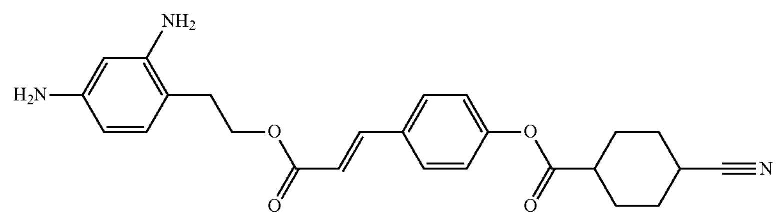 [SMILES: N#CC1CCC(C(=O)Oc2ccc(/C=C/C(=O)OCCc3ccc(N)cc3N)cc2)CC1] | 7.77 (d, 2H), 7.66 (d, 1H), 7.17 (d, 2H), 6.61 (m, 2H), 5.89 (d, 1H), 5.79 (dd, 1H), 4.62 (m, 4H), 4.17 (t, 2H), 2.73 (m, 4H), 2.08 (m, 4H), 1.60 (m, 4H). |
| 56N | 4-{(1E)-3-[2-(2,4-diaminophenyl)ethoxy]-3-oxoprop-1-enyl}phenyl 4-cyanobenzoate | 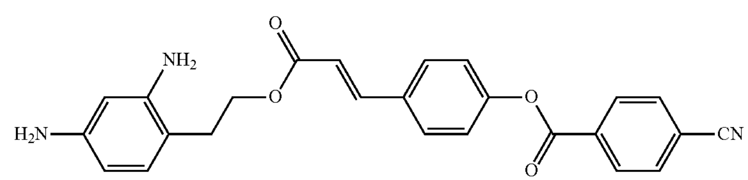 [SMILES: N#Cc1ccc(C(=O)Oc2ccc(/C=C/C(=O)OCCc3ccc(N)cc3N)cc2)cc1] | 8.29 (dd, 2H), 8.10 (dd, 2H), 7.86 (d, 2H), 7.70 (d, 1H), 7.40 (d, 2H), 6.66 (d, 1H), 6.62 (d, 1H), 5.91 (d, 1H), 5.81 (dd, 1H), 4.65 (s, 2H), 4.58 (s, 2H), 4.19 (dd, 2H), 2.70 (dd, 2H). |
| 56O | 4-{(1E)-3-[2-(2,4-diaminophenyl)ethoxy]-3-oxoprop-1-enyl}phenyl 4-(2-methoxyethoxy)benzoate | 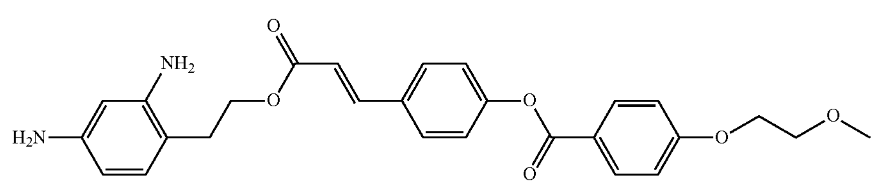 [SMILES: COCCOc1ccc(C(=O)Oc2ccc(/C=C/C(=O)OCCc3ccc(N)cc3N)cc2)cc1] | 8.09 (d, 2H), 7.84 (d, 2H), 7.69 (d, 1H), 7.33 (d, 2H), 7.16 (d, 2H), 6.66 (d, 1H), 6.61 (d, 1H), 5.91 (d, 1H), 5.81 (dd, 1H), 4.65 (s, 2H), 4.58 (s, 2H), 4.24 (m, 4H), 3.70 (m, 2H), 2.69 (t, 2H) |

| | Name | Structure | $^1$H NMR (300 MHz) in DMSO $d_6$ |
|---|---|---|---|
| 56P | 4-{(1E)-3-[2-(2,4-diaminophenyl)ethoxy]-3-oxoprop-1-enyl}-2-methoxyphenyl 4-(3-cyanopropoxy)benzoate | 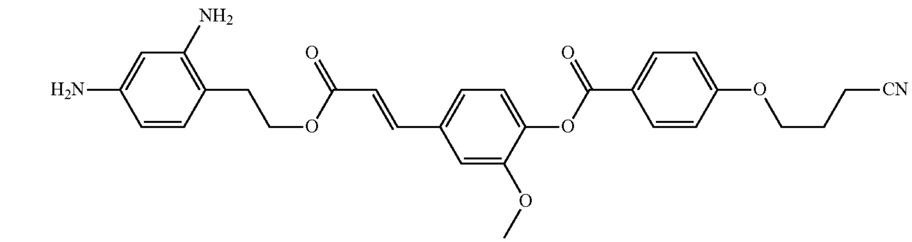 [SMILES: COc1cc(/C=C/C(=O)OCCc2ccc(N)cc2N)ccc1OC(=O)c1ccc(OCCCC#N)cc1] | 8.07 (d, 2H), 7.66 (d, 1H), 7.57 (d, 1H), 7.35 (d, 1H), 7.25 (d, 1H), 7.13 (d, 2H), 6.66 (d, 1H), 6.61 (d, 1H), 5.90 (d, 1H), 5.81 (dd, 1H), 4.65 (s, 2H), 4.58 (s, 2H), 4.18 (m, 4H), 3.81 (s, 3H), 2.69 (m, 4H), 2.07 (qi, 2H) |
| 56Q | 4-{(1E)-3-[2-(2,4-diaminophenyl)ethoxy]-3-oxoprop-1-enyl}-2-fluorophenyl 4-(3-cyanopropoxy)benzoate | 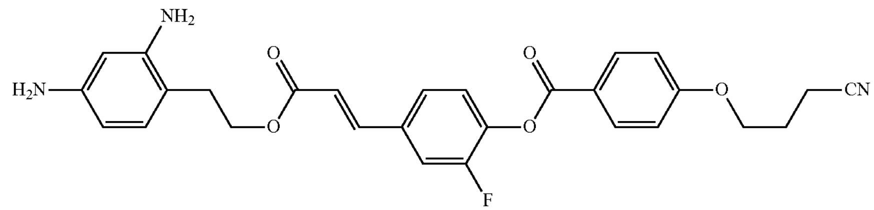 [SMILES: N#CCCCOc1ccc(C(=O)Oc2ccc(/C=C/C(=O)OCCc3ccc(N)cc3N)cc2F)cc1] | 8.11 (d, 2H), 7.91 (dd, 1H), 7.68 (d, 1H), 7.65 (m, 2H), 7.50 (dd, 1H), 7.17 (dd, 2H), 6.73 (d, 1H), 6.62 (dd, 1H), 5.90 (d, 1H), 5.81 (dd, 1H), 4.65 (s, 2H), 4.58 (s, 2H), 4.18 (t, 2H), 2.69 (t, 2H), 2.10 (m, 2H). |
| 56R | 4-{(1E)-3-[2-(2,4-diaminophenyl)ethoxy]-3-oxoprop-1-enyl}-3,5-difluorophenyl 4-[(6-cyanohexyl)oxy]benzoate | 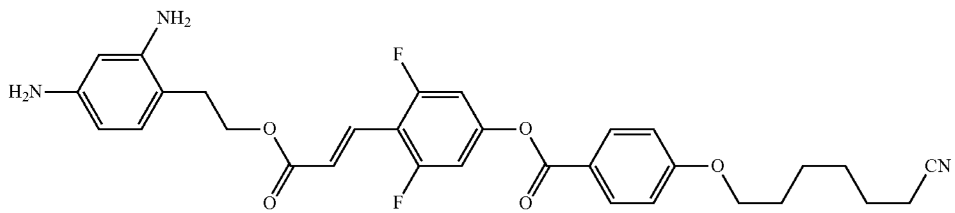 [SMILES: N#CCCCCCCOc1ccc(C(=O)Oc2cc(F)c(/C=C/C(=O)OCCc3ccc(N)cc3N)c(F)c2)cc1] | 8.07 (d, 2H), 7.61 (d, 1H), 7.37 (d, 2H), 7.13 (d, 2H), 6.63 (d, 1H), 6.60 (m, 2H), 5.90 (d, 1H), 5.80 (dd, 1H), 4.65 (s, 2H), 4.59 (s, 2H), 4.20 (t, 2H), 4.10 (t, 2H), 2.70 (t, 2H), 2.50 (m, 2H), 1.75 (m, 2H), 1.59 (m, 2H), 1.45 (m, 4H). |
| 56S | 2-(2,4-diaminophenyl)ethyl 4-{(Z)-2-cyano-2-[4-(3-cyanopropoxy)phenyl]ethenyl}benzoate | 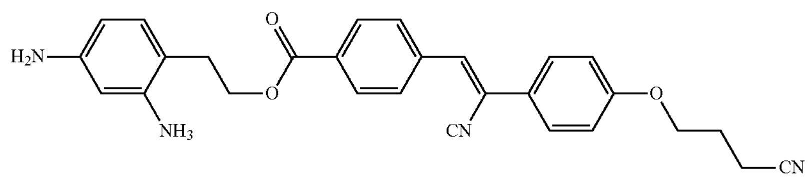 | 8.04 (m, 5H), 7.75 (d, 2H), 7.12 (m, 2H), 6.66 (d, 1H), 5.90 (d, 1H), 5.80 (dd, 1H), 4.67 (s, 4H), 4.58 (s, 2H), 4.32 (t, 2H), 4.11 (t, 2H), 2.78 (t, 2H), 2.68 (m, 2H), 2.06 (m, 2H) |
| 56T | 2-(2,4-diaminophenyl)ethyl (2E)-3-(4-{3-[4-(3-cyanopropoxy)phenoxy]propoxy}phenyl)prop-2-enoate | 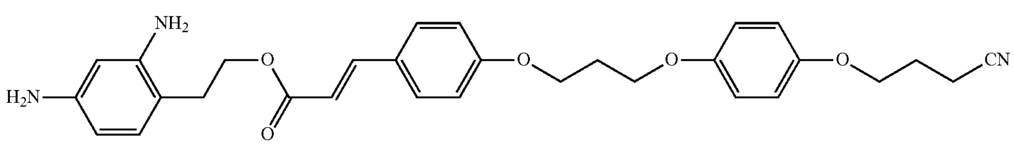 | 7.66 (d, 2H), 7.60 (d, 1H), 7.00 (d, 2H), 6.88 (s, 4H), 6.61 (d, 1H), 6.46 (d, 1H), 5.90 (d, 1H), 5.80 (dd, 1H), 4.64 (s, 2H), 4.57 (s, 2H), 4.17 (m, 4H), 4.07 (t, 2H), 3.96 (t, 2H), 2.64 (m, 2H), 2.15 (t, 2H), 1.98 (m, 2H). |

| Name | Structure | $^1$H NMR (300 MHz) in DMSO $d_6$ |
|---|---|---|
| 56U 2-(2,4-diaminophenyl)ethyl (2E)-3-{4-[3-(4-cyanophenoxy)propoxy]phenyl}prop-2-enoate | | 7.77 (d, 2H), 7.66 (d, 1H), 7.63 (s, 1H), 7.57 (s, 1H), 7.13 (d, 2H), 7.01 (d, 2H), 6.61 (d, 1H), 6.46 (d, $^3$J = 16.0 Hz, 1H), 5.90 (d, 1H), 5.80 (dd, 1H), 4.64 (s, 2H), 4.58 (s, 2H), 4.3–4.0 (m, 6H), 2.21 (dd, 2H), 2.67 (dd, 2H). |
| 56V 2-(2,4-diaminophenyl)ethyl (2E)-3-(3,4,5-trifluorophenyl)prop-2-enoate | | 7.82 (m, 2H), 7.62 (d, 1H), 6.75 (d, 1H), 6.60 (d, 1H), 5.89 (d, 1H), 5.81 (dd, 1H), 4.63 (s, 2H), 4.58 (s, 2H), 4.18 (t, 2H), 2.68 (t, 2H). |
| 56W 2-(2,4-diaminophenyl)ethyl (2E)-2-cyano-3-(4-methoxyphenyl)prop-2-enoate | | 8.31 (s, 2H), 8.08 (d, 2H), 7.16 (d, 2H), 6.64 (d, 1H), 5.90 (d, 1H), 5.81 (dd, 1H), 4.68 (s, 2H), 4.61 (s, 2H), 4.27 (dd, 2H), 3.88 (s, 3H), 2.73 (dd, 2H). |
| 57A 4-{(1E)-3-[(3,5-diaminobenzyl)oxy]-3-oxoprop-1-enyl}phenyl 4-(3-cyanopropoxy)benzoate | | 8.10 (d, 2H), 7.84 (d, 2H), 7.71 (d, 1H), 7.33 (d, 2H), 7.14 (d, 2H), 6.68 (d, 1H), 5.82 (d, 2H), 5.78 (t, 1H), 4.93 (s, 2H), 4.78 (s, 4H), 4.16 (t, 2H), 2.68 (t, 2H), 2.07 (qi, 2H) |
| 57B 4-((1E)-3-{[8-(2,4-diaminophenyl)octyl]oxy}-3-oxoprop-1-enyl)phenyl 4-(3-cyanopropoxy)benzoate | | 8.10 (d, 2H), 7.83 (d, 2H), 7.69 (d, 1H), 7.33 (d, 2H), 7.15 (d, 2H), 6.65 (d, 1H), 6.43 (d, 2H), 6.02 (dd, 1H), 4.98 (m, 4H), 4.16 (m, 6H), 2.69 (dd, 2H), 2.08 (m, 2H), 1.35 (m, 4H), 1.18 (m, 8H). |

-continued

| Name | Structure | $^1$H NMR (300 MHz) in DMSO $d_6$ |
|---|---|---|
| 57C 4-((1E)-3-{[5-(2,4-diaminophenyl)pentyl]oxy}-3-oxoprop-1-enyl)phenyl 4-(3-cyanopropoxy)benzoate | | 8.10 (dd, 2H), 7.83 (d, 2H), 7.68 (d, 1H), 7.33 (d, 2H), 7.15 (dd, 2H), 6.65 (d, 1H), 6.55 (d, 1H), 5.87 (d, 1H), 5.78 (dd, 1H), 4.47 (s, 2H), 4.45 (s, 2H), 4.16 (m, 4H), 2.69 (dd, 2H), 2.29 (dd, 2H), 2.08 (m, 2H), 1.68 (m, 2H), 1.43 (m, 4H) |
| 57D 6-{[(2E)-3-(4-{[4-(3-cyanopropoxy)benzoyl]oxy}phenyl)prop-2-enoyl]oxy}hexyl 3,5-diaminobenzoate | | 8.10 (d, 2H), 7.83 (d, 2H), 7.69 (d, 1H), 7.33 (d, 2H), 7.15 (dd, 2H), 6.65 (d, 1H), 6.44 (d, 2H), 6.03 (dd, 1H), 4.98 (s, 4H), 4.17 (m, 6H), 2.69 (dd, 2H), 2.08 (m, 2H), 1.68 (m, 4H), 1.43 (m, 4H). |
| 57E 2-(2,4-diaminophenyl)-3-{[(2E)-3-(4-{[4-(3-cyanopropoxy)benzoyl]oxy}phenyl)prop-2-enoyl]oxy}propyl (2E)-3-(4-{[4-(3-cyanopropoxy)benzoyl]oxy}phenyl)prop-2-enoate | | 8.11 (d, 4H), 7.49 (d, 2H), 7.22 (d, 4H), 7.05 (d, 4H), 6.73 (d, 1H), 6.63 (d, 2H), 5.94 (d, 1H), 5.86 (d, 1H), 4.69 (s, 2H), 4.57 (s, 2H), 4.38 (d, 4H), 4.15 (m, 4H), 3.44 (m, 1H), 2.69 (t, 4H), 2.08 (m, 4H). |

| Name | Structure | ¹H NMR (300 MHz) in DMSO d₆ |
|---|---|---|
| 57F 2,2-bis(4-aminobenzyl)-3-{[(2E)-3-(4-{[4-(3-cyanopropoxy)benzoyl]oxy}phenyl)prop-2-enoyl]oxy}propyl (2E)-3-(4-{[4-(3-cyanopropoxy)benzoyl]oxy}phenyl)prop-2-enoate | | 8.05 (d, 4H), 7.82 (d, 4H), 7.68 (d, 2H), 7.31 (d, 4H), 7.11 (d, 4H), 6.84 (d, 4H), 6.73 (d, 2H), 6.50 (d, 2H), 4.92 (s, 4H), 4.17 (dd, 4H), 3.89 (broad s, 4H), 2.69 (dd, 8H), 2.08 (m, 4H). |
| 57G 4-((1E)-3-{2-[(2E)-3-(4-{[4-(3-cyanopropoxy)benzoyl]oxy}phenyl)prop-2-enoyl]oxy}ethyl)(2,4-diaminophenyl)amino]ethoxy}-3-oxoprop-1-enyl)phenyl 4-(3-cyanopropoxy)benzoate | | 8.05 (d, 4H), 7.74 (d, 4H), 7.63 (d, 4H), 7.28 (d, 4H), 7.11 (d, 4H), 6.82 (d, 1H), 6.58 (d, 2H), 5.92 (d, 1H), 5.86 (d, 1H), 4.73 (s, 2H), 4.61 (s, 2H), 4.16 (m, 8H), 3.26 (m, 4H), 2.69 (m, 4H), 2.08 (m, 4H). |
| 58A 4-{(1E)-3-[{5-(2,4-diaminophenyl)pentyl]oxy}-3-oxoprop-1-enyl}phenyl 4-cyanobenzoate | | 8.29 (d, 2H), 8.10 (d, 2H), 7.86 (d, 2H), 7.69 (d, 1H), 7.40 (d, 1H), 6.67 (d, 1H), 6.07 (d, 1H), 5.97 (dd, 1H), 5.66 (m, 4H), 4.16 (dd, 2H), 2.34 (m, 2H), 1.71 (m, 2H), 1.50 (m, 2H), 1.40 (m, 2H). |

| | Name | Structure | ¹H NMR (300 MHz) in DMSO d₆ |
|---|---|---|---|
| 58B | 4-((1E)-3-{[5-(2,4-diaminophenyl)pentyl]oxy}-3-oxoprop-1-enyl)phenyl 4'-(3-cyanopropoxy)-1,1'-biphenyl-4-carboxylate | 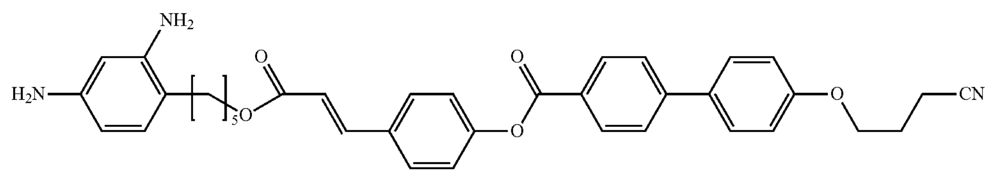 | 8.18 (d, 2H), 8.10-7.72 (m, 6H), 7.69 (d, 1H), 7.38 (d, 2H), 7.11 (d, 2H), 6.67 (d, 1H), 6.56 (d, 1H), 5.88 (d, 1H), 5.38 (m, 1H), 4.45 (m, 4H), 4.12 (m, 4H), 2.69 (m, 2H), 2.29 (m, 2H), 2.05 (m, 2H), 1.68 (m, 2H), 1.39 (m, 2H). |
| 59 | 2-(2,4-diaminophenyl)-3-{[(2E)-3-(4-{[4-(3-cyanopropoxy)-3-fluorobenzoyl]oxy}phenyl)prop-2-enoyl]oxy}propyl (2E)-3-(4-{[4-(3-cyanopropoxy)-3-fluorobenzoyl]oxy}phenyl)prop-2-enoate | 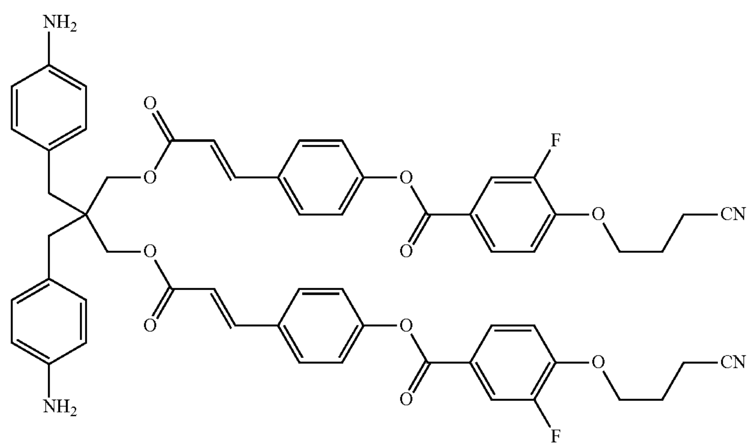 [SMILES: N#CCCCOc1ccc(C(=O)Oc2ccc(/C=C/C(=O)OCC(COC(=O)/C=C/c3ccc(OC(=O)c4ccc(OCCCC#N)c(F)c4)cc3)(Cc3ccc(N)cc3)Cc3ccc(N)cc3)cc2)cc1F] | 7.92 (dd, 2H), 7.81 (m, 6H), 7.68 (d, 2H), 7.33 (m, 6H), 6.84 (d, 4H), 6.73 (d, 2H), 6.50 (d, 4H), 4.95 (s, 4H), 4.25 (t, 4H), 3.90 (s, 4H), 2.69 (t, 8H), 2.11 (m, 4H) |
| 60 | 6-{4-[(1E)-3-(3-oxopropoxy)-3-oxoprop-1-enyl]-2-methoxyphenoxy}hexyl 3,5-diaminobenzoate | 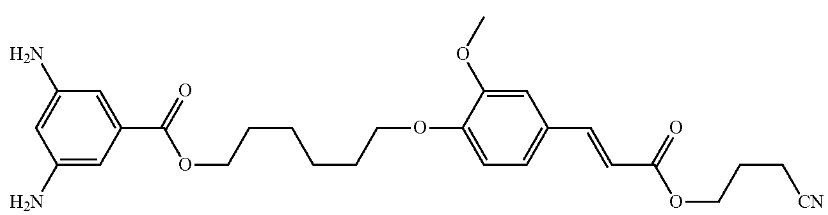 | 7.63 (d, 1H), 7.34 (d, 1H), 7.23 (d, 1H), 7.20 (d, 1H), 6.98 (d, 1H), 6.54 (d, 1H), 6.44 (d, 2H), 6.03 (dd, 1H), 4.99 (s, 4H), 4.18 (m, 4H), 4.00 (dd, 2H), 3.81 (s, 3H), 2.64 (dd, 2H), 1.96 (m, 2H), 1.71 (m, 4H), 1.46 (m, 4H). |

-continued

| | Name | Structure | $^1$H NMR (300 MHz) in DMSO $d_6$ |
|---|---|---|---|
| 60B | 6-[4-[(E)-2-cyano-3-methoxy-3-oxoprop-1-enyl]phenoxy]hexyl 3,5-diaminobenzoate | 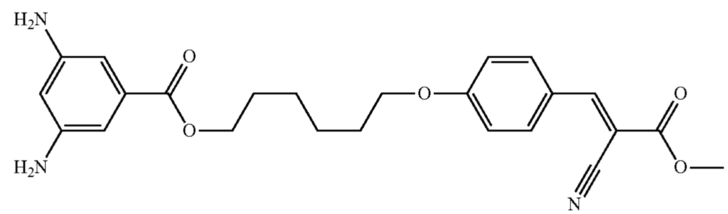 [SMILES: COC(=O)/C(C#N)=C/c1ccc(OCCCCCCOC(=O)c2cc(N)cc(N)c2)cc1] | 8.32 (s, 1H), 8.07 (d, 2H), 7.13 (d, 2H), 6.42 (d, 2H), 6.01 (d, 1H), 4.98 (s, 4H), 4.17 (t, 2H), 4.11 (t, 2H), 3.85 (s, 3H), 1.71 (m, 4H), 1.45 (m, 4H). |
| 62 | 4-((1E)-3-[8-(methacryloyloxy)octyl]oxy}-3-oxoprop-1-enyl)phenyl 4-(3-cyanopropoxy)benzoate | 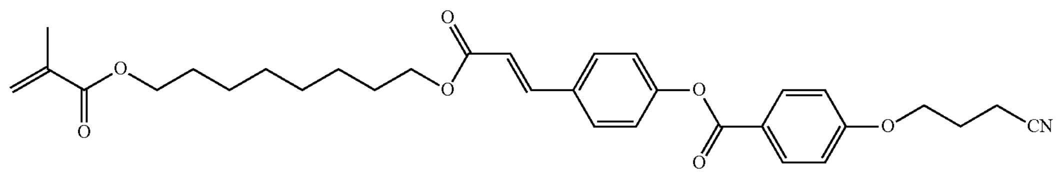 [SMILES: C=C(C)C(=O)OCCCCCCCCOC(=O)/C=C/c1ccc(OC(=O)c2ccc(OCCCC#N)cc2)cc1] | 8.10 (d, 2H), 7.83 (d, 2H), 7.69 (d, 1H), 7.33 (d, 2H), 7.15 (d, 2H), 6.65 (d, 1H), 6.01 (s, 1H), 5.66 (s, 1H), 4.16 (dd, 4H), 4.09 (dd, 2H), 2.69 (m, 2H), 2.08 (m, 2H), 1.87 (s, 3H), 1.62 (m, 4H), 1.33 (m, 6H). |
| 63 | 4-{(1E)-3-[4-(2,5-dioxo-2,5-dihydro-1H-pyrrol-1-yl]phenoxy]-3-oxoprop-1-enyl}phenyl 4-(3-cyanopropoxy)benzoate | 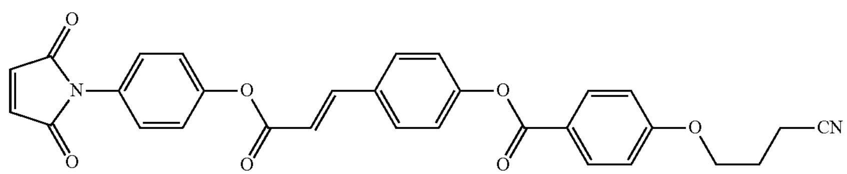 [SMILES: N#CCCCOc1ccc(C(=O)Oc2ccc(/C=C/C(=O)Oc3ccc(N4C(=O)C=CC4=O)cc3)cc2)cc1] | 8.11 (d, 2H), 7.93 (m, 3H), 7.39 (m, 6H), 7.21 (s, 2H), 7.15 (d, 2H), 6.94 (d, 1H), 4.18 (t, 2H), 2.69 (t, 2H), 2.08 (m, 2H). |
| 64 | 4-{(1E)-14,14-diethoxy-3,9-dioxo-4,8,15-trioxa-10-aza-14-silaheptadec-1-en-1-yl]phenyl 4-(3-cyanopropoxy)benzoate | 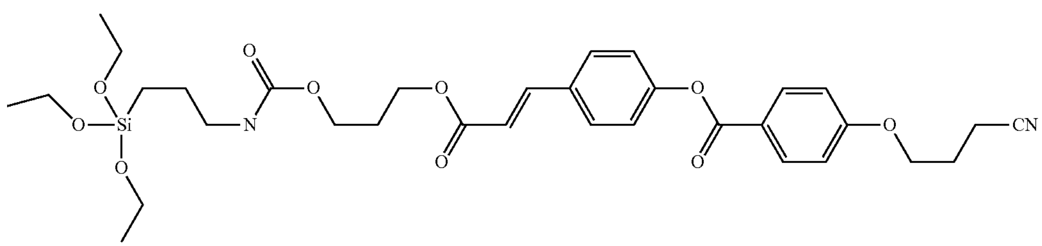 [SMILES: CCO[Si](CCCNC(=O)OCCCOC(=O)/C=C/c1ccc(OC(=O)c2ccc(OCCCC#N)cc2)cc1)(OCC)OCC] | 8.10 (d, 2H), 7.83 (m, 2H), 7.70 (d, 1H), 7.33 (d, 2H), 7.15 (m, 2H), 6.65 (d, 1H), 4.18 (t, 4H), 4.05 (t, 2H), 3.73 (q, 6H), 3.29 (s, 1H), 2.94 (q, 2H), 2.69 (t, 2H), 2.08 (qt, 2H), 1.92 (m, 2H), 1.45 (m, 2H), 1.12 (t, 9H), 0.50 (m, 2H). |

Example 65

In analogy to the preparation of PAA-1 (Example 5), Polyamic Acid PAA-10 to PAA-32b are prepared from diamines (see below table) with 1,2,3,4-cyclobutantetracarboxylic acid dianhydride. Analyticals data are given in below table.

| Diamines | Polyamic acid | Viscosity (dL/g) |
| --- | --- | --- |
| Compound 56A | PAA-10 | 0.40 |
| Compound 56B | PAA-11 | 0.41 |
| Compound 56C | PAA-12 | 0.52 |
| Compound 56D | PAA-13 | 0.36 |
| Compound 56H | PAA-14 | 0.28 |
| Compound 56I | PAA-15 | 0.30 |
| Compound 56N | PAA-16 | 0.28 |
| Compound 56J | PAA-17 | 0.41 |
| Compound 56W | PAA-18 | 0.57 |
| Compound 56O | PAA-19 | 0.50 |
| Compound 57A | PAA-20 | 1.74 |
| Compound 57B | PAA-21 | 0.36 |
| Compound 57C | PAA-22 | 0.52 |
| Compound 58B | PAA-23 | 0.19 |
| Compound 57D | PAA-24 | 0.25 |
| Compound 57E | PAA-25 | 0.12 |
| Compound 57F | PAA-26 | 1.00 |
| Compound 59 | PAA-27 | 1.11 |
| Compound 57G | PAA-28 | 0.18 |
| Compound 56L | PAA-29 | 0.27 |
| Compound 56T | PAA-30 | 0.35 |
| Compound 56S | PAA-31 | 0.37 |
| Compound 56U | PAA-32 | 0.28 |
| Compound 60B | PAA-32b | 0.26 |

Example 66

In analogy to the preparation of PAA-3 (Example 5), Polyamic Acid PAA-33 to PAA-41 are prepared from diamine (see below table) with 2,3,5-tricarboxycyclopentylacetic-1,2:3,4-dianhydride. Analyticals data are given in below table.

| Diamines | Polyamic acid | Viscosity (dL/g) |
| --- | --- | --- |
| Compound 56E | PAA-33 | 0.30 |
| Compound 56F | PAA-34 | 0.18 |
| Compound 56P | PAA-35 | 0.24 |
| Compound 56Q | PAA-36 | 0.42 |
| Compound 56V | PAA-37 | 0.30 |
| Compound 58A | PAA-38 | 0.13 |
| Compound 56M | PAA-39 | 0.19 |
| Compound 60 | PAA-40 | 0.30 |
| Compound 56R | PAA-41 | 0.25 |

Example 67

In analogy to Example 5 for the synthesis of PAA-3, the following mixture of diamines is used for the preparation of polyamic Acid with 2,3,5-tricarboxycyclopentylacetic-1,2:3,4-dianhydride.

A mixture of 2,3,5-tricarboxycyclopentylacetic-1,2:3,4-dianhydride. and compound 56V and 4-{(1E)-3-[2-(2,4-diaminophenyl)ethoxy]-3-oxoprop-1-enyl}phenyl 4-(3-nitrilepropoxy)benzoate 10:90 (mole ratio) yield Polyamic acid PAA-42 as white powder; [η]=0.33 dL/g A mixture of 2,3,5-tricarboxycyclopentylacetic-1,2:3,4-dianhydride. and compound 56V and 4-{(1E)-3-[2-(2,4-diaminophenyl)ethoxy]-3-oxoprop-1-enyl}phenyl 4-(3-nitrilepropoxy)benzoate 20:80 (mole ratio) yield Polyamic acid PAA-43 as white powder; [η]=0.23 dL/g A mixture of 2,3,5-tricarboxycyclopentylacetic-1,2:3,4-dianhydride. and compound 56E and 4-{(1E)-3-[2-(2,4-diaminophenyl)ethoxy]-3-oxoprop-1-enyl}phenyl 4-(3-nitrilepropoxy)benzoate 10:90 (mole ratio) yield Polyamic acid PAA-44 as white powder; [η]=0.27 dL/g A mixture of 2,3,5-tricarboxycyclopentylacetic-1,2:3,4-dianhydride. and compound 56E and compound 34F and 4-{(1E)-3-[2-(2,4-diaminophenyl)ethoxy]-3-oxoprop-1-enyl}phenyl 4-(3-nitrilepropoxy)benzoate 10:10:80 (mole ratio) yield Polyamic acid PAA-45 as white powder; [η]=0.19 dL/g

Example 68

In analogy to the preparation of PAA-1 (Example 5), a mixture of 4-{(1E)-3-[2-(2,4-diaminophenyl)ethoxy]-3-oxoprop-1-enyl}phenyl 4-(3-nitrilepropoxy)benzoate compound from example 2 and 2,2-Bis(1,3-dihydro-1,3-dioxobenzo[c]furan-5-yl)hexafluoropropane yield Polyamic acid PAA-46 as white powder; [η]=0.33 dL/g

Example 69

In analogy to the preparation of PAA-1 (Example 5), a mixture of 4-{(1E)-3-[2-(2,4-diaminophenyl)ethoxy]-3-oxoprop-1-enyl}phenyl 4-(3-nitrilepropoxy)benzoate compound from example 2 and ethylene bis[1,3-dihydro-1,3-dioxoisobenzofuran-5-carboxylate] yield Polyamic acid PAA-47 as white powder; [$_1$]=0.37 dL/g

Example 70

Preparation of Polyamic Acid Ester PAE-1

0.601 g (2.68 mmol) of 2,3,5-tricarboxycyclopentylacetic-1,2:3,4-dianhydride is added to a solution of 1.170 g (2.41 mmol) of 4-{(1E)-3-[2-(2,4-diaminophenyl)ethoxy]-3-oxoprop-1-enyl}phenyl 4-(3-nitrilepropoxy)benzoate and 0.050 g (0.28 mmol) of 4,4'-dihydroxybiphenyl and 0.003 g (0.02 mmol) of N,N-dimethylaminopyridine in 4.25 mL of NMP. Stirring is then carried out at 0° C. for 2 hours. The mixture is subsequently allowed to react for 21 hours at room temperature. The polymer mixture is diluted with 18 mL of THF, precipitated into 800 mL of water to yield, after drying at room temperature under vacuum, 1.04 g of polyamic acid ester PAE-1 in the form of a white powder: [η]=0.17 dL/g

Example 71

Preparation of Polymethylmethacrylate PMMA-1

1.15 g (2.1 mmol) of 4-((1E)-3-{[8-(methacryloyloxy)octyl]oxy}-3-oxoprop-1-enyl)phenyl 4-(3-cyanopropoxy)benzoate is dissolved in 4.5 mL of degassed cyclohexanone. The solution is purged with argon (several vacuum-argon cycles) and heated to 60° C. 7 mg (0.04 mmol) of 2,2'-Azobis(2-methylpropionitrile) is added to the above mixture. After 17 hours at 60° C., the reaction mixture is cooled down to room temperature, diluted with 5 mL of THF and precipitated in 200 mL of cold methanol. The precipitate is filtered off, washed with methanol and dried under vacuum at 30° C. to yield 1.0 g of PMMA-1 as a white solid.

Size-exclusion chromatography (PS-equivalent), Mw: 108500.

Example 72

Preparation of Polymaleimide PM-1

In analogy to the preparation of PMMA-1, PM-1 is prepared from 4-{(1E)-3-[4-(2,5-dioxo-2,5-dihydro-1H-pyrrol-1-yl)phenoxy]-3-oxoprop-1-enyl}phenyl 4-(3-cyanopropoxy)benzoate compound 63: [η]=0.10 dL/g

Example 73

Preparation of Polysiloxane PS-1

To a solution of 0.830 mg (1.3 mmol) of 4-[(1E)-14,14-diethoxy-3,9-dioxo-4,8,15-trioxa-10-aza-14-silaheptadec-1-en-1-yl]phenyl 4-(3-cyanopropoxy)benzoate compound 64 dissolved in 2 mL of dry THF, 50 ul of $H_2O$ and 24 ul of a 10% HCl solution are added. The mixture is stirred for 48 hours at room temperature. 3 ml of THF is added to the above solution. Then, the reaction mixture is precipitated in 100 ml of MeOH. The precipitate is filtered off, washed with methanol and dried under vacuum at 40° C. to yield 0.58 g of PS-1 as a white solid. Mw: [η]=0.10 dL/g

Example 74

Preparation of Polyimide PI-4

6.50 g of polyamic acid PAA-3 obtained in above are dissolved in 58.5 ml of NMP. Thereto are added 5.1 mL of triethylamine and 3.4 mL of acetic acid anhydride. The dehydration and ring closure is carried out at 80° C. for 16 h. The polymer mixture is diluted with 58 ml of NMP, precipitated into 500 ml diethyl ether and collected by filtration. The polymer is reprecipitated from THF (50 ml) into 500 ml water to yield, after drying at room temperature under vacuum, 5.16 g of polyimide, PI-4, as an off-white powder. Imidization degree 100%

Example 75

Preparation of Polyimide PI-5

2.1 g of polyamic acid PAA-2 obtained in above are dissolved in 8.5 g of NMP. Thereto are added 0.625 g of triethylamine and 0.630 g of acetic acid anhydride. The dehydration and ring closure is carried out at room temperature for 20 h. The polymer mixture is diluted with 10 g of NMP, precipitated into 250 ml of water and collected by filtration to yield, after drying at room temperature under vacuum, 2 g of polyimide, PI-5, as an off-white powder. Imidization degree 100%

Example 76

Preparation of Polyimide PI-6

1 g of polyamic acid PAA-2 obtained in above are dissolved in 8.6 g of NMP. Thereto are added 0.058 g of pyridine and 0.075 g of acetic acid anhydride. The dehydration and ring closure is carried out at 80° C. for 2 h. The polymer mixture is diluted with 4.8 g of NMP, precipitated into 250 ml of water and collected by filtration to yield, after drying at room temperature under vacuum, 0.6 g of polyimide, PI-6, as an off-white powder. Imidization degree 70%

Example 77

Preparation of Polyimide PI-7

1 g of polyamic acid PAA-2 obtained in above are dissolved in 8.6 g of NMP. Thereto are added 0.148 g of triethylamine and 0.150 g of acetic acid anhydride. The dehydration and ring closure is carried out at room temperature for 2 h. The polymer mixture is diluted with 4.7 g of NMP, precipitated into 200 ml of water and collected by filtration to yield after drying at room temperature under vacuum, 0.8 g polyimide, PI-4, as an off-white powder. Imidization degree 40%

Application Examples

Example A

Cells are prepared with PAA-10,11,12,13,14,15,16,17,18, 19,20,21,22,23,24,26 and 27 as in Example 10, except that the liquid crystal mixture used is MLC-7067 (Merck Ltd.). Alignment quality of the liquid crystal in the cell is checked by placing the cell between two crossed polarizers and adjusted to obtain dark state. The alignment quality is defined to be good, if the dark state show no defects and the liquid crystal is well oriented. The alignment quality is defined to be medium if the dark state has light leakage because of slight inhomogeneous orientation of liquid crystal in some areas of the cell. The alignment quality is defined to be worse, if liquid crystal is not oriented with absence of dark state. Pre-tilt angle is measured using the rotating analyser method. Voltage holding ratio (VHR) of the cells is measured as in Example 27 at frame period of 20 ms. The results are summarized in the Table 1 below.

TABLE 1

| Compound | Alignment quality | Pretilt | VHR |
| --- | --- | --- | --- |
| PAA-10 | Good | 0.11° | >99.5% |
| PAA-11 | Good | 0.06° | >99.5% |
| PAA-12 | Good | 0.09° | >99.5% |
| PAA-13 | Good | 0.09° | >99.5% |
| PAA-14 | Good | 0.1° | >99.5% |
| PAA-15 | Good | 0.2° | >99.5% |
| PAA-16 | Medium | 0.02° | >99.5% |
| PAA-17 | Good | 0.13° | >99.5% |
| PAA-18 | Medium | 0.001° | >99.5% |
| PAA-19 | Good | 0.03° | >99.5% |
| PAA-20 | Good | 0.163° | >99.5% |
| PAA-21 | Medium | 0.214° | >99.5% |
| PAA-22 | Good | 0.09° | >99.5% |
| PAA-23 | Medium | 0.03° | >99.5% |
| PAA-24 | Good | 0.015° | >99.5% |
| PAA-26 | Good | 0.1° | >99.5% |
| PAA-27 | Good | 0.21° | >99.5% |

Example B

Cells are prepared with PAA-10,11,12,13,14,15,16,17,18, 19,20,21,22,23,24,26 and 27 as in Example A, except that the exposure dose is 100 mJ/cm$^2$. The cells are characterized as in Example A. The results are summarized in the Table 2 below.

TABLE 2

| Compound | Alignment quality | Pretilt | VHR |
|---|---|---|---|
| PAA-10 | Good | 0.10° | >99.5% |
| PAA-11 | Good | 0.061° | >99.5% |
| PAA-12 | Good | 0.092° | >99.5% |
| PAA-13 | Good | 0.088° | >99.5% |
| PAA-14 | Good | 0.09° | >99.5% |
| PAA-15 | Good | 0.18° | >99.5% |
| PAA-16 | Medium | 0.023° | >99.5% |
| PAA-17 | Good | 0.13° | >99.5% |
| PAA-18 | Medium | 0.013° | >99.5% |
| PAA-19 | Good | 0.028° | >99.5% |
| PAA-20 | Good | 0.15° | >99.5% |
| PAA-21 | Medium | 0.22° | >99.5% |
| PAA-22 | Good | 0.08° | >99.5% |
| PAA-23 | Medium | 0.025° | >99.5% |
| PAA-24 | Good | 0.018° | >99.5% |
| PAA-26 | Good | 0.12° | >99.5% |
| PAA-27 | Good | 0.2° | >99.5% |

Example C

Cells are prepared with PAA-28,29,30,31,32,33,34,35,36,38,39,41,43,44,45,46,47, PMMA-1 and PM-1 as in Example A. The cells are characterized as in Example A. The results are summarized in the Table 3 below.

TABLE 3

| Compound | Alignment quality | Pretilt | VHR |
|---|---|---|---|
| PAA-28 | Good | 0.06° | >99.5% |
| PAA-29 | Good | 0.04° | >99.5% |
| PAA-30 | Medium | 0.12° | >99.5% |
| PAA-31 | Good | 0.01° | >99.5% |
| PAA-32 | Medium | 0.01° | >99.5% |
| PAA-33 | Medium | 0.08° | >99.5% |
| PAA-34 | Medium | 0.12° | >99.5% |
| PAA-35 | Good | 0.01° | >99.5% |
| PAA-36 | Good | 0.02° | >99.5% |
| PAA-38 | Medium | 0.07° | >99.5% |
| PAA-39 | Good | 0.5° | >99.5% |
| PAA-41 | Good | 0.12° | >99.5% |
| PAA-43 | Good | 0.015° | >99.5% |
| PAA-44 | Good | 0.016° | >99.5% |
| PAA-45 | Good | 0.012° | >99.5% |
| PAA-46 | Good | 0.19° | >99.5% |
| PAA-47 | Medium | | |
| PMMA-1 | Medium | | |
| PM-1 | Good | 0.45° | >99.5% |

Example D

Cells are prepared with PAA-28,29,30,31,32,33,34,35,36,38,39,40,41,43,44,45,46,47, PMMA-1 and PM-1 as in Example C, except that the exposure dose is 100 mJ/cm². The cells are characterized as in Example C. The results are summarized in the Table 4 below.

TABLE 4

| Compound | Alignment quality | Pretilt | VHR |
|---|---|---|---|
| PAA-28 | Good | 0.05° | >99.5% |
| PAA-29 | Good | 0.05° | >99.5% |
| PAA-30 | Medium | 0.13° | >99.5% |
| PAA-31 | Good | 0.012° | >99.5% |
| PAA-32 | Good | 0.011° | >99.5% |
| PAA-32b | Medium | 0.09° | >99.5% |
| PAA-33 | Medium | 0.08° | >99.5% |
| PAA-34 | Medium | 0.11° | >99.5% |
| PAA-35 | Good | 0.03° | >99.5% |
| PAA-36 | Good | 0.02° | >99.5% |
| PAA-38 | Medium | 0.055° | >99.5% |
| PAA-39 | Good | 0.46° | >99.5% |
| PAA-40 | Medium | 0.11° | >99.5% |
| PAA-41 | Good | 0.122° | >99.5% |
| PAA-43 | Good | 0.011° | >99.5% |
| PAA-44 | Good | 0.013° | >99.5% |
| PAA-45 | Good | 0.011° | >99.5% |
| PAA-46 | Good | 0.17° | >99.5% |
| PAA-47 | Medium | | |
| PMMA-1 | Medium | | |
| PM-1 | Good | 0.43° | >99.5% |

Example E

Cells are prepared with PI-3,4,5,6 and 7 as in Example A. The cells are characterized as in Example A. The results are summarized in the Table 5 below.

TABLE 5

| Compound | Alignment quality | Pretilt | VHR |
|---|---|---|---|
| PI-3 | Good | 0.026° | >99.5% |
| PI-4 | Good | 0.024° | >99.5% |
| PI-5 | Good | 0.033° | >99.5% |
| PI-6 | Good | 0.05° | >99.5% |
| PI-7 | Good | 0.055° | >99.5% |

Example F

Cells are prepared in Example A except that the polymer solution used is a blend of PAA3 and PI-6 in ratio of 50:50 by wt %. The cells are characterized as in Example A. The alignment quality is good. A pretilt of 0.026° is measured using the rotating analyser method. Voltage holding ratio of the cell is 99.76%.

The invention claimed is:

1. Polymer or oligomer comprising a compound of formula (I') as one basic building block:

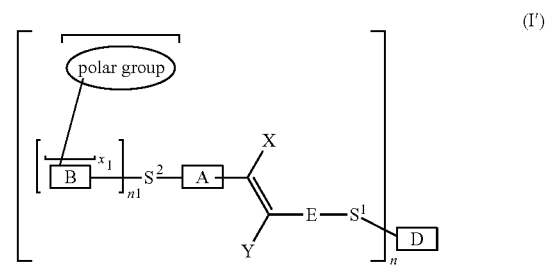

(I')

wherein,

A represents an unsubstituted or substituted carbocyclic or heterocyclic aromatic group selected from a monocyclic ring of five or six atoms, two adjacent monocyclic rings of five or six atoms, a bicyclic ring system of eight, nine or ten atoms, or a tricyclic ring system of thirteen or fourteen atoms or a group "E";

and wherein the following compound residue of formula (I'), the compound residue (Ia)

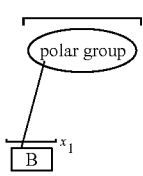

(Ia)

represents a straight-chain or branched $C_1$-$C_{16}$alkyl group having at least one terminal polar group, which is di-($C_1$-$C_{16}$alkyl)amino, nitrile, pyridyl, unsubstituted or substituted straight-chain or branched alkynyl or $C_1$-$C_6$alkyloxy;

x1 is an integer from 1 to 15,

B represents a straight-chain or branched $C_1$-$C_{16}$alkyl group, wherein one or more —C—, —CH—, —CH$_2$— or —CH$_3$ group may independently from each other be unreplaced or replaced by at least one heteroatom and/or by a primary, secondary, tertiary or quaternary nitrogen and/or a linking group, which is an unsubstituted or substituted alicyclic group, an unsubstituted or substituted aromatic group, single bond, heteroatom, cationic carbohydrogen group, —CO, -arylen-, —CO—O—, —O—CO—, —CN, —NR$^1$—, —NR$^1$—CO—, —CO—NR$^1$—, —NR$^1$—CO—O—, —O—CO—NR$^1$—, —NR$^1$—CO—NR$^1$—, —CH=CH—, —C≡C—, —O—CO—O—, or —Si(CH$_3$)$_2$—O—Si(CH$_3$)$_2$—, and wherein:

$R^1$ represents a hydrogen atom or $C_1$-$C_6$alkyl;

with the proviso that oxygen atoms of linking groups are not directly linked to each other;

D represents a polymerizable group, which is an unsubstituted or substituted, aliphatic, aromatic and/or alicyclic diamine group, siloxane or maleinimide;

E represents an aromatic group, a single bond, an oxygen atom, a sulphur atom, —NH—, —N($C_1$-$C_6$alkyl)-, —CR$^2$R$^3$, —OCO—, —COO—, —OOC—, —NHCO—, —CONH—, —CONR$^2$—, —NR$^2$CO—, —SCS—, or —CO— wherein $R^2$ and $R^3$ are independently from each other hydrogen or a cyclic, straight-chain or branched, substituted or unsubstituted $C_1$-$C_{24}$alkyl, wherein one or more —C—, —CH—, —CH$_2$— group(s) may be independently from each other unreplaced or replaced by a linking group, and with the proviso that at least one of $R^2$ and $R^3$ is not hydrogen;

$S^1$, $S^2$ each independently from each other represents a spacer unit, which is a single bond, a cyclic, straight-chain or branched, substituted or unsubstituted $C_1$-$C_{24}$alkylen, wherein one or more —C—, —CH—, or —CH$_2$— group may independently from each other be unreplaced or replaced by at least one linking group as described above and/or by at least one non-aromatic, aromatic, unsubstituted or substituted carbocyclic or heterocyclic group connected via bridging groups;

X, Y each independently from each other represents hydrogen, fluorine, chlorine, nitrile, or unsubstituted or with fluorine substituted $C_1$-$C_{12}$alkyl, in which one or more —CH$_2$— groups may be unreplaced or replaced by a linking group, n, n1 each independently from each other represents 1, 2, 3 or 4, with the proviso that if n is 2, 3, or 4, each A, B, $x_1$, E, $S^1$, $S^2$, X, Y are identical or different; and if n1 is 2, 3 or 4 each B, $x_1$ is identical or different; and with the proviso that if B is substituted with at least one fluorine then there is at least one additional polar group in formula (I').

2. Copolymer comprising (i) a compound of formula (I')

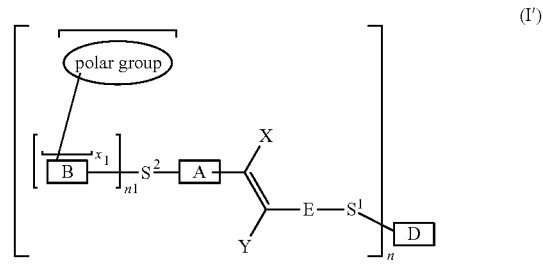

(I')

wherein,

A represents an unsubstituted or substituted carbocyclic or heterocyclic aromatic group selected from a monocyclic ring of five or six atoms, two adjacent monocyclic rings of five or six atoms, a bicyclic ring system of eight, nine or ten atoms, or a tricyclic ring system of thirteen or fourteen atoms or a group "E";

and wherein the following compound residue of formula (I'), the compound residue (Ia)

(Ia)

represents a straight-chain or branched $C_1$-$C_{16}$alkyl group having at least one terminal polar group, which is di-($C_1$-$C_{16}$alkyl)amino, nitrile, pyridyl, unsubstituted or substituted straight-chain or branched alkynyl or $C_1$-$C_6$alkyloxy;

x1 is an integer from 1 to 15,

B represents a straight-chain or branched $C_1$-$C_{16}$alkyl group, wherein one or more —C—, —CH—, —CH$_2$— or —CH$_3$ group may independently from each other be unreplaced or replaced by at least one heteroatom and/or by a primary, secondary, tertiary or quaternary nitrogen and/or a linking group, which is an unsubstituted or substituted alicyclic group, or an unsubstituted or substituted aromatic group, single bond, heteroatom, cationic carbohydrogen group, —CO, -arylen-, —CO—O—, —O—CO—, —CN, —NR$^1$—, —NR$^1$—CO—, —CO—NR$^1$—, —NR$^1$—CO—O—, —O—CO—NR$^1$—, —NR$^1$—CO—NR$^1$—, —CH=CH—, —C≡C—, —O—CO—O—, or —Si(CH$_3$)$_2$—O—Si(CH$_3$)$_2$—, and wherein:

$R^1$ represents a hydrogen atom or $C_1$-$C_6$alkyl;

with the proviso that oxygen atoms of linking groups are not directly linked to each other;

D represents a polymerizable group, which is an unsubstituted or substituted, aliphatic, aromatic and/or alicyclic diamine group, siloxane or maleinimide;

E represents an aromatic group, a single bond, an oxygen atom, a sulphur atom, —NH—, —N($C_1$-$C_6$alkyl)-, —$CR^2R^3$, —OCO—, —COO—, —OOC—, —NHCO—, —CONH—, —$CONR^2$—, —$NR^2CO$—, —SCS—, or —CO— wherein $R^2$ and $R^3$ are independently from each other hydrogen or a cyclic, straight-chain or branched, substituted or unsubstituted $C_1$-$C_{24}$alkyl, wherein one or more —C—, —CH—, —$CH_2$— group(s) may be independently from each other unreplaced or replaced by a linking group, and with the proviso that at least one of $R^2$ and $R^3$ is not hydrogen;

$S^1$, $S^2$ each independently from each other represents a spacer unit, which is a single bond, a cyclic, straight-chain or branched, substituted or unsubstituted $C_1$-$C_{24}$alkylen, wherein one or more —C—, —CH—, or —$CH_2$— group may independently from each other be unreplaced or replaced by at least one linking group as described above and/or by at least one non-aromatic, aromatic, unsubstituted or substituted carbocyclic or heterocyclic group connected via bridging groups;

X, Y each independently from each other represents hydrogen, fluorine, chlorine, nitrile, or unsubstituted or with fluorine substituted $C_1$-$C_{12}$alkyl, in which one or more —$CH_2$— groups may be unreplaced or replaced by a linking group, n, n1 each independently from each other represents 1, 2, 3 or 4, with the proviso that if n is 2, 3, or 4, each A, B, $x_1$, E, $S^1$, $S^2$, X, Y are identical or different; and if n1 is 2, 3 or 4 each B, $x_1$ is identical or different; and with the proviso that if B is substituted with at least one fluorine then there is at least one additional polar group in formula (I'), and (ii) a further compound of formula (I') wherein B is substituted by one, two, three, four, five, six or seven fluorine atoms.

3. Process for the preparation of a polymer or oligomer according to claim 1 comprising polymerisation of a compound of formula (I'), wherein the compound is a diamine.

4. Polymer or oligomer according to claim 1, obtainable by a process comprising polymerisation of a compound of formula (I'), wherein the compound is a diamine.

5. Composition comprising a polymer or oligomer according to claim 1 which is a diamine as basic building block.

6. Orientation layer, comprising at least one polymer or oligomer according claim 1.

7. Method for the preparation of a polymer layer or oligomer layer, wherein one or more polymers or oligomers according to claim 1 is treated with aligning light.

8. Polymer or oligomer layer which is an orientation layer obtainable by the method according to claim 7.

9. Polymer or oligomer layer according to claim 8 for the planar alignment of liquid crystals.

10. Method of using an orientation layer according to claim 6 for the alignment of a) a liquid crystal composition comprising a polymerizable monomer, polymer or oligomer, which is the polymerized form of said polymerizable monomer, and/or b) liquid crystals, which are sandwiched between a pair of polymer films made from b1) at least one polymerizable monomer in said liquid crystal material and/or b2) at least a single polymerizable liquid crystal, LCP;
and which polymer films are formed on polymer or oligomer layers, comprising aligning the liquid crystal composition and/or the liquid crystals with the orientation layer.

11. Method for manufacturing a liquid crystal display comprising applying at least a single LCP onto a polymer or oligomer layer as described in claim 8 and polymerizing said LCP.

12. Optical or electro-optical unstructured or structured elements, comprising at least one polymer or oligomer layer according to claim 8.

13. Polymer or oligomer layer according to claim 8, wherein n1 is 1.

14. Copolymer according to claim 2, wherein the compound of formula (I') is a diamine and the further compound of formula (I') is a diamine.

15. Polymer or oligomer according to claim 1, comprising a compound of formula (I') wherein the following compound residue of formula (I'), the compound residue (Ia)

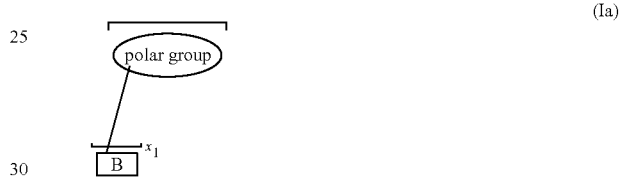

(Ia)

represents a straight-chain or branched $C_1$-$C_{16}$alkyl group having at least one terminal polar group, which is pyridyl.

16. Polymer or oligomer according to claim 1, comprising a compound of formula (I') wherein the following compound residue of formula (I'), the compound residue (Ia)

(Ia)

represents a straight-chain or branched $C_1$-$C_{16}$alkyl group having at least one terminal polar group, which is unsubstituted or substituted straight-chain or branched alkynyl.

17. Polymer or oligomer according to claim 1, comprising a compound of formula (I') wherein the following compound residue of formula (I'), the compound residue (Ia)

(Ia)

represents a straight-chain or branched $C_1$-$C_{16}$alkyl group having at least one terminal polar group, which is nitrile.

18. Polymer or oligomer according to claim 1, comprising a compound of formula (I') wherein the following compound residue of formula (I'), the compound residue (Ia)

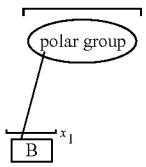

(Ia)

represents a straight-chain or branched $C_1$-$C_{16}$alkyl group having at least one terminal polar group, which is $C_1$-$C_6$ alkyloxy.

19. Polymer or oligomer according to claim 1, comprising a compound of formula (I') wherein the following compound residue of formula (I'), the compound residue (Ia)

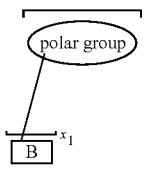

(Ia)

represents a straight-chain or branched $C_1$-$C_{16}$alkyl group having at least one terminal polar group, which is di-($C_1$-$C_{16}$-alkyl)amino.

20. Copolymer according to claim 2, comprising (i) a compound of formula (I') wherein the following compound residue of formula (I'), the compound residue (Ia)

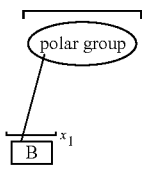

(Ia)

represents a straight-chain or branched $C_1$-$C_{16}$alkyl group having at least one terminal polar group, which is pyridyl.

21. Copolymer according to claim 2, comprising (i) a compound of formula (I') wherein the following compound residue of formula (I'), the compound residue (Ia)

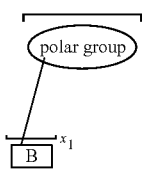

(Ia)

represents a straight-chain or branched $C_1$-$C_{16}$alkyl group having at least one terminal polar group, which is unsubstituted or substituted straight-chain or branched alkynyl.

22. Copolymer according to claim 2, comprising (i) a compound of formula (I') wherein the following compound residue of formula (I'), the compound residue (Ia)

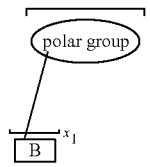

(Ia)

represents a straight-chain or branched $C_1$-$C_{16}$alkyl group having at least one terminal polar group, which is nitrile.

23. Copolymer according to claim 2, comprising (i) a compound of formula (I') wherein the following compound residue of formula (I'), the compound residue (Ia)

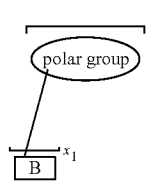

(Ia)

represents a straight-chain or branched $C_1$-$C_{16}$alkyl group having at least one terminal polar group, which is $C_1$-$C_6$ alkyloxy.

24. Copolymer according to claim 2, comprising (i) a compound of formula (I') wherein the following compound residue of formula (I'), the compound residue (Ia)

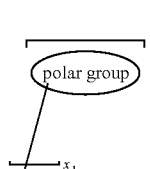

(Ia)

represents a straight-chain or branched $C_1$-$C_{16}$alkyl group having at least one terminal polar group, which is di-($C_1$-$C_{16}$-alkyl)amino.

25. Polymer or oligomer according to claim 1, comprising a compound of formula (I') as one basic building block:

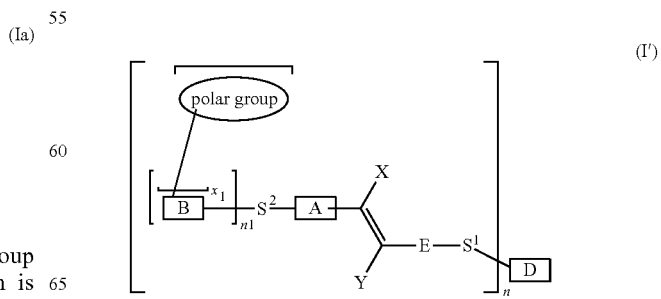

(I')

wherein,

A represents a substituted or unsubstituted phenylene group;

and wherein the following compound residue of formula (I'), the compound residue (Ia)

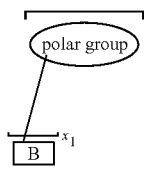

(Ia)

represents a straight-chain or branched $C_1$-$C_{16}$alkyl group having at least one terminal polar group, which is nitrile;

x1 is an integer from 1 to 15,

B represents a straight-chain or branched $C_1$-$C_{16}$alkyl group, wherein one or more —C—, —CH—, —CH$_2$— or —CH$_3$ group may independently from each other be unreplaced or replaced by at least one heteroatom and/or by a primary, secondary, tertiary or quaternary nitrogen and/or a linking group, which is an unsubstituted or substituted alicyclic group, an unsubstituted or substituted aromatic group, single bond, heteroatom, cationic carbohydrogen group, —CO, -arylen-, —CO—O—, —O—CO—, —CN, —NR$^1$—, —NR$^1$—CO—, —CO—NR$^1$—, —NR$^1$—CO—O—, —O—CO—NR$^1$—, —NR$^1$—CO—NR$^1$—, —CH═CH—, —C≡C—, —O—CO—O—, or —Si(CH$_3$)$_2$—O—Si(CH$_3$)$_2$—, and wherein:

$R^1$ represents a hydrogen atom or $C_1$-$C_6$alkyl;

with the proviso that oxygen atoms of linking groups are not directly linked to each other;

D represents a polymerizable group, which is an unsubstituted or substituted, aliphatic, aromatic and/or alicyclic diamine group, siloxane or maleinimide;

E represents —OCO—, —COO—, —OOC—, or —CO—;

$S^1$, $S^2$ each independently from each other represents a spacer unit, which is a single bond, a cyclic, straight-chain or branched, substituted or unsubstituted $C_1$-$C_{24}$alkylen, wherein one or more —C—, —CH—, or —CH$_2$— group may independently from each other be unreplaced or replaced by at least one linking group as described above and/or by at least one non-aromatic, aromatic, unsubstituted or substituted carbocyclic or heterocyclic group connected via bridging groups;

X, Y represent hydrogen;

n, n1 each independently from each other represents 1, 2, 3 or 4, with the proviso that if n is 2, 3, or 4, each A, B, $x_1$, E, $S^1$, $S^2$, X, Y are identical or different; and if n1 is 2, 3 or 4 each B, $x_1$ is identical or different; and with the proviso that if B is substituted with at least one fluorine then there is at least one additional polar group in formula (I').

26. Copolymer according to claim 2, comprising (i) a compound of formula (I')

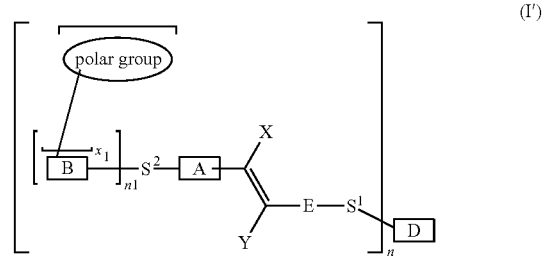

(I')

wherein,

A represents a substituted or unsubstituted phenylene group;

and wherein the following compound residue of formula (I'), the compound residue (Ia)

(Ia)

represents a straight-chain or branched $C_1$-$C_{16}$alkyl group having at least one terminal polar group, which is nitrile;

x1 is an integer from 1 to 15,

B represents a straight-chain or branched $C_1$-$C_{16}$alkyl group, wherein one or more —C—, —CH—, —CH$_2$— or —CH$_3$ group may independently from each other be unreplaced or replaced by at least one heteroatom and/or by a primary, secondary, tertiary or quaternary nitrogen and/or a linking group, which is an unsubstituted or substituted alicyclic group, an unsubstituted or substituted aromatic group, single bond, heteroatom, cationic carbohydrogen group, —CO, -arylen-, —CO—O—, —O—CO—, —CN, —NR$^1$—, —NR$^1$CO—, —CO—NR$^1$—, —NR$^1$—CO—O—, —O—CO—NR$^1$—, —NR$^1$—CO—NR$^1$—, —CH═CH—, —C≡C, —O—CO—O—, or —Si(CH$_3$)$_2$—O—Si(CH$_3$)$_2$—, and wherein:

$R^1$ represents a hydrogen atom or $C_1$-$C_6$alkyl;

with the proviso that oxygen atoms of linking groups are not directly linked to each other;

D represents a polymerizable group, which is an unsubstituted or substituted, aliphatic, aromatic and/or alicyclic diamine group, siloxane or maleinimide;

E represents —OCO—, —COO—, —OOC—, or —CO—;

$S^1$, $S^2$ each independently from each other represents a spacer unit, which is a single bond, a cyclic, straight-chain or branched, substituted or unsubstituted $C_1$-$C_{24}$alkylen, wherein one or more —C—, —CH—, or —CH$_2$— group may independently from each other be unreplaced or replaced by at least one linking group as described above and/or by at least one non-aromatic, aromatic, unsubstituted or substituted carbocyclic or heterocyclic group connected via bridging groups;

X, Y represent hydrogen;

n, n1 each independently from each other represents 1, 2, 3 or 4, with the proviso that if n is 2, 3, or 4, each A, B, $x_1$, E, $S^1$, $S^2$, X, Y are identical or different; and if n1 is 2, 3 or 4 each B, $x_1$ is identical or different; and with the proviso that if B is substituted with at least one fluorine then there is at least one additional polar group in formula (I') and (ii) a further compound of formula (I') wherein B is substituted by one, two, three, four, five, six or seven fluorine atoms.

* * * * *